US012502165B2

(12) United States Patent
Swift et al.

(10) Patent No.: US 12,502,165 B2
(45) Date of Patent: Dec. 23, 2025

(54) ILLUMINATED MEDICAL DEVICES

(71) Applicant: CooperSurgical, Inc., Trumbull, CT (US)

(72) Inventors: Jeffrey Ralph Swift, Boca Grande, FL (US); Jason Swift, Newburyport, MA (US); Matthew Traub, Andover, MA (US); Nicholas Lauder, Medford, MA (US)

(73) Assignee: CooperSurgical, Inc., Trumbull, CT (US)

(*) Notice: Subject to any disclaimer, the term of this patent is extended or adjusted under 35 U.S.C. 154(b) by 52 days.

(21) Appl. No.: 18/360,509

(22) Filed: Jul. 27, 2023

(65) Prior Publication Data

US 2023/0363751 A1 Nov. 16, 2023

Related U.S. Application Data

(63) Continuation of application No. 17/014,385, filed on Sep. 8, 2020, now Pat. No. 11,744,568, which is a continuation of application No. 16/659,924, filed on Oct. 22, 2019, now Pat. No. 10,799,229, which is a continuation of application No. 16/279,226, filed on Feb. 19, 2019, now Pat. No. 10,512,519.

(Continued)

(51) Int. Cl.

| | |
|---|---|
| ***A61B 17/02*** | (2006.01) |
| ***A61B 90/35*** | (2016.01) |
| *A61B 17/00* | (2006.01) |

(52) U.S. Cl.

CPC .......... *A61B 17/0206* (2013.01); *A61B 90/35* (2016.02); *A61B 2017/00734* (2013.01); *A61B 2218/008* (2013.01)

(58) Field of Classification Search

CPC ..... A61B 17/02; A61B 17/0206; A61B 90/35; A61B 90/30; A61B 1/32

See application file for complete search history.

(56) References Cited

U.S. PATENT DOCUMENTS

| | | | |
|---|---|---|---|
| 559,122 | A | 4/1896 | Daily |
| 659,182 | A | 10/1900 | Pilling |

(Continued)

FOREIGN PATENT DOCUMENTS

| | | | |
|---|---|---|---|
| CN | 2239235 | Y | 11/1996 |
| CN | 2265156 | Y | 10/1997 |

(Continued)

OTHER PUBLICATIONS

European Examination Report issued on Mar. 27, 2024, that issued in the corresponding European Patent Application No. 19757432.0.

(Continued)

*Primary Examiner* — Christopher J Beccia

(74) *Attorney, Agent, or Firm* — Fish & Richardson P.C.

(57) ABSTRACT

A surgical retractor comprising a blade having first and second opposing surfaces, and a handle extending from a proximal end of the blade, wherein the first surface of the blade includes a non-slip texture having a preferential grip in a first direction corresponding to direction of extraction of the surgical retractor from an incision and having a minimal or no grip in a second direction opposite to the first direction and in a third direction transverse to the first and second directions.

20 Claims, 32 Drawing Sheets

Related U.S. Application Data

(60) Provisional application No. 62/716,732, filed on Aug. 9, 2018, provisional application No. 62/632,571, filed on Feb. 20, 2018.

(56) References Cited

U.S. PATENT DOCUMENTS

| | | | |
|---|---|---|---|
| 2,235,979 | A | 3/1941 | Brown |
| 2,247,458 | A | 7/1941 | Wintemberg |
| 2,482,971 | A | 9/1949 | Golson |
| 2,592,190 | A | 4/1952 | Rubens et al. |
| 3,324,850 | A | 6/1967 | Gunning et al. |
| 3,332,414 | A | 7/1967 | Gasper |
| 3,532,088 | A | 10/1970 | Fiore |
| 3,592,199 | A | 7/1971 | Ostensen |
| 3,595,222 | A | 7/1971 | Vellacott |
| 3,638,644 | A | 2/1972 | Reick |
| 3,650,266 | A | 3/1972 | Pestka et al. |
| 3,675,641 | A | 7/1972 | Fiore |
| 3,716,047 | A | 2/1973 | Moore et al. |
| 3,729,006 | A | 4/1973 | Wilder et al. |
| 3,762,400 | A | 10/1973 | McDonald |
| 3,769,968 | A | 11/1973 | Blount et al. |
| 3,789,835 | A | 2/1974 | Whitman |
| 3,815,585 | A | 6/1974 | Fiore |
| 3,826,248 | A | 7/1974 | Gobels |
| 3,851,642 | A | 12/1974 | McDonald |
| 3,934,578 | A | 1/1976 | Heine |
| 3,945,371 | A | 3/1976 | Adelman |
| 3,978,850 | A | 9/1976 | Moore et al. |
| 4,067,323 | A | 1/1978 | Troutner |
| 4,156,424 | A | 5/1979 | Burgin |
| 4,210,133 | A | 7/1980 | Castaneda |
| 4,226,228 | A | 10/1980 | Shin et al. |
| 4,263,899 | A | 4/1981 | Burgin |
| 4,300,541 | A | 11/1981 | Burgin |
| 4,337,763 | A | 7/1982 | Petrassevich |
| 4,432,351 | A | 2/1984 | Hoary |
| 4,492,220 | A | 1/1985 | Hayes |
| 4,502,468 | A | 3/1985 | Burgin |
| 4,527,553 | A | 7/1985 | Upsher |
| 4,546,761 | A | 10/1985 | McCullough |
| 4,551,129 | A | 11/1985 | Coleman et al. |
| 4,562,832 | A | 1/1986 | Wilder |
| 4,566,439 | A | 1/1986 | Burgin |
| 4,574,784 | A | 3/1986 | Soloway |
| 4,597,383 | A | 7/1986 | Van Der Bel |
| 4,607,623 | A | 8/1986 | Bauman |
| 4,619,248 | A | 10/1986 | Walsh |
| 4,638,792 | A | 1/1987 | Burgin |
| 4,759,349 | A | 7/1988 | Betz et al. |
| 4,766,887 | A | 8/1988 | Cecil, Jr. et al. |
| 4,807,600 | A | 2/1989 | Hayes |
| 4,884,559 | A | 12/1989 | Collins |
| 4,905,670 | A | 3/1990 | Adair |
| 4,934,352 | A | 6/1990 | Sullivan, Jr. |
| 4,971,036 | A | 11/1990 | Collins |
| 5,018,507 | A | 5/1991 | Montaldi |
| 5,026,368 | A | 6/1991 | Adair |
| 5,054,906 | A | 10/1991 | Lyons, Jr. |
| 5,063,908 | A | 11/1991 | Collins |
| 5,143,054 | A | 9/1992 | Adair |
| 5,165,387 | A | 11/1992 | Woodson |
| 5,174,278 | A | 12/1992 | Babkow |
| 5,179,937 | A | 1/1993 | Lee |
| 5,179,938 | A | 1/1993 | Lonky |
| 5,222,271 | A | 6/1993 | Eganhouse |
| D337,384 | S | 7/1993 | Schucman |
| 5,231,973 | A | 8/1993 | Dickie |
| 5,318,009 | A | 6/1994 | Robinson |
| 5,329,938 | A | 7/1994 | Lonky |
| 5,427,152 | A | 6/1995 | Weber |
| 5,438,976 | A | 8/1995 | Nash |
| 5,465,709 | A | 11/1995 | Dickie et al. |
| 5,499,964 | A | 3/1996 | Beck et al. |
| 5,512,038 | A | 4/1996 | O'Neal et al. |
| 5,553,627 | A | 9/1996 | Newkirk |
| 5,695,492 | A | 12/1997 | Brown |
| 5,716,329 | A | 2/1998 | Dieter |
| 5,785,648 | A | 7/1998 | Min |
| 5,840,013 | A | 11/1998 | Lee et al. |
| 5,846,249 | A | 12/1998 | Thompson |
| 5,865,729 | A | 2/1999 | Meehan |
| 5,873,820 | A | 2/1999 | Norell |
| 5,879,304 | A | 3/1999 | Schuchman et al. |
| 5,888,195 | A | 3/1999 | Schneider |
| 5,899,854 | A | 5/1999 | Slishman |
| 5,902,315 | A | 5/1999 | Dubois |
| 5,916,150 | A | 6/1999 | Sillman |
| 5,967,971 | A | 10/1999 | Bolser |
| 6,001,077 | A | 12/1999 | Ellman et al. |
| 6,004,265 | A | 12/1999 | Hsu et al. |
| 6,036,638 | A | 3/2000 | Nwawka |
| 6,036,713 | A | 3/2000 | Kieturakis |
| 6,048,308 | A | 4/2000 | Strong |
| 6,080,105 | A | 6/2000 | Spears |
| 6,130,520 | A | 10/2000 | Wawro et al. |
| 6,176,824 | B1 | 1/2001 | Davis |
| 6,186,944 | B1 | 2/2001 | Tsai |
| 6,193,653 | B1 | 2/2001 | Evans et al. |
| 6,217,512 | B1 | 4/2001 | Salo et al. |
| 6,231,505 | B1 | 5/2001 | Martin |
| 6,231,506 | B1 | 5/2001 | Hu et al. |
| 6,254,247 | B1 | 7/2001 | Carson |
| 6,277,067 | B1 | 8/2001 | Blair |
| 6,319,199 | B1 | 11/2001 | Sheehan et al. |
| 6,346,085 | B1 | 2/2002 | Schiffman |
| 6,359,644 | B1 | 3/2002 | Salvati |
| 6,361,489 | B1 | 3/2002 | Tsai |
| 6,363,763 | B1 | 4/2002 | Geringer et al. |
| 6,379,296 | B1 | 4/2002 | Baggett |
| 6,379,299 | B1 | 4/2002 | Borodulin et al. |
| 6,394,111 | B1 | 5/2002 | Jacobs et al. |
| 6,394,950 | B1 | 5/2002 | Weiss |
| 6,413,208 | B1 | 7/2002 | Schöllhorn et al. |
| 6,416,465 | B2 | 7/2002 | Brau |
| 6,428,180 | B1 | 8/2002 | Karram et al. |
| 6,432,045 | B2 | 8/2002 | Lemperle et al. |
| 6,432,049 | B1 | 8/2002 | Banta |
| 6,436,033 | B2 | 8/2002 | Tan |
| 6,450,952 | B1 | 9/2002 | Rioux |
| 6,468,206 | B1 | 10/2002 | Hipps et al. |
| 6,468,232 | B1 | 10/2002 | Ashton-Miller et al. |
| 6,487,440 | B2 | 11/2002 | Deckert et al. |
| 6,504,985 | B2 | 1/2003 | Parker et al. |
| 6,523,973 | B2 | 2/2003 | Galli |
| 6,524,259 | B2 | 2/2003 | Baxter-Jones et al. |
| 6,569,089 | B1 | 5/2003 | Covington et al. |
| 6,569,091 | B2 | 5/2003 | Diokno et al. |
| 6,589,168 | B2 | 7/2003 | Thompson |
| 6,595,917 | B2 | 7/2003 | Nieto |
| 6,616,603 | B1 | 9/2003 | Fontana |
| 6,626,825 | B2 | 9/2003 | Tsai |
| 6,663,576 | B2 | 12/2003 | Gombrich et al. |
| 6,676,598 | B2 | 1/2004 | Rudischhauser et al. |
| 6,719,688 | B2 | 4/2004 | Pecherer et al. |
| 6,761,687 | B1 | 7/2004 | Doshi |
| 6,830,547 | B2 | 12/2004 | Weiss |
| 6,896,653 | B1 | 5/2005 | Vail, III et al. |
| 7,014,340 | B2 | 3/2006 | Betis |
| 7,029,439 | B2 | 4/2006 | Roberts et al. |
| D520,464 | S | 5/2006 | Strong |
| 7,223,223 | B2 | 5/2007 | Lindsay |
| 7,276,025 | B2 | 10/2007 | Roberts et al. |
| 7,306,559 | B2 | 12/2007 | Williams |
| 7,474,820 | B2 | 1/2009 | Vayser et al. |
| 7,492,116 | B2 | 2/2009 | Oleynikov et al. |
| 7,510,524 | B2 | 3/2009 | Vayser |
| 7,631,981 | B2 | 12/2009 | Miller et al. |
| 7,736,304 | B2 | 6/2010 | Pecherer |
| 7,758,203 | B2 | 7/2010 | McMahon et al. |
| 7,845,824 | B2 | 12/2010 | Robotham |
| 7,878,973 | B2 | 2/2011 | Yee et al. |
| 7,901,353 | B2 | 3/2011 | Vayser et al. |

(56) References Cited

U.S. PATENT DOCUMENTS

| | | | |
|---|---|---|---|
| 7,909,759 | B2 | 3/2011 | Pecherer |
| 7,967,809 | B2 | 6/2011 | Jay-Robinson |
| 8,012,089 | B2 | 9/2011 | Bayat |
| 8,047,987 | B2 | 11/2011 | Grey et al. |
| 8,052,702 | B2 | 11/2011 | Hess et al. |
| 8,088,066 | B2 | 1/2012 | Grey et al. |
| 8,096,945 | B2 | 1/2012 | Buchok et al. |
| 8,142,352 | B2 | 3/2012 | Vivenzio et al. |
| 8,142,353 | B2 | 3/2012 | Pecherer et al. |
| 8,157,728 | B2 | 4/2012 | Danna et al. |
| 8,162,824 | B2 | 4/2012 | Vayser et al. |
| 8,162,826 | B2 | 4/2012 | Pecherer et al. |
| 8,251,898 | B2 | 8/2012 | Pecherer |
| 8,285,093 | B2 | 10/2012 | Vayser et al. |
| 8,292,805 | B2 | 10/2012 | Vayser et al. |
| 8,317,693 | B2 | 11/2012 | Grey et al. |
| 8,388,523 | B2 | 3/2013 | Vivenzio et al. |
| 8,394,017 | B2 | 3/2013 | Kieffer |
| 8,435,175 | B2 | 5/2013 | McMahon et al. |
| 8,459,844 | B2 | 6/2013 | Lia et al. |
| 8,512,234 | B2 | 8/2013 | Grey et al. |
| 8,512,237 | B2 | 8/2013 | Bastia |
| 8,555,892 | B2 | 10/2013 | Traub |
| 8,594,472 | B2 | 11/2013 | Vayser et al. |
| 8,596,847 | B2 | 12/2013 | Vayser et al. |
| 8,628,879 | B2 | 1/2014 | Pecherer et al. |
| 8,651,704 | B1 | 2/2014 | Gordin et al. |
| 8,708,896 | B2 | 4/2014 | Vayser et al. |
| 8,786,210 | B2 | 7/2014 | Delucia |
| 8,795,162 | B2 | 8/2014 | Vayser et al. |
| 8,821,385 | B2 | 9/2014 | Naito |
| 8,870,761 | B2 | 10/2014 | Vayser et al. |
| 8,890,489 | B2 | 11/2014 | Wood |
| D719,652 | S | 12/2014 | Swift |
| 8,899,809 | B2 | 12/2014 | Vayser et al. |
| 8,979,745 | B2 | 3/2015 | Swift |
| 9,002,159 | B2 | 4/2015 | Sutherland et al. |
| 9,005,115 | B2 | 4/2015 | Vayser et al. |
| 9,044,161 | B2 | 6/2015 | Vayser et al. |
| 9,050,048 | B2 | 6/2015 | Nadershahi |
| 9,072,452 | B2 | 7/2015 | Vayser et al. |
| 9,072,455 | B2 | 7/2015 | Vayser et al. |
| D745,669 | S | 12/2015 | Swift |
| 9,198,566 | B2 | 12/2015 | Lia et al. |
| 9,229,165 | B2 | 1/2016 | Vayser et al. |
| 9,241,617 | B2 | 1/2016 | Grey et al. |
| D752,217 | S | 3/2016 | Swift |
| 9,271,709 | B2 | 3/2016 | Grey et al. |
| 9,271,710 | B2 | 3/2016 | Grey et al. |
| 9,282,878 | B2 | 3/2016 | Grey et al. |
| D753,295 | S | 4/2016 | Vivenzio et al. |
| 9,307,897 | B2 | 4/2016 | Swift |
| 9,308,054 | B2 | 4/2016 | Vayser et al. |
| 9,332,898 | B2 | 5/2016 | McMahon et al. |
| 9,429,746 | B2 | 8/2016 | Vayser et al. |
| 9,468,366 | B2 | 10/2016 | Grey et al. |
| 9,504,373 | B2 | 11/2016 | Vayser et al. |
| 9,510,737 | B2 | 12/2016 | Vayser et al. |
| 9,532,706 | B2 | 1/2017 | McMahon et al. |
| 9,574,742 | B2 | 2/2017 | Vayser et al. |
| 9,629,529 | B1 | 4/2017 | Indovina et al. |
| 9,636,004 | B2 | 5/2017 | Lia et al. |
| 9,636,182 | B2 | 5/2017 | Vayser et al. |
| 9,718,130 | B1 | 8/2017 | Vayser et al. |
| 9,763,743 | B2 | 9/2017 | Lin et al. |
| 9,808,231 | B2 | 11/2017 | Miraki et al. |
| 9,814,377 | B2 | 11/2017 | Lia et al. |
| 9,820,638 | B2 | 11/2017 | Cheng |
| 9,820,729 | B2 | 11/2017 | Miles et al. |
| 9,826,892 | B2 | 11/2017 | Dresher et al. |
| 9,833,295 | B2 | 12/2017 | Vayser et al. |
| 9,833,308 | B2 | 12/2017 | Dye |
| 9,844,364 | B2 | 12/2017 | Grey et al. |
| 9,861,349 | B2 | 1/2018 | Nadershahi et al. |
| 9,867,531 | B2 | 1/2018 | Pacey et al. |
| 9,867,602 | B2 | 1/2018 | Swift |
| 9,877,639 | B2 | 1/2018 | Grey et al. |
| 9,877,644 | B2 | 1/2018 | Greenstein et al. |
| D809,660 | S | 2/2018 | Nguyen et al. |
| 9,883,792 | B2 | 2/2018 | McMahon et al. |
| 9,888,957 | B2 | 2/2018 | Wolf et al. |
| 9,907,544 | B2 | 3/2018 | Nadershahi et al. |
| 9,913,682 | B2 | 3/2018 | Wolf et al. |
| 9,918,618 | B2 | 3/2018 | Molnar |
| 9,918,802 | B2 | 3/2018 | Coppersmith et al. |
| 9,931,028 | B2 | 4/2018 | Lia et al. |
| 9,943,295 | B2 | 4/2018 | King |
| 9,949,814 | B2 | 4/2018 | Alexander et al. |
| 9,955,858 | B2 | 5/2018 | Pamnani et al. |
| 9,968,262 | B2 | 5/2018 | Greenstein et al. |
| 9,968,346 | B2 | 5/2018 | Alexander et al. |
| 9,980,710 | B2 | 5/2018 | Seifert et al. |
| 9,986,901 | B2 | 6/2018 | Grey et al. |
| 9,986,903 | B2 | 6/2018 | Nadershahi et al. |
| 9,986,988 | B2 | 6/2018 | Ferro et al. |
| 9,999,345 | B2 | 6/2018 | Vayser et al. |
| 10,004,392 | B2 | 6/2018 | Millard et al. |
| 10,004,393 | B2 | 6/2018 | Kucklick |
| 10,028,648 | B2 | 7/2018 | Goldfain et al. |
| 10,028,649 | B2 | 7/2018 | Salvati et al. |
| 10,028,780 | B2 | 7/2018 | Wolf et al. |
| 10,045,686 | B2 | 8/2018 | Ou et al. |
| 10,045,731 | B2 | 8/2018 | Prasad et al. |
| 10,052,432 | B2 | 8/2018 | Dexter et al. |
| 10,064,611 | B2 | 9/2018 | Ross et al. |
| 10,064,613 | B2 | 9/2018 | Davis et al. |
| 10,068,173 | B2 | 9/2018 | Vayser et al. |
| 10,092,176 | B2 | 10/2018 | Kienzle et al. |
| 10,092,281 | B2 | 10/2018 | Perler et al. |
| 10,098,530 | B2 | 10/2018 | McMahon et al. |
| 10,105,043 | B2 | 10/2018 | George |
| 10,117,646 | B2 | 11/2018 | Friedrich et al. |
| 10,130,441 | B2 | 11/2018 | Martinez |
| 10,166,016 | B2 | 1/2019 | Shimizu et al. |
| 10,172,601 | B2 | 1/2019 | Ahn |
| 10,174,933 | B2 | 1/2019 | Phillips, Jr. et al. |
| 10,188,298 | B2 | 1/2019 | Greenstein et al. |
| 10,213,271 | B2 | 2/2019 | Duggal et al. |
| 10,219,800 | B2 | 3/2019 | Tsubouchi |
| 10,220,445 | B2 | 3/2019 | Vayser et al. |
| 10,226,555 | B2 | 3/2019 | Vayser et al. |
| 10,238,462 | B2 | 3/2019 | Wood et al. |
| D846,119 | S | 4/2019 | Greeley et al. |
| 10,278,571 | B2 | 5/2019 | Poormand |
| 10,292,782 | B2 | 5/2019 | Haverich et al. |
| 10,292,784 | B2 | 5/2019 | Duggal et al. |
| 10,321,969 | B2 | 6/2019 | Wayne et al. |
| 10,342,525 | B2 | 7/2019 | Wilson |
| 10,456,190 | B2 | 10/2019 | Vayser |
| 10,499,974 | B2 | 12/2019 | Heim et al. |
| 10,500,010 | B2 | 12/2019 | Vayser et al. |
| 10,512,518 | B2 | 12/2019 | Vayser et al. |
| 10,512,520 | B2 | 12/2019 | Wayne et al. |
| 10,531,933 | B2 | 1/2020 | Vayser et al. |
| 10,548,682 | B2 | 2/2020 | Vayser et al. |
| 10,568,712 | B2 | 2/2020 | Vayser et al. |
| 10,675,115 | B2 | 6/2020 | Vayser et al. |
| 10,729,511 | B2 | 8/2020 | Vayser et al. |
| 10,729,512 | B2 | 8/2020 | Wayne et al. |
| 10,939,899 | B2 | 3/2021 | Swift |
| 11,540,817 | B2 | 1/2023 | Gallagher et al. |
| 11,622,758 | B2 | 4/2023 | Swift et al. |
| 11,744,568 | B2 | 9/2023 | Swift et al. |
| 2001/0029044 | A1 | 10/2001 | Gombrich et al. |
| 2002/0009275 | A1 | 1/2002 | Williams et al. |
| 2002/0022769 | A1 | 2/2002 | Smith et al. |
| 2002/0038075 | A1 | 3/2002 | Tsai |
| 2002/0038076 | A1 | 3/2002 | Sheehan et al. |
| 2002/0055670 | A1 | 5/2002 | Weiss |
| 2002/0115909 | A1 | 8/2002 | Bolser |
| 2002/0156350 | A1 | 10/2002 | Nieto |
| 2002/0165435 | A1 | 11/2002 | Weiss |
| 2002/0198471 | A1 | 12/2002 | Baxter-Jones et al. |
| 2003/0095781 | A1 | 5/2003 | Willaims |

(56) References Cited

U.S. PATENT DOCUMENTS

| | | | |
|---|---|---|---|
| 2003/0105387 | A1 | 6/2003 | Frumovitz et al. |
| 2003/0139673 | A1 | 7/2003 | Vivenzio et al. |
| 2003/0158502 | A1 | 8/2003 | Baxter-Jones et al. |
| 2003/0176772 | A1 | 9/2003 | Yang |
| 2003/0187331 | A1 | 10/2003 | Faludi et al. |
| 2004/0026829 | A1 | 2/2004 | Van Der Weegen |
| 2004/0054260 | A1 | 3/2004 | Klaassen et al. |
| 2004/0141175 | A1 | 7/2004 | Baldwin et al. |
| 2004/0183482 | A1 | 9/2004 | Roberts et al. |
| 2004/0184288 | A1 | 9/2004 | Bettis |
| 2004/0186355 | A1 | 9/2004 | Strong |
| 2004/0254428 | A1 | 12/2004 | Ritland |
| 2005/0065496 | A1 | 3/2005 | Simon et al. |
| 2005/0085699 | A1 | 4/2005 | Weiss |
| 2005/0085723 | A1 | 4/2005 | Huebner |
| 2005/0093718 | A1 | 5/2005 | Martin |
| 2005/0125015 | A1 | 6/2005 | McNally-Heintzelman et al. |
| 2005/0159649 | A1 | 7/2005 | Patel |
| 2005/0182301 | A1 | 8/2005 | Acker et al. |
| 2005/0192482 | A1 | 9/2005 | Carpenter |
| 2005/0215858 | A1 | 9/2005 | Vail, III |
| 2005/0240081 | A1 | 10/2005 | Eliachar |
| 2005/0277811 | A1 | 12/2005 | Richards et al. |
| 2006/0084843 | A1 | 4/2006 | Sommerich et al. |
| 2006/0122463 | A1 | 6/2006 | Klaassen |
| 2006/0155276 | A1 | 7/2006 | Walulik et al. |
| 2006/0189847 | A1 | 8/2006 | Yee et al. |
| 2006/0200186 | A1 | 9/2006 | Marchek et al. |
| 2007/0043264 | A1 | 2/2007 | Gillis et al. |
| 2007/0060795 | A1 | 3/2007 | Vayser et al. |
| 2007/0060938 | A1 | 3/2007 | Dziadik et al. |
| 2007/0066872 | A1 | 3/2007 | Morrison et al. |
| 2007/0100212 | A1 | 5/2007 | Pimenta et al. |
| 2007/0208226 | A1 | 9/2007 | Grey et al. |
| 2007/0230164 | A1 | 10/2007 | Vivenzio et al. |
| 2007/0230167 | A1 | 10/2007 | McMahon et al. |
| 2007/0255110 | A1 | 11/2007 | Wax et al. |
| 2007/0270866 | A1 | 11/2007 | Von Jako |
| 2007/0287888 | A1 | 12/2007 | Lovell et al. |
| 2008/0002426 | A1 | 1/2008 | Vayser et al. |
| 2008/0027461 | A1 | 1/2008 | Vaquero et al. |
| 2008/0108877 | A1 | 5/2008 | Bayat |
| 2008/0113312 | A1 | 5/2008 | Ortega |
| 2008/0221569 | A1 | 9/2008 | Moore et al. |
| 2008/0228038 | A1 | 9/2008 | McMahon et al. |
| 2008/0269564 | A1 | 10/2008 | Gelnett |
| 2008/0269565 | A1 | 10/2008 | McMahon et al. |
| 2008/0278936 | A1 | 11/2008 | Kurth et al. |
| 2009/0018400 | A1 | 1/2009 | Raymond et al. |
| 2009/0069634 | A1 | 3/2009 | Larkin |
| 2009/0097236 | A1 | 4/2009 | Miller et al. |
| 2009/0112068 | A1 | 4/2009 | Grey et al. |
| 2009/0275803 | A1 | 11/2009 | Krauter et al. |
| 2009/0287192 | A1 | 11/2009 | Vivenzio et al. |
| 2009/0312610 | A1 | 12/2009 | Buchok et al. |
| 2010/0036382 | A1 | 2/2010 | Bonnadier |
| 2010/0041955 | A1 | 2/2010 | Grey et al. |
| 2010/0097794 | A1 | 4/2010 | Teng et al. |
| 2010/0190129 | A1 | 7/2010 | Paz |
| 2010/0191062 | A1 | 7/2010 | Kieffer |
| 2010/0292533 | A1 | 11/2010 | Kasahara et al. |
| 2011/0275894 | A1 | 11/2011 | Mackin |
| 2012/0041268 | A1 | 2/2012 | Grey et al. |
| 2012/0055470 | A1 | 3/2012 | Pecherer et al. |
| 2012/0059226 | A1 | 3/2012 | Funt |
| 2012/0078060 | A1 | 3/2012 | Swift |
| 2012/0116170 | A1 | 5/2012 | Vayser et al. |
| 2012/0232352 | A1 | 9/2012 | Lin et al. |
| 2012/0243212 | A1 | 9/2012 | Smith et al. |
| 2013/0018230 | A1 | 1/2013 | Su et al. |
| 2013/0021798 | A1 | 1/2013 | Chen et al. |
| 2013/0041229 | A2 | 2/2013 | Hahn et al. |
| 2013/0092421 | A1* | 4/2013 | Kajiya ................ H05K 1/0206 174/252 |
| 2013/0102850 | A1 | 4/2013 | Fiorella |
| 2013/0102887 | A1 | 4/2013 | Thompson et al. |
| 2013/0109910 | A1 | 5/2013 | Alexander et al. |
| 2013/0158345 | A1 | 6/2013 | Majlessi |
| 2013/0197313 | A1 | 8/2013 | Wan |
| 2013/0245381 | A1 | 9/2013 | Dang et al. |
| 2013/0245657 | A1 | 9/2013 | Deville et al. |
| 2013/0267786 | A1 | 10/2013 | Vayser et al. |
| 2013/0281784 | A1 | 10/2013 | Ray |
| 2013/0324801 | A1 | 12/2013 | Grey et al. |
| 2014/0088371 | A1 | 3/2014 | Vayser et al. |
| 2014/0179998 | A1 | 6/2014 | Pacey et al. |
| 2014/0202459 | A1 | 7/2014 | Iqbal |
| 2014/0228875 | A1 | 8/2014 | Saadat |
| 2014/0257039 | A1 | 9/2014 | Feldman |
| 2014/0275790 | A1 | 9/2014 | Vivenzio et al. |
| 2014/0275792 | A1 | 9/2014 | Hawkins et al. |
| 2014/0309499 | A1 | 10/2014 | Swift |
| 2014/0316211 | A1 | 10/2014 | Hermle |
| 2014/0323800 | A1 | 10/2014 | Dye |
| 2014/0323811 | A1* | 10/2014 | DeSantis ................ A61B 17/02 600/245 |
| 2014/0364695 | A1 | 12/2014 | Nadershahi et al. |
| 2014/0371536 | A1 | 12/2014 | Miller et al. |
| 2015/0018625 | A1 | 1/2015 | Miraki et al. |
| 2015/0018627 | A1 | 1/2015 | Vayser et al. |
| 2015/0157469 | A1 | 6/2015 | Prado et al. |
| 2015/0238070 | A1 | 8/2015 | Lia et al. |
| 2015/0250555 | A1 | 9/2015 | Haverich et al. |
| 2015/0285382 | A1 | 10/2015 | Kienreich et al. |
| 2015/0289757 | A1 | 10/2015 | Swift |
| 2016/0000305 | A1 | 1/2016 | Elbaz et al. |
| 2016/0030128 | A1 | 2/2016 | Duggal et al. |
| 2016/0038032 | A1 | 2/2016 | Dan |
| 2016/0066915 | A1 | 3/2016 | Baber et al. |
| 2016/0081833 | A1 | 3/2016 | Leblanc et al. |
| 2016/0095506 | A1 | 4/2016 | Dan et al. |
| 2016/0100751 | A1 | 4/2016 | Davis et al. |
| 2016/0151058 | A1* | 6/2016 | Ferro .................... A61B 17/02 600/215 |
| 2016/0302657 | A1 | 10/2016 | Hussey et al. |
| 2016/0354072 | A1 | 12/2016 | Swift |
| 2017/0007228 | A1 | 1/2017 | Costabile |
| 2017/0020621 | A1 | 1/2017 | Huldin et al. |
| 2017/0059400 | A1 | 3/2017 | Murphy et al. |
| 2017/0065282 | A1 | 3/2017 | Mathis et al. |
| 2017/0079518 | A1 | 3/2017 | Elbaz et al. |
| 2017/0172404 | A1 | 6/2017 | McMahon et al. |
| 2017/0172555 | A1 | 6/2017 | Shimizu et al. |
| 2017/0181605 | A1 | 6/2017 | Lalli et al. |
| 2017/0181607 | A1 | 6/2017 | Lalli et al. |
| 2017/0181615 | A1 | 6/2017 | Vella et al. |
| 2017/0181616 | A1 | 6/2017 | Vella et al. |
| 2017/0224206 | A1 | 8/2017 | Vayser |
| 2017/0231712 | A1 | 8/2017 | Vayser |
| 2017/0245849 | A1 | 8/2017 | Swift |
| 2017/0296162 | A1 | 10/2017 | Wan |
| 2017/0300623 | A1 | 10/2017 | Rosenblatt et al. |
| 2017/0303903 | A1 | 10/2017 | De Koning et al. |
| 2017/0347871 | A1 | 12/2017 | Wallace et al. |
| 2017/0360423 | A1 | 12/2017 | Stevenson et al. |
| 2018/0000469 | A1 | 1/2018 | Wood et al. |
| 2018/0008137 | A1 | 1/2018 | Poormand |
| 2018/0008138 | A1 | 1/2018 | Thommen et al. |
| 2018/0008368 | A1 | 1/2018 | Duggal et al. |
| 2018/0014721 | A1 | 1/2018 | Rullo et al. |
| 2018/0014842 | A1 | 1/2018 | Shener-Irmakoglu |
| 2018/0014900 | A1 | 1/2018 | Vayser et al. |
| 2018/0021100 | A1 | 1/2018 | Swift |
| 2018/0036095 | A1 | 2/2018 | Vayser et al. |
| 2018/0042596 | A1 | 2/2018 | Tsubouchi |
| 2018/0064316 | A1 | 3/2018 | Charles et al. |
| 2018/0064317 | A1 | 3/2018 | Tesar |
| 2018/0078301 | A1 | 3/2018 | Vayser |
| 2018/0116581 | A1 | 5/2018 | Prasad et al. |
| 2018/0125336 | A1 | 5/2018 | Goldfarb et al. |
| 2018/0125347 | A1 | 5/2018 | Czyzewski et al. |
| 2018/0132710 | A1 | 5/2018 | Pacey et al. |
| 2018/0132970 | A1 | 5/2018 | Ritter |
| 2018/0153391 | A1 | 6/2018 | McMahon et al. |

(56) References Cited

U.S. PATENT DOCUMENTS

| | | | |
|---|---|---|---|
| 2018/0156448 | A1 | 6/2018 | Phillips, Jr. et al. |
| 2018/0206832 | A1 | 7/2018 | Greeley et al. |
| 2018/0228376 | A1 | 8/2018 | Greenstein et al. |
| 2018/0228483 | A1 | 8/2018 | Duggal et al. |
| 2018/0235444 | A1 | 8/2018 | Tsai |
| 2018/0235592 | A1 | 8/2018 | Kass et al. |
| 2018/0249902 | A1 | 9/2018 | Grey et al. |
| 2018/0263480 | A1 | 9/2018 | Lalli et al. |
| 2018/0271581 | A1 | 9/2018 | Ou et al. |
| 2018/0280011 | A1 | 10/2018 | Ferro et al. |
| 2018/0296082 | A1 | 10/2018 | Salvati et al. |
| 2018/0296204 | A1 | 10/2018 | Davis |
| 2018/0317746 | A1 | 11/2018 | Lalli et al. |
| 2018/0317752 | A1 | 11/2018 | Cybulski et al. |
| 2018/0317902 | A1 | 11/2018 | Green et al. |
| 2018/0328572 | A1 | 11/2018 | Kennedy et al. |
| 2019/0038273 | A1 | 2/2019 | Perler et al. |
| 2019/0049655 | A1 | 2/2019 | Zagatsky et al. |
| 2019/0076138 | A1 | 3/2019 | Opperman |
| 2019/0083079 | A1 | 3/2019 | Shimizu et al. |
| 2019/0133432 | A1 | 5/2019 | Tsai |
| 2019/0143006 | A1 | 5/2019 | Vayser et al. |
| 2019/0143414 | A1 | 5/2019 | Vayser et al. |
| 2019/0150422 | A1 | 5/2019 | Welch |
| 2019/0150725 | A1 | 5/2019 | Ramanujam et al. |
| 2019/0150739 | A1 | 5/2019 | Wawro et al. |
| 2019/0150786 | A1 | 5/2019 | Vassallo et al. |
| 2019/0167111 | A1 | 6/2019 | Greenstein et al. |
| 2019/0167378 | A1 | 6/2019 | Wood et al. |
| 2019/0190293 | A1 | 6/2019 | Wawro et al. |
| 2019/0223708 | A1 | 7/2019 | Recanati et al. |
| 2019/0254512 | A1 | 8/2019 | Spiertz |
| 2019/0335988 | A1 | 11/2019 | Lia et al. |
| 2019/0343379 | A1 | 11/2019 | Altamura |
| 2019/0365217 | A1 | 12/2019 | Hegenberger |
| 2020/0008694 | A1 | 1/2020 | Karla et al. |
| 2020/0046216 | A1 | 2/2020 | Moein |
| 2020/0069171 | A1 | 3/2020 | Miller et al. |
| 2020/0107714 | A1 | 4/2020 | Bar-or et al. |
| 2020/0253467 | A1 | 8/2020 | Lees et al. |
| 2020/0337541 | A1 | 10/2020 | Vivenzio et al. |
| 2021/0145270 | A1 | 5/2021 | Altamura |

FOREIGN PATENT DOCUMENTS

| | | | |
|---|---|---|---|
| CN | 2516109 | Y | 10/2002 |
| CN | 2629738 | Y | 8/2004 |
| CN | 1565664 | A | 1/2005 |
| CN | 2668152 | Y | 1/2005 |
| CN | 1717195 | A | 1/2006 |
| CN | 101179982 | A | 5/2008 |
| CN | 201055387 | Y | 5/2008 |
| CN | 203591245 | U | 5/2008 |
| CN | 201139589 | Y | 10/2008 |
| CN | 102415869 | A | 4/2012 |
| CN | 103154793 | A | 6/2013 |
| CN | 302536685 | S | 8/2013 |
| CN | 103925266 | A | 7/2014 |
| CN | 203898367 | | 10/2014 |
| CN | 102573700 | B | 12/2014 |
| DE | 2128855 | A | 12/1972 |
| DE | 10216618 | A1 | 1/2003 |
| DE | 202004002963 | U1 | 5/2004 |
| DE | 102005002220 | A1 | 10/2005 |
| DE | 202005019780 | U1 | 5/2006 |
| DE | 600 33 612 | T2 | 12/2007 |
| DE | 202010017638 | | 5/2012 |
| DE | 202010017638 | U | 5/2012 |
| EP | 0190014 | A2 | 8/1986 |
| EP | 1074224 | | 7/2001 |
| EP | 1074224 | A2 | 7/2001 |
| FR | 2490478 | A1 | 3/1982 |
| GB | 2505463 | | 5/2014 |
| GB | 2505463 | A | 5/2014 |
| RU | 2187972 | C2 | 8/2002 |
| RU | 2308873 | C2 | 10/2007 |
| WO | 9825512 | A1 | 6/1998 |
| WO | 0137739 | A1 | 5/2001 |
| WO | WO 0137739 | | 5/2001 |
| WO | 01/62137 | A2 | 8/2001 |
| WO | WO 2001-062137 | | 8/2001 |
| WO | 03082123 | A2 | 10/2003 |
| WO | 2004064624 | A1 | 8/2004 |
| WO | 2006107877 | A2 | 10/2006 |
| WO | 2006107878 | A2 | 10/2006 |
| WO | 2007/084641 | A2 | 7/2007 |
| WO | 2009/090383 | A2 | 7/2009 |
| WO | 2009137017 | A2 | 11/2009 |
| WO | 2013-044151 | A1 | 3/2013 |
| WO | 2014-041172 | A1 | 3/2014 |
| WO | 2006121530 | A2 | 11/2016 |
| WO | 2016196788 | A1 | 12/2016 |
| WO | WO 2016-196788 | | 12/2016 |

OTHER PUBLICATIONS

International Search Report for International application No. PCT/US2016/016154 issued May 19, 2016 for corresponding U.S. Appl. No. 14/614,413.

International Search Report, for International application No. PCT/US2016/035508 issued Sep. 15, 2016 for corresponding U.S. Appl. No. 15/171,581.

International Search Report for International application No. PCT/US2016/036833 issued Jan. 19, 2017.

U.S. Patent references 121-125 and U.S. Published Patent Application references 48 and 50 were cited in an Office Action issued in U.S. Appl. No. 15/171,581.

U.S. Published Patent Application references 47, 49 and 51 were cited in a PCT Search Report issued in PCT Application No. PCT/US2017/042617.

The above foreign patent documents 18, 21, 22, 23 and 24 were cited in a Nov. 1, 2017 Chinese Office Action, that issued in Chinese Patent Application No. 201510543086.7.

The above foreign patent documents 21, 22 and 26 was cited in the Jul. 16, 2018 Chinese Office Action, that issued in Chinese Patent Application No. 201510543086.7.

Solvey, Techinical Data Sheet, lxef 1022 polyarylamide, Feb. 13, 2015, pp. 1-5.

http://www.makeitfrom.com/material-properties/Polyetheretheketone-PEEK, printed on Oct. 9, 2016, pp. 1-9.

https://web.archive.org/web/20160618175418/http://bihlermed.com:80/scintillant/; Home—Scintillant® Surgical Light: Scintillant® Surgical Light; printed Oct. 19, 2022, 1 page.

International Search Report of International Application No. PCT/US2019/018473 issued on Feb. 19, 2019.

Office Action issued in U.S. Appl. No. 15/171,581.

International Search Report for International application No. PCT/US2021/017768 issued May 27, 2021.

International Search Report for International application No. PCT/US2021/014076 issued Apr. 15, 2021.

https://web.archive.org/web/20160618175418/http://bihlermed.com:80/scintillant/; Home—Scintillant® Surgical Light : Scintillant® Surgical Light; printed Oct. 19, 2022 (One Page).

The above documents were cited in a European Search Report issued on Nov. 23, 2018, that issued in the corresponding European Patent Application No. 16747107.7.

The above patent was cited in a Oct. 29, 2018 Chinese Office Action, that issued in Chinese Patent Application No. 201711159829.6.

International Search Report of PCT/US2018/054925, Oct. 9, 2018.

Pankaj Saxena, et al., Hydrodissection Technique of Harvesting Left Internal Thoracic Artery, Department of Cardiac Surgery, The Prince Charles Hospital, Chermside, Brisbane, Queensland, Australia, Thoracic Artery, Ann Thorac Surg., 2005; 80:335-6.

The above U.S. Publications documents #1 and #2 were cited in a Supplementary European Search Report issued on Apr. 24, 2019, that issued in European Patent Application No. 16804432.9.

(56) References Cited

OTHER PUBLICATIONS

OBP Medical—OfficeSpec, Premier Speculum for In-Office Procedures published Nov. 30, 2009 (1 page).
OBP Medical—ER-Spec Obgyn Brochure published Nov. 19, 2014 (2 pages).
OBP Medical—ER-Spec Brochure, Light Source Now 10X Brighter published Oct. 30, 2012 (1 page).
OBP Medical—ER-Spec Product Presentation published Apr. 16, 2014 (12 pages).
OBP Medical—ER-Spec Brochure published Apr. 11, 2013 (2 pages).
OBP Medical—ER-Spec Brochure published Feb. 4, 2013 (2 pages).
OBP Medical—ER-Spec Brochure, Light Source Now 10X Brighter published Jan. 23, 2013 (1 page).
Redefining illumination, Eikon LT Adapt SE for optimal precision and protection (2019), Stryker, www.stryker.com/surgical (3 pages).
Opposition, "Brief Communication," in European Appln. No. 16804432.9, mailed on Aug. 1, 2025, 26 pages.
Opposition, "CLEAR-TRAC: Single-Use Surgical Retractor with Built-In Light Source," Exhibit D6 in European Appln. No. 16804432.9, Apr. 16, 2014, mailed on May 30, 2024, 2 pages.
Opposition, "Notice of Opposition against European Patent No. 3302292," in European Appln. No. 16804432.9, mailed on May 30, 2024, 26 pages.
Opposition, "OBP Medical CLEAR-TRAC," Exhibit D7 in European Appln. No. 16804432.9, available on or before Jun. 26, 2014, via Internet Archive: Wayback Machine URL<https://web.archive.org/web/20140626121552mp_/https://obpmedical.com/product/clear-trac/#hospital>, mailed on May 30, 2024, 3 pages.
Opposition, "Reply to Observations made by the Patent Proprietor(s)," in European Appln. No. 16804432.9, mailed on Feb. 26, 2025, 13 pages.
Extended European Search Report in European Appln. No. 25188102.5, mailed on Nov. 14, 2025, 11 pages.

* cited by examiner

100

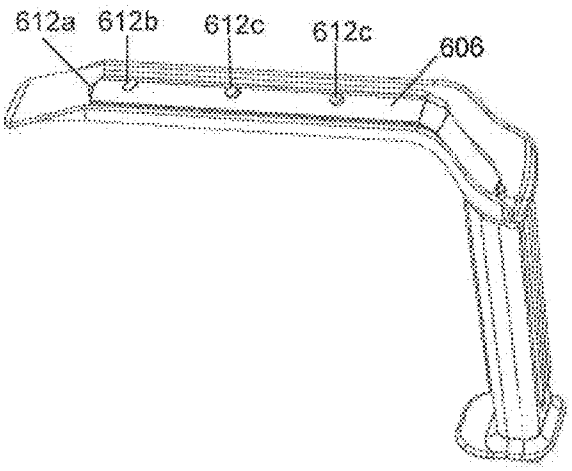
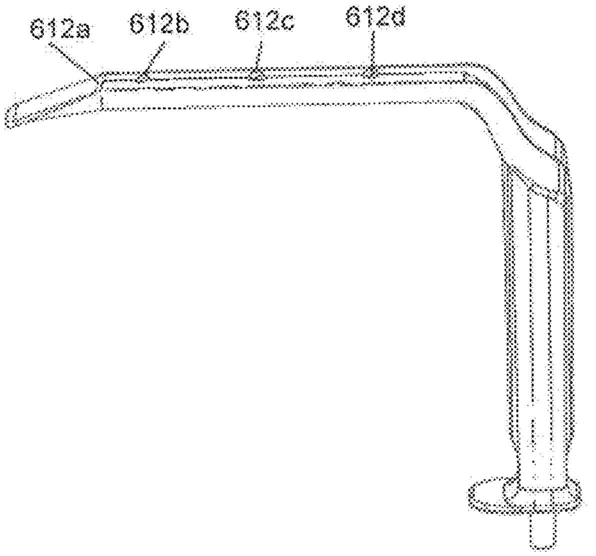
600
FIG. 6A
FIG. 6B

900

1000

| Texture | Description | Image | Insertion Force (lb) | Removal Force (lb) | Insertion | Grip | Range |
|---|---|---|---|---|---|---|---|
| 1 | sharp, more loosely packed | | 0.756 | 1.544 | | | 2.040 |
| 2 | Sharp, mid packed | | 0.62 | 1.34 | | | 1.972 |
| 3 | Rounded, loosely packed | | 0.744 | 1.412 | | | 1.920 |
| 4 | 7 ribs, reduced radii and extended wall | | 0.864 | 1.528 | | | 1.916 |
| 5 | Sharp, loosely packed | | 0.724 | 1.3 | | | 1.828 |
| 6 | Sharp, loosely packed, multidirectional | | 0.724 | 1.232 | | | 1.760 |
| 7 | D with 5 ribs | | 0.824 | 1.304 | | | 1.732 |
| 8 | D with 15 ribs | | 0.956 | 1.412 | | | 1.708 |
| 9 | D with 6 ribs | | 0.928 | 1.316 | | | 1.640 |
| 10 | Newly shaped rib | | 0.676 | 1 | | | 1.576 |
| 11 | D with less wall extension | | 1.252 | 1.524 | | | 1.524 |

1400

FIG. 15A
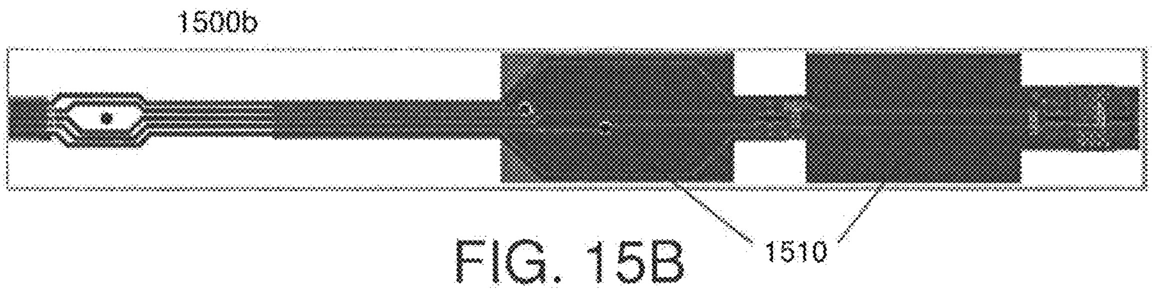
FIG. 15B
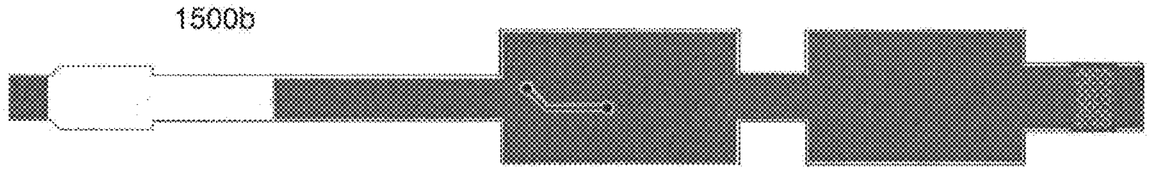
FIG. 15C
1500d
| LAYER | FOIL | Thickness (μm) |
|---|---|---|
| Top Soldermask | Coverlay | 25 |
| Top Layer | 2 Oz Copper | 71 |
| Flex Film | Flex Dielectric | 50.8 |
| Bottom Layer | 2 Oz Copper | 71 |
| Bottom Soldermask | Coverlay | 25 |
FIG. 15D

ILLUMINATED MEDICAL DEVICES

CROSS-REFERENCE TO RELATED APPLICATIONS

This application is a continuation of U.S. patent application Ser. No. 17/014,385 filed on Sep. 8, 2020, which is a continuation of U.S. patent application Ser. No. 16/659,924 filed on Oct. 22, 2019, which is a continuation of U.S. patent application Ser. No. 16/279,226 filed on Feb. 19, 2019 and issued as U.S. Pat. No. 10,512,519 on Dec. 24, 2019, which claims benefit of U.S. Provisional Application Nos. 62/632,571 filed on Feb. 20, 2018 and 62/716,732 filed on Aug. 9, 2018. The entire disclosures of these applications are incorporated herein by reference.

FIELD OF INVENTION

The present invention relates to medical devices and, more particularly, to illuminated medical devices having light sources to illuminate surgical fields.

BACKGROUND

Illuminating body cavities using a medical device is a well-documented problem in the medical field. In one aspect, existing medical devices fail to provide sufficient illumination. That is, most medical devices with integrated light sources often fail to direct or concentrate illumination to a desired surgical field. In other cases, existing medical devices illuminate an overly large area and create a glare that interferes with a physician's field of view. In another aspect, current lighting technology creates heat as a by-product. Even high efficiency LEDs only convert 30-40% of their energy into light and the rest is converted into heat energy. This heat energy has the potential to burn patients and to damage tissue, and thus, must be avoided. Accordingly, there is a need for a solution that addresses the various shortcomings of existing illuminated medical/surgical devices.

A new trend in illuminated medical devices is a "single-use" configuration that eliminates a need for sterilization or a risk of cross contamination. Such medical devices are generally manufactured with light and inexpensive material, such as plastic, and are wholly disposable after a single use. Once disposed, medical devices are incinerated in accordance with "bio-hazardous waste" requirements. However, when a single use illuminated medical device with a battery power source is disposed with the battery still intact, incineration of heavy metals contained in the battery may release toxic gases into the atmosphere causing environmental issues. Accordingly, there is a need for a mechanism to separate and/or recycle the batteries from illuminated medical devices prior to their disposal and incineration.

Moreover, most illuminated medical devices often require a short assembly of parts prior to their use. This often creates a problem in an urgent environment where surgeons and/or other medical professionals cannot afford to waste precious time in assembling a new device prior to its use. Shipping illuminated medical devices pre-assembled is usually not a viable solution because such method may violate various regulations for manufacturing and shipping medical devices, particularly devices that use batteries or other power sources. Accordingly, there is a need for a mechanism that allows for a quick and easy assembly of illuminated medical devices upon use.

SUMMARY OF THE INVENTION

It is an object of the present invention to provide a medical device with an illumination assembly having a plurality of light sources in which each light source is particularly configured and positioned to maximize illumination and visibility to desired surgical fields. In certain embodiments, each light source is configured and positioned to provide illumination only to the desired surgical field(s) while not providing or limiting illumination outside of the desired surgical fields. It is another object of the present invention to provide a medical device with an illumination assembly using a flexible circuit board to particularly configure and position light sources for illuminating surgical fields. It is yet another object of the present invention to provide a medical device that uses a specially designed flexible circuit board that improves thermal dissipation. It is a further object of the present invention to provide a medical device with a simple assembly mechanism that can quickly change from an open circuit configuration to a closed circuitry prior to actual use of the medical device. It is still a further object of the present invention provide a medical device with a mechanism to easily separate batteries from the rest of the medical device prior to disposal. Finally, it is also an object of the present invention to provide a medical device that achieves any one of the above noted objects while having an ergonomic design that gives rise to a more secure grip and an easier control for operating the medical device.

In accordance with the present invention, surgical retractor is provided that comprises a handle and a blade extending at an angle from the handle, an illumination assembly having a plurality of direct light sources provided on the blade, at least one of the light sources being angled differently relative to the blade than another one of the light sources, and a cover configured to enclose the illumination assembly, wherein the cover comprises a plurality of openings, each opening corresponding in position to a respective light source of the illumination assembly when the cover is attached to the blade. The cover may form a space for at least one smoke evacuation channel between the cover and the blade, and the surgical retractor may also include a vacuum port provided at a distal end of the handle and in fluid communication with the smoke evacuation channel, and an operative assembly with at least one switch for controlling the plurality of light sources. The switch(es) may be used to control at least one of activation, deactivation, brightness and color of each light source. In certain embodiments, the operative assembly comprises a potentiometer for controlling at least one of brightness and color of each light source. In some embodiments, the cover includes one or more filters in the input area of the at least one smoke evacuation channel for filtering out debris larger than a predetermined size. The filters may be configured as gratings in the cover.

In some embodiments, a first light source of the plurality of light sources and a second light source of the plurality of light sources direct light at different angles. The angles of the plurality of light sources relative to the blade may be adjustable, and each opening in the cover may be sized to accommodate an adjustable range of angles for the corresponding light source. In certain embodiments, the first light source is angled so as to illuminate an area in front of the retractor and the second light source is angled so as to illuminate an area above the surgical retractor, and the first light source is provided closer to a distal end of the blade than the second light source.

In certain embodiments, the illumination assembly comprises a flexible circuit and at least one power source, and the plurality of light sources are mounted on the flexible circuit and are electrically connected to the at least one power source.

The present invention also provides a retractor comprising: a blade having an upper surface and a lower surface, a handle extending from a proximal end of the blade, and a textured gripping surface formed on at least a portion of one or more of the upper and lower surfaces of the blade, wherein the textured gripping surface includes a non-slip pattern providing a preferential grip in a first direction and minimizing grip in at least a second direction different from the first direction. The textured gripping surface may be formed on a distal tip of the one or more of the upper and lower surfaces of the blade.

In certain embodiments, the non-slip pattern includes a plurality of protrusions inclined so as to provide the preferential grip. Each protrusion may have a pyramid-like shape inclined away from a distal end of the blade and the plurality of protrusions are loosely packed on the textured gripping surface. The distance between adjacent protrusions on the textured gripping surface is greater than each of the width and length of the respective protrusions. In certain embodiments, each protrusion has a substantially triangular cross-section, with a first vertex pointing away from the distal end of the blade and an opposing sidewall between the second and third vertices facing the distal end of the blade, and each protrusion has a flattened top surface.

In some embodiments, each protrusion comprises a rib extending across a portion of the blade's width, each said rib being inclined in a direction away from the distal end of the blade. Each rib may have gradually inclined lateral ends so as to minimize lateral gripping force of the textured gripping surface. The distance between adjacent ribs is greater than a width of each rib.

In certain embodiments, the preferential grip of the non-slip pattern requires a higher force to extract the retractor from a body cavity than a force to insert the retractor into the body cavity. The textured gripping surface may be in-molded onto the one of the upper and lower surfaces of the blade, or may be releasably attached to one of the upper and lower surfaces of the blade. Some embodiments also include a second textured surface different from the textured gripping surface, wherein the textured gripping surface is provided on a distal tip of the blade and the second textured surface is provided on a remaining portion of the blade. The second texture surface may include a plurality of measurement markers indicating a distance from a distal end of the blade.

The present invention further provides a medical device comprising a blade portion, a handle portion extending at an angle from a proximal end of the blade portion, and an illumination assembly having a plurality of light sources mounted on a flexible circuit board, wherein the flexible circuit board extends at least along the length of the blade portion. The medical device may also include a cover attached to the blade portion and configured to enclose the illumination assembly, with the cover including a plurality of openings and each of said openings having a respective light source positioned therein.

In certain embodiments, the flexible circuit board comprises a flexible substrate and a copper layer forming electrical contact paths, with the copper layer covering at least one whole surface of the flexible substrate except for minimum spacing required between electrical contact paths. In some embodiments, the copper layer is provided on both a top and a bottom surface of the flexible circuit board and has a thickness of at least 70 μm. The flexible circuit board may also have a layer of non-conductive material on top of the copper layer for passivating the flexible circuit board.

In certain embodiments, the flexible substrate includes lateral wings extending from each side of the flexible substrate along predetermined portions of the length of the flexible substrate without light sources mounted thereon. The medical device may also include at least one smoke evacuation channel extending along at least a portion of the blade, and smoke evacuation channel overlaps with the lateral wings of the flexible substrate. The medical device may also include a cover configured to enclose the flexible circuit board and having a plurality of openings for exposing therethrough respective light sources mounted on the flexible circuit board. The cover has a plurality of projections adjacent the openings, and the projections retaining the respective light sources. The cover also encloses at least one smoke evacuation channel.

The present invention further provides a battery-operated medical device, comprising a handle coupled to an operative portion, at least one power source housed within the handle, and a push-tab assembly provided in the handle and including a push-tab extending through an opening in the handle, wherein the push-tab is configured to be moved from a first position in which the push-tab prevents flow of electricity from the at least one power source to a second position in which the at least one power source allows flow of electricity from the at least one power source, and wherein in the second position, the push-tab seals the opening in the handle. The medical device may be a surgical retractor or a speculum.

In certain embodiments, in the first position, the push-tab is partially inserted into the opening in the handle and in the second position, the push-tab is fully inserted into the opening so that an outer portion of the push-tab forms an air-tight seal with the handle. The push-tab assembly may include a printed circuit board configured to retain the at least one power source within the handle and including an electrical contact. The electrical contact interacts with the push-tab so that when the push-tab is in the first position, the electrical contact is electrically isolated from the at least one power source and when the push-tab is in the second position, the electrical contact electrically couples with the at least one power source. The electrical contact extends from a surface of the printed circuit board and includes at least one contact portion configured to electrically connect with the at least one power source, and the push-tab comprises at least one electrically insulating leg having an opening therein, the electrically insulating leg being configured to overlap with the at least one contact portion of the electrical contact such that in the first position, the at least one insulating leg electrically isolates the at least one contact portion from the at least one power source and in the second position, the at least one contact portion passes through the opening in the at least one insulating leg to electrically connect to the at least one power source. In some embodiments, the at least one contact portion of the electrical contact is biased towards the at least one power source.

In some embodiments, the printed circuit board is configured to retain and electrically connect to a first power source and a second power source and the electrical contact extends from a surface of the printed circuit board between the first and second power sources, the electrical contact includes a first contact portion biased toward the first power source and a second contact portion biased toward the second power source, and the push-tab comprises a pair of electrically insulating legs each having an opening therein, the electrically insulating legs being configured to overlay the electrical contact so that in the first position of the push-tab, a first insulating leg is positioned to electrically isolate the first contact portion from the first power source and a second insulating leg is positioned to electrically isolate the second contact portion from the second power source, and in the second position of the push-tab, the first contact portion protrudes through the opening in the first insulating leg to electrically connect with the first power source and the second contact portion protrudes through the opening in the second insulating leg to electrically connect with the second power source.

In certain embodiments, the handle includes a cover configured to be opened to expose the at least one power source and including the opening for accommodating the push-tab. When the push-tab is in the second position, the push-tab engages with the at least one power source so that upon opening the cover, the push-tab causes the at least one power source to be removed from the handle without requiring the user to come into contact with the at least one power source. In some embodiments, the push-tab comprises at least one electrically insulating leg having an opening therein, the electrically insulating leg being configured to overlap with the at least one contact portion of the electrical contact such that in the first position, the at least one insulating leg electrically isolates the at least one contact portion from the at least one power source and in the second position, a terminal of the at least one power source engages with the opening in a respective electrically insulating leg and electrically connects with a respective contact portion. In the second position, the terminal of the at least one power source passes through the opening in the respective electrically insulating leg.

In another aspect of the present invention, a surgical retractor is provided that includes a blade, a handle extending at an angle from the blade portion, an illumination assembly comprising one or more light sources provided on the blade, a smoke evacuation assembly coupled to a vacuum source, and a controller for controlling operation of the at least one of the illumination assembly and the smoke evacuation assembly, wherein a distal end of the handle portion extends into a curved section offset from a central plane of the handle, and wherein the curved section accommodates the controller such that the controller is offset from the central plane of the handle. The controller may include one or more operating members for controlling one or more of activation of the one or more light sources, brightness of the one or more light sources and hue of the one or more light sources.

In certain embodiments, the curved section curves in the same direction as the direction of the blade, and the operating members are provided on a convex surface of the curved section. The controller may be positioned on the curved section such that when the handle is gripped by a user, the controller is reachable by the user's thumb from the gripped position. In some embodiments, the smoke evacuation assembly includes one or more tubes for conveying smoke, fluids and debris away from an operating site, and the one or more tubes extends along a portion of the blade to the curved section. The curved section may include internal projections configured to accommodate the one or more tubes and to form a sealed chamber in the curved section for receiving smoke, fluids and debris from the one or more tubes and for coupling with the vacuum source.

BRIEF DESCRIPTION OF THE DRAWINGS

The above and other features and aspects of the present invention will become more apparent upon reading the following detailed description in conjunction with the accompanying drawings, in which:

FIGS. 6A and 6B show an exemplary variation of the retractor of FIGS. 1A-C with multiple light sources;

FIG. 15A shows an LED flex circuit of the retractor of FIGS. 14A-D;

FIGS. 15B-15C show a modified LED flex circuit with improved thermal dissipation;

FIG. 15D shows a table with exemplary characteristics of various layers of the LED flex circuit of FIGS. 15A-C;

DETAILED DESCRIPTION

Figure 1C:
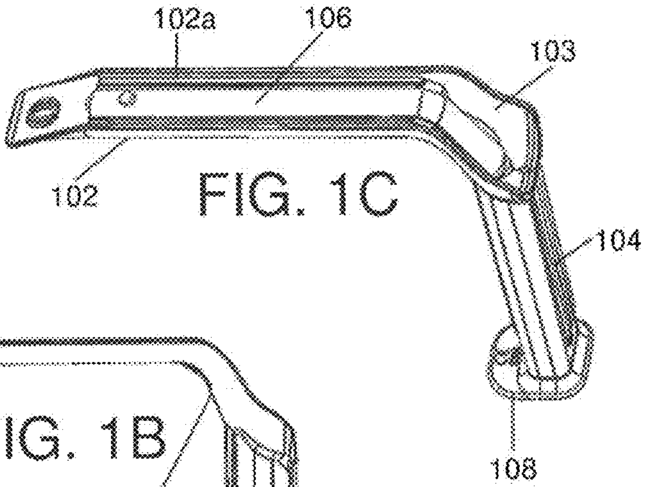
FIGS. 1A-1C show views of a retractor with multiple light sources in accordance with a first embodiment of the present invention.

It is noted that embodiments described herein relate to various features of an illuminated medical device, such as a surgical retractor. While some of these features are described from the perspective of being embodied within a retractor, such illustration is not intended to limit the scope of the present invention. Other medical devices such as a vaginal speculum, a laryngoscope, an anoscope, etc. may also fully embody the features described herein. For example, a vaginal speculum may embody the features of the present invention relating to an illumination assembly having multiple light sources, such as LEDs, that are particularly configured to maximize illumination while minimizing obstruction of the physician's field of view. As another example, an illuminated laryngoscope may incorporate the features of the present invention relating to removal of batteries and disposability of the device. These examples are not intended to limit the full scope of the present invention, and the various medical devices may include one or more of the features described herein below.

The illuminated medical device of the present invention includes multiple features, which may be used in different devices and in different versions of the medical devices. These features include multiple LED illumination and control thereof, a textured non-slip pattern applied to a blade, an ergonomic handle, a smoke evacuation system integrated with an LED flex circuit for illumination, an improved coupling between the blade and a blade cover, a modified LED flex circuit for improved thermal dissipation, a push-tab assembly for safe transport of battery-powered devices and for easy battery removal from medical devices, and an improved handle end assembly that improves smoke, fluid and debris removal from the handle. These features are described with reference to particular embodiments of a surgical retractor shown in the drawings. However, these features may be incorporated in each of the embodiments or variations of the retractor or may be selectively incorporated in the different variations of the retractor. Moreover, as mentioned herein above, these features may be used in other types of medical devices. The features of the illuminated medical devices will now be described in detail.

Multiple LED Illumination

Figure 1B:
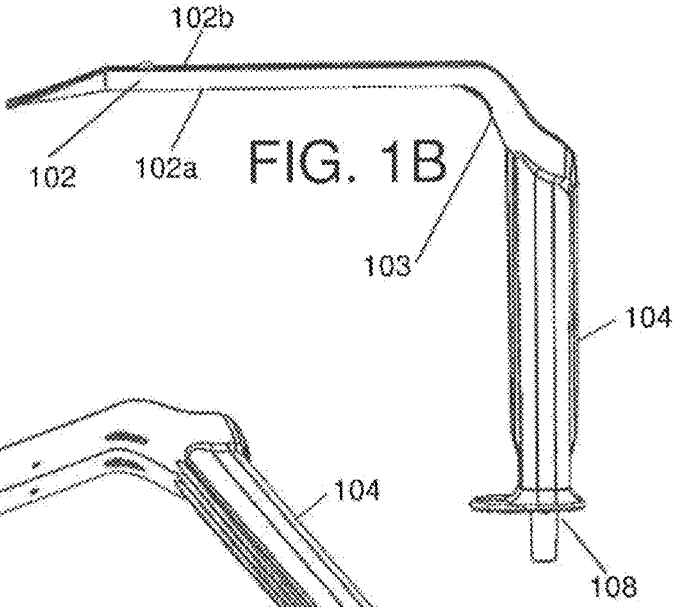
Figure 1A:
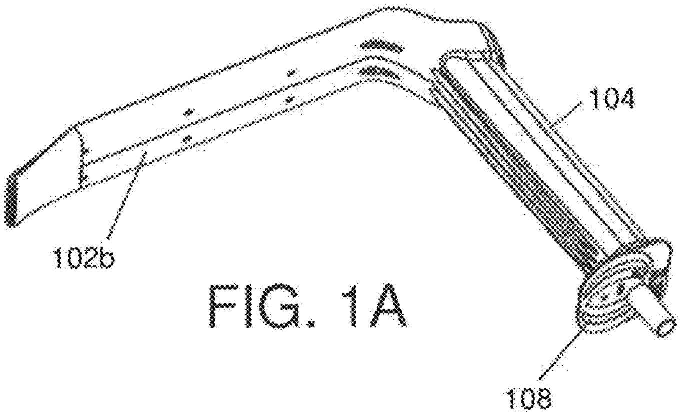

Referring to the drawings, FIGS. 1A-1C thereof show different views of a retractor 100 in accordance with a first embodiment of the present invention. As shown in these figures, the retractor 100 includes a blade portion 102 having a first (bottom) surface 102*a* and an opposing second (bottom) surface 102*b* and a proximal end and a distal end. The proximal end is defined herein as the end of the blade portion closer to a handle of the retractor and the distal end is defined as the tip end of the blade portion opposing the proximal end. The retractor 100 further includes a handle portion 104 that extends from the blade portion 102 at an angle. In this illustrative embodiment, the handle portion 104 is generally perpendicularly joined to the blade portion at the proximal end of the blade portion. In some versions, the angle may vary, for example, at 95°, 100°, 105°, etc., without limiting the scope of the present embodiment. The portion of the retractor 100 where the blade portion 102 and the handle portion 104 are joined is referred to herein as a curved portion 103 or a saddle portion 103.

The retractor 100 further includes a smoke evacuation channel formed by a cover 106 that runs along the length of the blade portion 102 to the handle portion 104 and may be in fluid communication with an end cap assembly 108 at a distal end of the handle portion 104. The cover 106 may have an arc shape, semi-circular shape, rectangular shape, or other suitable shape or size appropriate for carrying out the function of evacuating smoke or debris generated near the distal end of the retractor 100 to the end cap assembly 108. In the version shown in FIGS. 1A-C, the end cap assembly 108 is provided with a vacuum port which can be attached to a vacuum source and is in fluid communication with the smoke evacuation channel. In other variations, the vacuum port may be provided in other areas of the handle portion, such as near the proximal end of the handle portion, instead of in the end cap assembly. The smoke evacuation channel serves as an air conduit to direct smoke, fumes and/or debris from the distal end of the blade portion, through the length of the retractor, and out the end cap assembly 108 at the bottom of the handle portion 104. As mentioned above, the end cap assembly 108 can be coupled with a vacuum source to suck the smoke, fumes and/or debris via the smoke evacuation channel.

Figure 2:
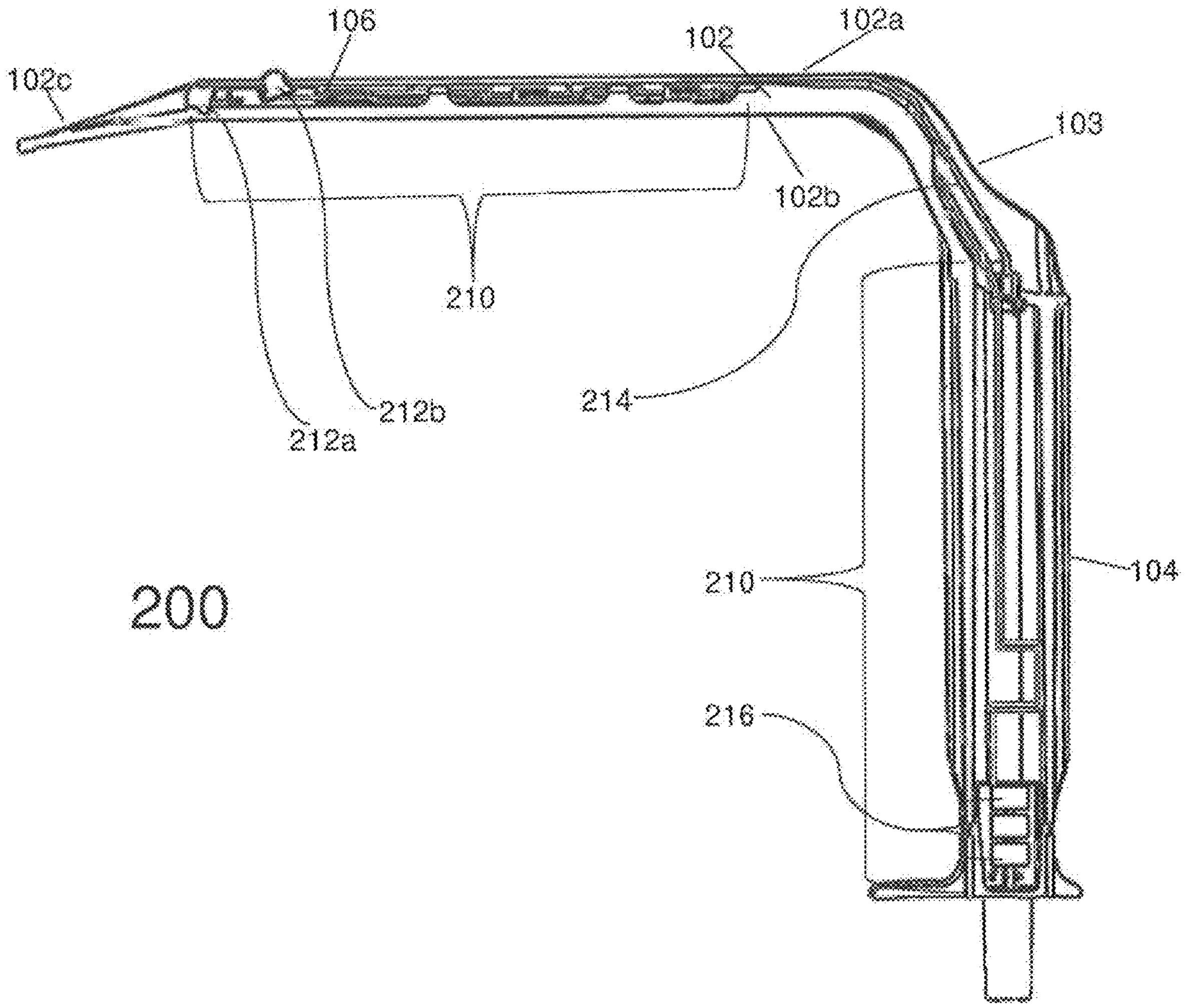
FIG. 2 shows a cutaway view of the retractor of FIGS. 1A-C.

As shown in FIG. 1C, the smoke evacuation channel cover 106 is coupled to the top surface 102*a* of the blade portion 102 and extends at an angle along the surface of the saddle portion 103. As shown in FIG. 2, the handle portion 104 has a hollow interior. In some illustrative versions, the smoke evacuation channel cover 106 opens at one end into an opening formed at the proximal end of the handle portion. In other illustrative versions, the smoke evacuation channel cover 106 may be coupled with the handle portion 104 or may extend into the opening formed at the end of the handle portion 104. In yet other versions, the handle portion 104 may include an internal channel in fluid communication with the smoke evacuation channel cover 106. In certain versions, the smoke evacuation channel cover 106 is permanently attached to at least the blade portion. The attachment between the cover 106 and the blade portion 102 may be achieved by any suitable means. In one illustrative version, the cover 106 is provided with engagement tabs and the blade portion includes corresponding slots, visible in FIG. 1A, wherein the engagement tabs on the cover 106 are received by and engaged with the corresponding slots in the blade portion. A more detailed description of the engagement tabs and corresponding slots is provided in U.S. Pat. No. 9,867,602 and in U.S. Published Application No. 2017/0245849, both assigned to the same assignee herein, and incorporated herein by reference.

Additional details as to the structural aspects of the blade portion, the handle portion, and the smoke evacuation channel can be found in U.S. Published Application No. 2016/0354072, titled "RETRACTOR", the entire content of which is incorporated herein by reference. Therefore, additional descriptions of these elements will be omitted for sake of brevity.

The present embodiment focuses on the specifics and the novel characteristics relating to an illumination assembly that includes a plurality of light sources, and particularly, on positioning and configuration of the multiple light sources of the illumination assembly. Although the embodiments of the present invention are described with reference to a retractor fully incorporating the structural features described above, such descriptions are not intended to limit the scope of the present invention. As such, the techniques and the features of the illumination assembly as described and illustrated herein may be implemented with various retractor designs, or with other illuminated medical devices, that are currently available on the market without departing from the scope and spirit of the present invention. For example, the inclusion or exclusion of a smoke evacuation channel does not limit the scope of the present invention. As another example, the particular shape of the retractor blade or the manner in which the blade is coupled to the handle of the retractor does not limit the scope of the present invention.

Referring back to the drawings, FIG. 2 thereof shows a cutaway view of a retractor 200 in accordance with the first embodiment of the present invention. In particular, the retractor 200 includes an illumination assembly 210 that extends along the lengths of the blade portion and also the handle portion. More specifically, the illumination assembly 210 includes at least a first light source 212*a*, a second light source 212*b*, a power source, such as batteries 216, and wires or connections 214 coupling the light sources 212*a*, 212*b* with the batteries 216. The first and second light sources 212*a* and 212*b* are connected to the batteries 216 via the wires 214 which run along the length of the retractor. Although not shown, the illumination assembly 210 may further include one or more switches or activation devices to selectively control energization of the light sources. The activation device may be a depressible switch, a rotatable switch, a flickable switch, a slidable switch, a removable pull tab, a touch button, a lever, a multi-directional switch, a motion detection assembly, etc. or a combination thereof.

The positioning of the batteries 216 as shown in FIG. 2 is also not intended to be limiting. In fact, the positioning of the batteries, and therefore, the configuration of the one or more wires to connect the light sources to the batteries may vary without departing from the scope of the present invention. For example, the batteries may be disposed adjacent to the saddle portion 103, on or at least partly on the saddle portion 103, or may be disposed at a different position within the handle portion 104. As another example, the batteries, or at least a portion of the batteries, may be contained within a battery compartment that is placed externally, or at least partly externally, to the handle portion 104 and otherwise attached to an external surface of the handle portion 104 or at another location on the retractor 200. In yet another example, the batteries may be provided on or attached to the blade portion of the retractor, on either the same surface of the blade as the smoke evacuation cover 106 or the opposing surface of the blade.

FIG. 2 illustrates a specific configuration of the first light source 212*a* and the second light source 212*b*, and the other portions of the illumination assembly, which is integrated with the smoke evacuation channel and its cover 106. The first light source 212*a* is provided at an opening formed at the end of the smoke evacuation channel cover 106, and the first light source 212*a* is partially enclosed by the end of the smoke evacuation channel cover 106. In another version, the first light source 212*a* is completely outside of, preferably near, the smoke evacuation channel cover 106. The first light source 212*a* is angled relative to the blade portion 102 at a first angle, so that light emitted from the first light source 212*a* is directed more toward illuminating an area near or in front of the distal end of the retractor blade portion 102. In this illustrative version, the blade portion 102 includes a tip 102*c*, which is angled relative to the main portion of the blade 102. The first light source 212*a* is positioned at or near the border between the main portion of the blade 102 and the angled tip 102*c*, and is angled relative to the main portion of the blade 102 in a direction away from the tip 102*c*. In other versions, the tip of the blade portion 102 may be aligned with the main portion of the blade, and not angled with respect thereto, and the first light source 212*a* may be provided near the distal end of the tip or may be provided at a predetermined distance away from the distal end of the tip. In such versions, even when a portion of the distal end of the tip 102*c* is inserted within a subject's body, the first light source 212*a* remains external to the bodily opening. In certain other versions, the tip 102*c* is angled relative to the main portion of the blade 102 and the first light source 212*a* is parallel to the angled tip 102*c*. In yet certain other versions, regardless of the relative angle between the tip 102*c* and the main portion of the blade 102, the first light source 212*a* is angled to focus its illumination directly to the incision site.

As shown in FIG. 2, the second light source 212*b* is provided at a distance away from the first light source 212*a* closer to the proximal end of the blade portion. The second light source 212*b* extends and/or protrudes through an opening formed in the smoke evacuation channel cover 106. The second light source 212*b* is also angled relative to the blade portion 102 at a second angle which is different from the first angle, so that the light emitted by the second light source 212*b* is directed at a different angle and more toward an area outside the first surface 102*a* of the blade 102. In some versions, the first light source 212*a* may be at an angle between 0° and 30° with respect to the horizontal plane of the main portion of the retractor blade, and the second light source 212*b* may be at an angle between 60° and 90° with respect to the same horizontal plane. For instance, the first light source 212*a* may be at an angle of 15° with respect to the horizontal plane of the main portion of the retractor blade and the second light source 212*b* may be at an angle of 70° with respect to the same plane. In other versions, the first light source 212*a* may be aligned with respect to the horizontal plane of the main portion of the blade, i.e., angle of 0°, while the second light source 212*b* is perpendicular to the same plane, i.e., angle of 90°. In yet another version, the first light source 212*a* may be at a 25° or 30° angle with respect to the horizontal plane of the blade, while the second light source 212*a* is angled at a 60° or 65° angle with respect to the same plane. However, the specific angles of the first and second light sources 212*a*, 212*b* may vary depending on the configuration and purpose of the retractor. Moreover, in some versions, the angles of the light sources may be manually adjustable by the user of the retractor by directly adjusting the angles of the respective light sources or via a control system so as to provide greater flexibility. For instance, one or more of the light sources can be mounted on the blade portion or within the smoke evacuation channel cover 106, so as to allow for rotation or movement of the light source relative to the blade portion. In such versions, the size of the respective opening formed in the smoke evacuation channel cover is configured accordingly so as to accommodate the adjustable or rotatable range of the one or more light sources and/or to limit the range of adjustment or rotation of the one or more light sources. In some versions, the light sources may be mounted on the blade portion or within the smoke evacuation channel cover 106 so as to allow for adjustment or movement of the light source to one or more predetermined positions or steps and to allow for locking of the position of the light source at the one or more predetermined positions or steps relative to the blade and/or cover 106.

In some versions, the smoke evacuation channel cover 106 includes one or more openings for the second light source and/or other light sources, and each of the one or more openings is sized larger than the corresponding light source so as to allow the light source to be moved within the opening to adjust its position relative to the cover 106. In other versions, the smoke evacuation channel cover 106 includes two cover portions provided in an overlapping relationship with one another and allowing one of the cover portions to move relative to the other cover portion. For example, the cover 106 shown in FIGS. 1C, 5, 6A and 6B may be formed as an inner cover portion that includes one or more openings sized larger than the corresponding light source(s) and allowing the light source(s) to move within their respective opening(s) for adjusting their position(s). In this example, the cover may also include an outer cover portion slidably engaged with the inner cover portion or with the blade so that the outer cover portion can slide or move relative to the inner cover portion. The outer cover portion includes one or more openings corresponding to the light source(s) and sized smaller than the openings in the inner cover portion. Preferably, the opening(s) in the outer cover are sized similarly to the outer periphery of the corresponding light source(s). In this configuration, when the position of the light source(s) is adjusted, the outer cover and the opening(s) in the outer cover move together with the light source(s) being adjusted so as to reduce the size of any gaps formed between the light source and the cover and to avoid air leaks through the larger sized openings in the inner cover portion. In some variations, a separate outer cover portion may be provided for each light source whose position is adjustable, with each outer cover portion being sized so as to cover at least the corresponding larger opening formed in the inner cover portion. In yet other variations, the inner cover portion may have a single elongated opening in which one or more light sources are movably provided. In further variations, the configurations of the inner and outer cover portions may be reversed, so that the outer cover portion has larger sized opening(s) and the inner cover portion is slidably engaged with the outer cover portion and has corresponding smaller sized opening(s). Other variations of these structures are contemplated by this invention.

Figure 3:
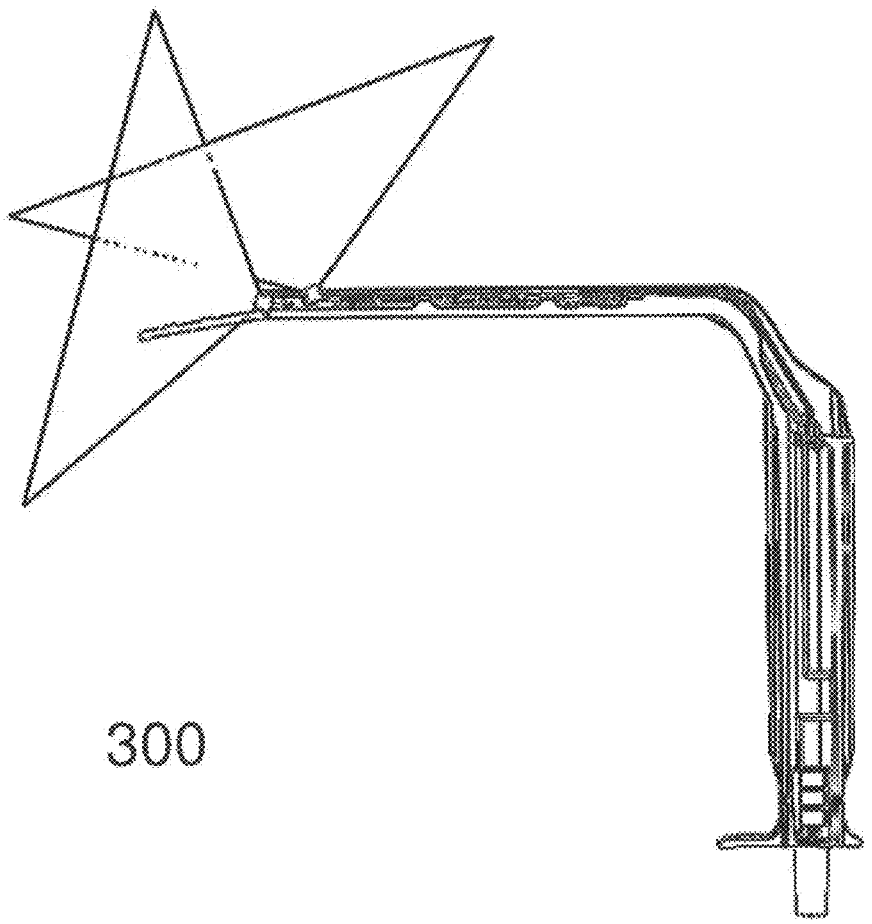
FIG. 3 shows another cutaway view of the retractor of FIGS. 1A-C and illustrates the angles for the first and second light sources of the retractor.

As further illustrated in FIG. 3, the angles for the first and the second light sources are chosen so that light projections resulting from the light sources illuminate both the area near the distal end of the retractor blade portion 102 and the area above the retractor blade portion or around the first surface 102*a* of the blade surface. Preferably, the light sources are configured to not direct light back toward the user. However, a small or negligible amount of light directed back to the user may be acceptable in certain applications. Accordingly, the angle and position of the first light source 212*a* with respect to the retractor handle and the angle and position of the second light source 212*b* with respect to the retractor handle, as well as the distance between the first light source 212*a* and the second light source 212*b*, may vary within a range of angles, positions and distances as long as the light from either of the first light source 212*a* and the second light source 212*b* (preferably) is not directed back toward the user. For example, given a range of light projection for a light source, the angle of the light source with respect to the horizontal plane of the retractor blade may need to be decreased as the light source is positioned closer to the proximal end of the retractor blade if it is desired for the light emitted from the slight source to be directed more toward the distal end of the blade.

Figure 4:
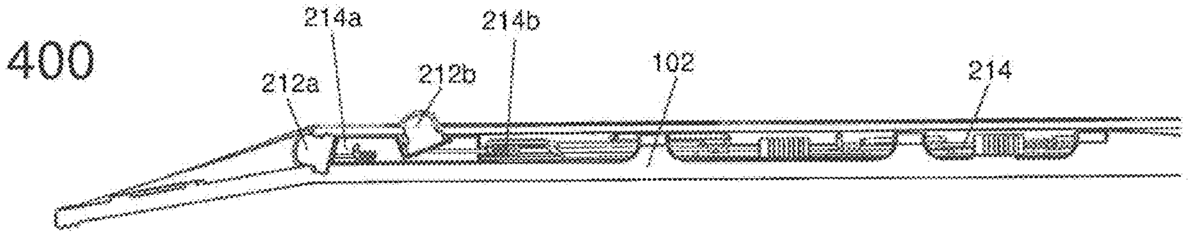
FIG. 4 illustrates a close-up cross-sectional view of the retractor blade portion of FIG. 2.

FIG. 4 illustrates a close-up cross-sectional view of the retractor blade portion 102 of FIG. 2 showing the first light source 212*a*, the second light source 212*b*, the angle of the first light source, the angle of the second light source and various other circuitry elements such as wires 214, current limiting resistors 214*a*, etc. that are electrically coupled to the light sources. As shown, each of the light sources 212*a*, 212*b* is coupled to at least one current limiting resistor 214*a*, 214*b* that controls the amount of current supplied to the light source 212*a*, 212*b*. The light sources 212*a*, 212*b* are electrically coupled to the power source, i.e., one or more batteries, using wires via the current limiting resistor(s) 214*a*. It is appreciated that various light sources that can be used within the present invention may not require the use of current limiting resistors.

In certain versions, the blade portion may include substantially parallel guides, formed as a pair of protrusions on its surface, for holding the wires and/or resistors in place under the smoke evacuation channel cover 106. An example of such guides is disclosed in U.S. Published Application No. 2017/0245849, assigned to the same assignee herein and incorporated herein by reference. It is understood that this type of an arrangement and circuitry can be used for the retractor shown in FIGS. 1-3 with two light sources and can also be adapted for use in retractors with additional light sources, such as the retractor shown in FIG. 6.

In one version, when a plurality of light sources is used in the retractor, the light sources are uniformly spaced along the blade portion to evenly illuminate the areas in front of and above the retractor blade. In another version, the light sources may be more concentrated toward the area desired for higher illumination. For example, two or more light sources may be positioned close together near the distal end of the blade portion and one or more additional light sources may be positioned near the proximal end of the blade portion.

Different types of light sources may be used within the same device. For instance, light sources with different brightness levels may be employed. In one version, light sources having a higher brightness may be positioned near the distal end of the blade portion and light sources having a lower brightness may be positioned near the proximal end of the blade portion, or vice versa. In a further version, light sources with different luminosity, intensity, color, frequency, etc., may be employed within the same device to suit various needs.

The light sources may also be individually replaceable or interchangeable. In other versions, the light sources may be movable (e.g., shiftable) with respect to their positions on the retractor blade and/or rotatable so that the respective angles for each individual light source is adjustable. In any of versions described herein, the light sources may be activated (i.e., turned on) in a variety of manners via the use of a single switch, multiple switches (each switch controlling a respective light source), or other appropriate activation mechanisms. In yet other versions, a controller or other type of device (either via hardware, software or a combination of hardware and software) is employed to cause the activation of selected light sources (e.g., one, multiple or all of the light sources). For instance, a push-button type device may be employed to control all of the light sources, whereupon a single depression of the push-button causes a first light to activate, a second depression of the push-button causes only a second light to activate (with the first light turning off), and so on, and then yet subsequent depressions of the push-button causes various multiple lights to activate. In such an arrangement, a single switch can be used to particularly select the desired combination of lights to activate. Other variations of cycling through the lights may be employed.

Moreover, different types of switches may be employed. Still further, in yet other versions, the brightness level(s) of one or more light sources is controllable via one or more appropriate devices (e.g., a potentiometer). Push-buttons or other types of activation mechanisms similarly may be employed to cycle through different levels of brightness of one, multiple or all of the light sources. For instance, a single switch (or other appropriate device) can control the brightness level of all of the light sources. Or, in a variation, each light source is separately controlled via a respective switch.

In each of the versions and variations described herein, the positions, angles, and movement of such positions and/or angles (in certain versions) of the light sources, along with differences, if any, (in certain versions) of the lighting characteristics of the various light sources (e.g., brightness level), and other features described herein, provide illuminated retractors in accordance with the present invention that result in a highly desirable and advantageous lighting effect.

Figure 5:
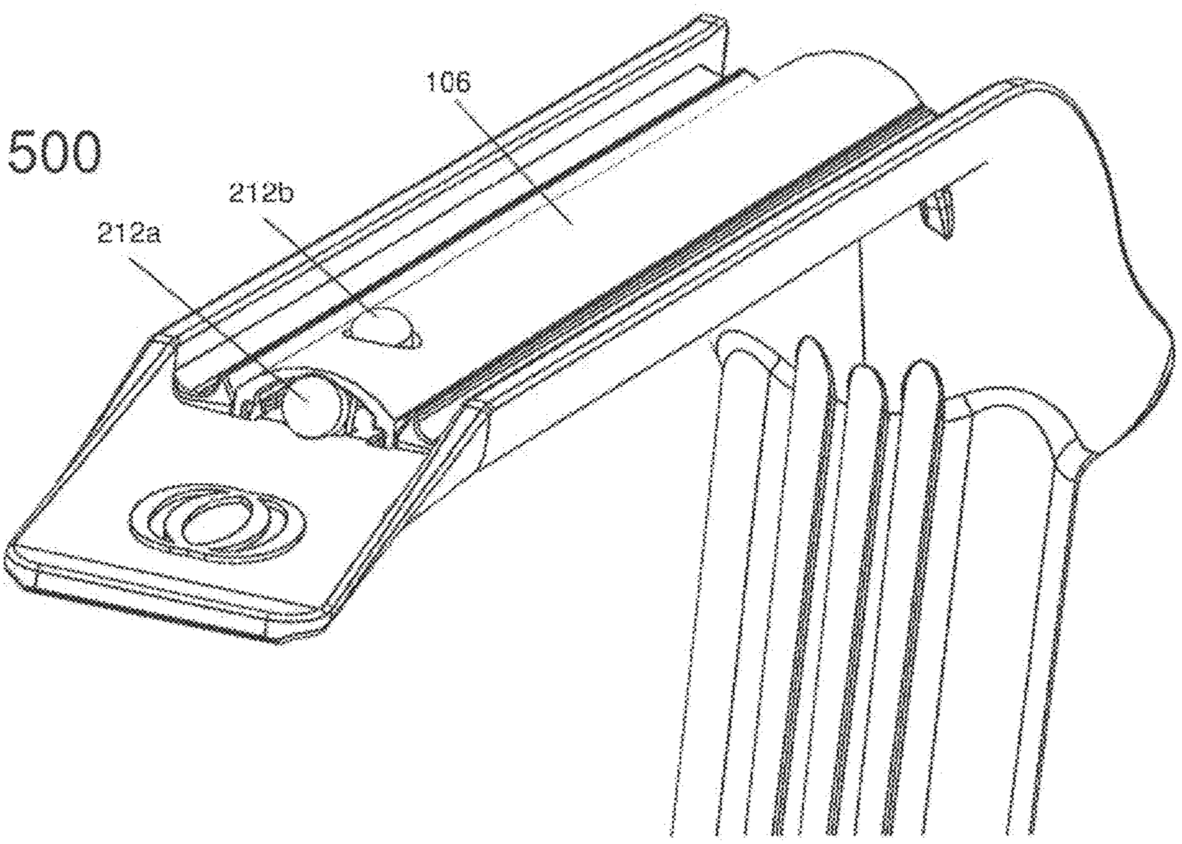
FIG. 5 illustrates a close-up view of the retractor blade of the retractor of FIG. 2.

FIG. 5 illustrates a close-up view of the retractor blade of the present invention illustrating the illumination assembly being enclosed by the smoke evacuation channel 106*a*. As shown, the first light source 212*a* is positioned within an opening of the smoke evacuation channel cover 106 formed at the distal end of the cover 106. In this illustrative version, the first light source 212*a* is appropriately sized so as not to completely block the opening of the smoke evacuation channel formed by the cover 106. The second light source 212*b* and other additional light source(s) may be positioned appropriately throughout the retractor blade and the smoke evacuation channel may be designed accordingly to accommodate each additional light source. In some versions, the additional light sources are partially enclosed by an opaque smoke evacuation channel cover 106 such that the smoke evacuation channel blocks some of the light directed back toward the user. As shown in FIG. 5 and described above, the second light source 212*b* extends through an opening formed in the cover 106. Additional openings in the smoke evacuation cover 106 may be provided for additional light sources. By incorporating the light sources of the illumination assembly into the smoke evacuation channel and its cover 106, the retractor of the present invention has a compact construction, wherein the wiring for the light sources is hidden by the smoke evacuation channel cover 106 and the size and thickness of the retractor is not increased.

As mentioned above, in another variation, additional LEDs can be added to the surface of the retractor blade to illuminate areas closer to the handle as illustrated in FIGS. 6A and 6B. FIGS. 6A and 6B show another exemplary variation of the present embodiment in which four light sources are positioned along the blade portion of the retractor 600. As shown in these drawings, a first light source 612*a* is positioned near the distal end of the blade portion, which also corresponds to an opening formed at the end of a smoke evacuation channel cover 606. Similar to prior versions described herein, the first light source 612*a* is angled at a first angle such that the first light source 612*a* illuminates an area near the distal end of the retractor 600. An exemplary angle may be 10° with respect to the horizontal plane of the blade portion. An exemplary range of the angle of the first light source 612*a* relative to the horizontal plane of the blade portion may be between 0 and 25 degrees. However, the angle of the first light source 612*a* may vary depending on the construction of the retractor 600, the distance of the first light source 612*a* away from the distal end of the retractor 600 and other factors.

A second light source 612*b*, a third light source 612*c* and a fourth light source 612*d* are provided along the length of the blade portion. As shown in these drawings, the smoke evacuation channel cover 606 includes a plurality of openings, each of which is aligned with a respective light source. In the exemplary version illustrated in FIGS. 6A and 6B, the second light source 612*b*, the third light source 612*c* and the fourth light source 612*d* are evenly spaced apart and are angled at approximately the same second angle. In this configuration, these light sources, in combination, provide illumination to a large area above the retractor blade. In other variations, the angles of the second, third and fourth light sources 612*b*-612*d* may be different from one another. In yet other variations, the spacing between the light sources may be varied. For example, the second and third light sources may be closer together toward the distal end of the blade portion and the fourth light source may be closer to the proximal end of the blade portion. In this version, a greater illumination is provided closer to the incision site and additional illumination is provided closer to the user of the retractor. The positioning of the second, third and fourth light sources may be varied depending on the desired illumination and the use of the retractor. In this exemplary version or in any other versions of the present invention, the fourth light source 612*d* (or the light source placed closest to the proximal end of the blade portion) is positioned such that the light projection from such light source is not directed back toward the user's eyes.

In certain versions, the positions and the angles of the plurality of light sources may be defined by a mathematical relationship. For example, as the light source is placed closer to the proximal end of the blade portion, the tilt angle of the light source with respect to the horizontal plane of the blade portion may decrease linearly. For example, with respect to FIG. 6A, since the second, third and fourth light sources are evenly spaced along the blade portion, the second light source 612*b* may be configured at an angle 75° with respect to the horizontal plane, the third light source 612*c* may be configured at an angle 50° with respect to the horizontal plane and the fourth light source 612*d* may be configured at an angle 25° with respect to the horizontal plane. The linear relationship reflects the effect that the smaller the angle becomes with respect to the horizontal plane of the blade portion, the more the light is directed toward the distal end of the blade portion and away from the user's eyes. Such gradual decrease in angle prevents the light sources placed closer to the proximal end of the blade portion from creating a back light or glare to the user.

These mathematical relationships with respect to tilt angles are exemplary only and different mathematical relationships may be employed with other the tilt angles, and also with respect to other characteristics of the light source such as brightness, frequency, etc.

In accordance with various versions of the present embodiment, the additional LEDs are preferably angled so as to not to direct light back to the user. In one version, the suitable angle configurations for the one or more light sources may depend on the specific type of the light source. For example, it has been experimentally determined that a light projection cone for an LED light source covers approximately 110°. Accordingly, as the position of the LED light source (or any other types of light source) approaches closer to the proximal end of the blade portion, the angle of the LED is controlled appropriately to prevent creating back light or a glare to the user. As in the above-described versions and variations, the angles of the respective light sources in the FIGS. 6A-6B and, in other configurations of retractors with a different number of light sources, may all be adjustable by the user, either manually or through a control mechanism. The adjustability of the angles of the light sources provides more flexibility in the way that the light may be directed to the areas where illumination is needed or desired.

Figure 7:
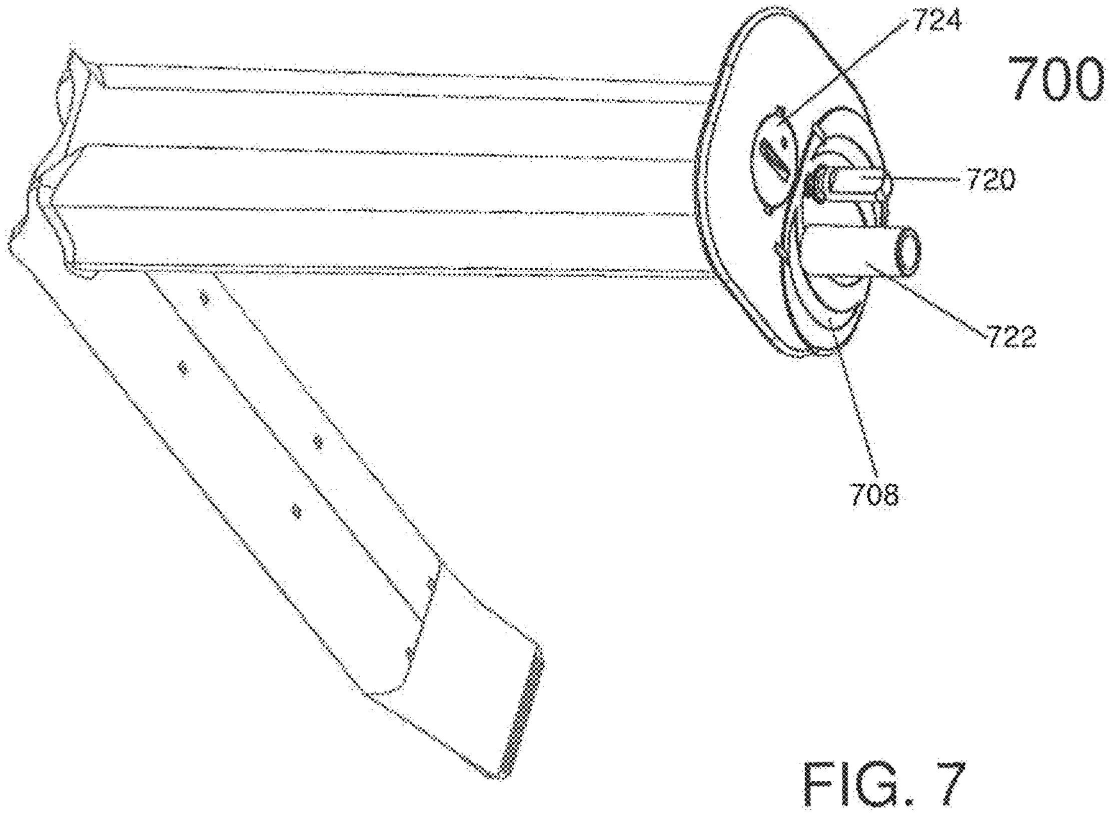
FIG. 7 illustrates an exemplary retractor end cap assembly for use with retractors of the present invention.

FIG. 7 illustrates an exemplary retractor end cap assembly 708 for use with any of the above-described and other versions of the present embodiment. As shown in FIG. 7, a retractor 700 receives the end cap assembly 708, which in some embodiments is partially inserted into the distal end of the retractor handle, which is open. The end cap assembly 708 includes a controller 720 and a smoke evacuation port 722 adapted for coupling to a vacuum source. An internal construction of an end cap assembly configuration, which may be used in the present embodiment, is described in U.S. Published Application No. 2017/0245849 and U.S. application Ser. No. 15/869,994, both assigned to the same assignee herein and incorporated herein by reference. Although in the version shown in FIG. 7, the smoke evacuation port 722 and the controller 720 are assembled as part of the end cap assembly, in other versions, either the smoke evacuation port 722 or the controller 720 can be separately configured. For example, the controller 720 may be provided on or near the distal end of the handle portion of the retractor or closer to the blade portion of the retractor.

As also visible from FIG. 7, the end cap assembly 708 includes a removable or releasable battery door 724, which holds the batteries within the end cap assembly 708 and which may be opened for removal and disposal/recycling of the batteries. The illustrative battery door 724 shown in FIG. 7 is inserted into an opening in an outer wall of the end cap assembly and rotated or screwed in to lock the battery door 724 relative to the outer wall and to hold the batteries within the end cap assembly 708. The battery door 724 can be opened by rotating the battery door 724 relative to the outer wall of the end cap assembly 708 from the locked position to an unlocked position and removed in order to release the batteries via the opening in the outer wall of the end cap assembly. In other embodiments, other locking mechanisms may be used for locking and unlocking the battery door, including but not limited to retractable tabs on the battery door that engage with the outer wall of the end cap assembly, a latch mechanism or a push open mechanism. In some embodiments, the battery door may be hinged to the outer wall of the end cap assembly so that when the battery door is opened, it does not fully separate from the end cap assembly and is not completely removed therefrom.

In accordance with the illustrative embodiment of the end cap assembly of FIG. 7, when the smoke evacuation port 722 (also referred to herein as a vacuum port) is coupled with a vacuum source, smoke, fumes and/or debris are sucked in through the smoke evacuation assembly from the distal end of the blade portion, through a smoke evacuation channel stretching over the length of the retractor, and out the end cap assembly 108 via the smoke evacuation port 722. In some embodiments, the smoke evacuation channel is formed by the blade and the channel cover as described above, and has an open end at or near the distal end of the blade and an opposing end that opens into the handle, which has a hollow construction. In such embodiments, the smoke, fumes and/or debris are sucked into the smoke evacuation channel formed by the blade and the cover thereon, and are thereafter conveyed through the hollow handle to the smoke evacuation port 722 in the end cap assembly. In other embodiments, the smoke evacuation channel formed by the blade and the channel cover is fluidly coupled to a separately defined channel within the handle that connects to the smoke evacuation port 722 in the end cap assembly.

In this illustrative version, the controller 720, as illustrated in FIG. 7, is a potentiometer that can be activated, such as by turning, sliding, pushing, clicking, etc., to control the light sources, such as to adjust the brightness of the light sources. In the illustrative example in FIG. 7, turning the potentiometer one way (e.g., clockwise) gradually dims the brightness of the light sources and turning the potentiometer the other way (e.g., counter-clockwise) gradually increases the brightness of the light sources. In certain versions, the potentiometer can also be configured to execute a separate function by pushing so as to activate a pushbutton. For example, pushing in or pressing on the potentiometer can activate a series of sequences that are stepped through each time the potentiometer is depressed. For example, the first part of the sequence can be to turn all of the light sources off. The next part of the sequence can be to turn on only the front or forward facing light source near the distal end of the blade. The next part of the sequence can be to turn on the front light source and the rest of the light sources. Alternatively, the next part(s) of the sequence can be to turn on the front light source and the next light source adjacent to the front light source, and with the next push(es) on the potentiometer to turn on the next adjacent light source until all of the light sources are turned on. The last part of the sequence can be to turn off the front light source while keeping the other light sources on. When the potentiometer is pushed in again, the sequence can be repeated as all light sources are turned off. The sequence of turning on and off the light sources is not limited to the specific sequence described and the parts of the sequence may be varied. For example, the order of the sequence may be configured in any way, some parts of the sequence may be omitted, or additional steps may be added to the sequence for individually controlling turning on and off the light sources so as to provide the most flexibility.

The above described sequences can be especially useful when three or more light sources are configured on a retractor in accordance with the present invention. For instance, during a medical procedure, when such retractor is used, there is a period of time when a portion of the distal end (including the front facing light source) of the retractor is inside the patient. During this circumstance, any light source toward the proximal end of the retractor blade would be outside the patient and would provide illumination outside the patient's entry point. Any illumination outside the entry point can be objectionable to the physician as it hampers the human eye's ability to see when a darker area is beyond a bright area. Thus, in this situation, the controller would be used to turn on the first light source and/or the second light source located near the distal end of the blade and to turn off or keep off the third and/or fourth light sources located closer to the proximal end of the blade.

Since there is very limited space on the end cap assembly of the retractor, and this space is ideal for any illumination controls and suction hookup, it is important that this space is used efficiently. Combining a pushbutton switch with a potentiometer, as described above, very efficiently utilizes the space on the end cap assembly.

In another illustrative version, the controller 720 may function as a multi-directional switch, such as a two-directional or a four-directional lever switch, wherein a user can push or pull the lever to one of the different directions. In some versions, operation or activation of the controller 720 in each direction may correspond to controlling a different respective light source and may adjust the turning on/off of the respective light source and/or may adjust the brightness of the respective light source and/or may adjust the angle of the respective light source. For example, operation of the lever switch in a first direction, e.g., up direction, can cause a front light source to turn on with a predetermined brightness and subsequent operations of the lever switch in the first directions can cause the brightness of the front light source to be adjusted, e.g., make the front light source brighter or dimmer, in predetermined steps. In certain versions, each direction of the lever controller 720 may correspond to a different function, such as turning on/off the light sources in a certain sequence, adjusting the brightness of the light source(s), adjusting the color of the light source(s), adjusting an angle of the light source(s), etc. The number of directions in which the controller can be operated is not limited to four and can be any suitable number.

In certain versions of the present embodiment, the controller is shaped and designed as a knob to operate as a multi-directional lever to allow users to use their thumb to (1) depress the controller, (2) push/pull the controller and/or (3) to rotate the knob. Different operations (1)-(3) may be used or assigned to different functionalities. For example, operation (1) may be used for turning on the retractor, or for turning on the light sources in a particular sequence as described above, or for selecting one of the light sources to be adjusted; and operations (2) and/or (3) may be used for adjusting the brightness, color and/or angle of the light sources that are turned on or selected either individually or simultaneously together. Such functionality would be intuitive and would allow for a simple one-thumb operation that can perform multiple functions. In addition, combining the push-button switch and/or the multi-directional switch, in any configuration described above, on the end cap assembly is an efficient use of the little space provided on the end cap assembly.

Figure 8:
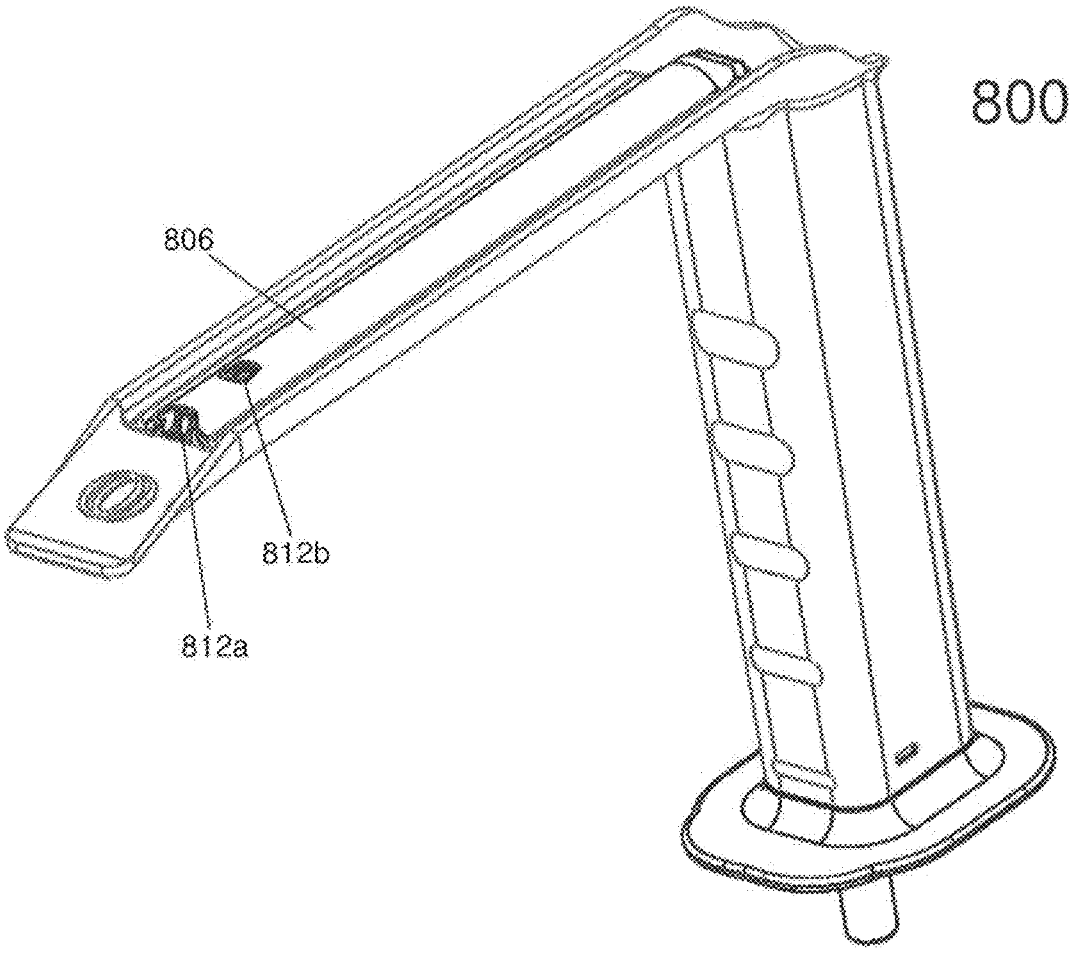
FIG. 8 shows an exemplary retractor that uses the end cap assembly of FIG. 7.

FIG. 8 shows an example of a two-LED retractor 800 that uses the end cap assembly shown in FIG. 7 and described above. As shown in FIG. 8, the LED light sources are integrated into the smoke evacuation cover 806 and are provided at an angle relative to the blade portion. In FIG. 8, the LED light sources 812*a*, 812*b* have a rectangular shape and do not protrude from the smoke evacuation cover. However, the shape and the amount of protrusion from the smoke evacuation cover may be varied. Moreover, as described above, the number of light sources or LEDs and their arrangement along the smoke evacuation cover may be varied.

Textured Non-Slip Pattern

Figure 9A:
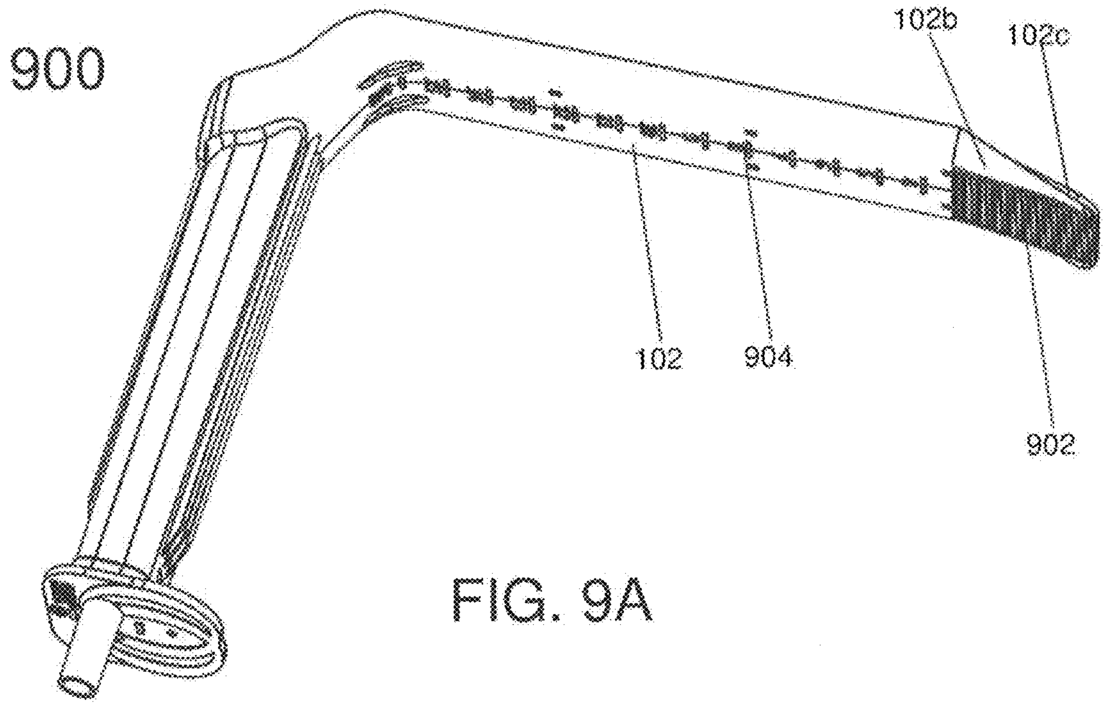
FIGS. 9A-9C show a retractor with a textured gripping surface in accordance with a second embodiment of the present invention.
Figure 9B:
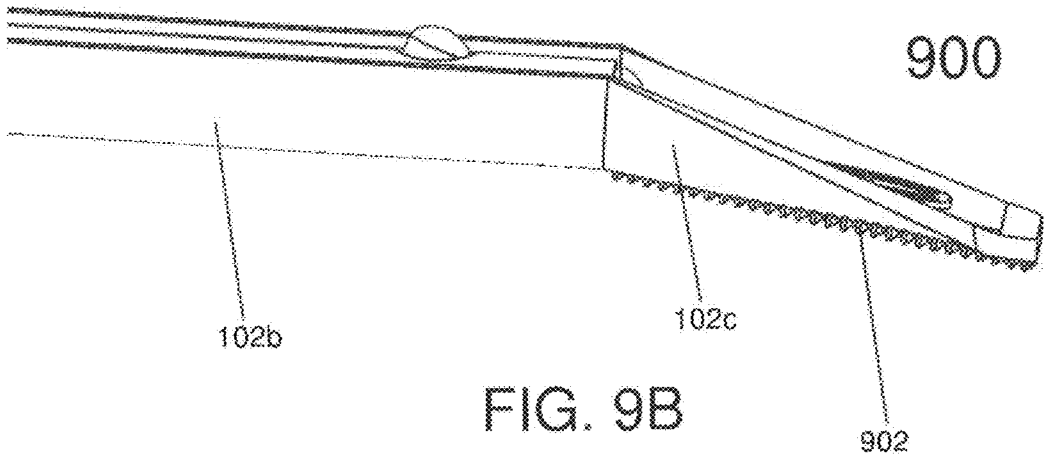
Figure 9C:
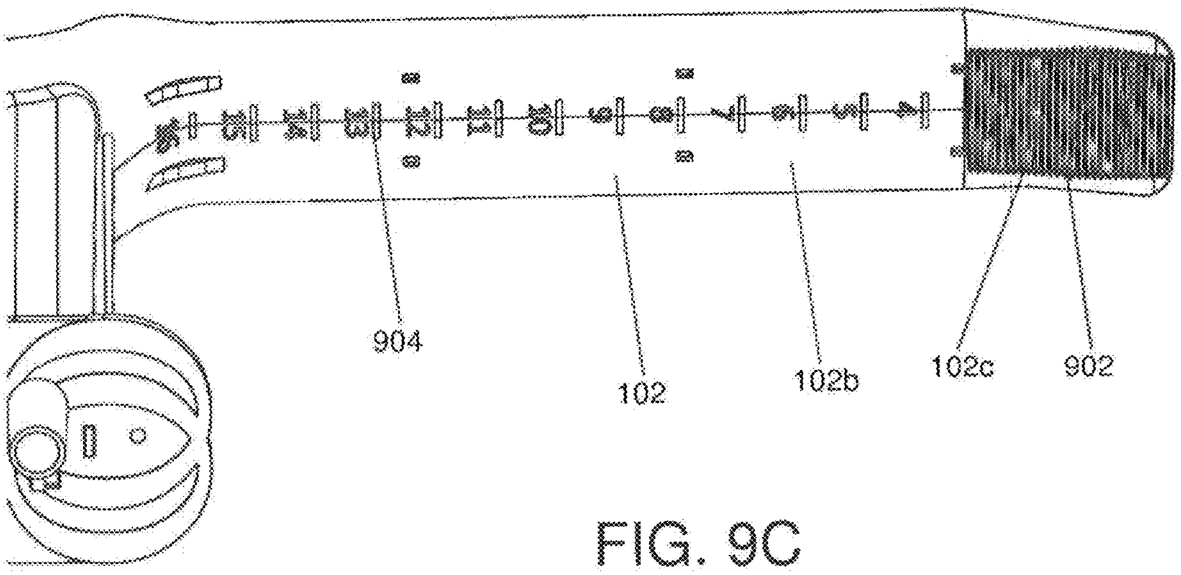

FIGS. 9A-9C show a second embodiment of the present invention illustrating a retractor 900. The retractor 900 may embody one or more features described above with reference to the first embodiment of the retractor in FIGS. 1-8. Parts of the retractor 900 which correspond to those of the retractor 100-800 use the same numeric notations as shown in FIGS. 1-8, and descriptions thereof will be omitted for the sake of brevity.

Notably, the retractor 900 of the second embodiment includes a textured gripping surface 902 formed on the second surface 102*b* of the blade tip 102*c*. The textured gripping surface 902 may also be referred herein as a textured non-slip pattern 902. The textured gripping surface 902 provides a non-slip surface to prevent slippage of the retractor against patient's tissue. In one version, the textured gripping surface 902 is formed only on the second surface 902*b* of the blade. In another version, the textured gripping surface 902 is formed on either or both of the first and second surfaces of the blade. In yet other versions, the textured gripping surface 902 is not limited to the tip of the blade, but may be provided over a portion of the blade's first and/or second surfaces or over the whole first and/or second surface of the blade.

As shown in FIGS. 9A-9C, the textured gripping surface 902 comprises a plurality of elongated ridges formed on at least a portion of the second surface 102*b* of the tip 102*c* or the blade 102. The elongated ridges are substantially parallel to one another and are substantially parallel to the distal edge of the blade. As shown in FIG. 9B, the heights of the elongated ridges may be selected so that the ends of the ridges line up along a linear trajectory. In one version, the heights of the elongated ridges may be substantially the same to one another, and in yet another version, the heights of the elongated ridges may be varied so as to form a textured surface with a desired characteristic.

The specific pattern of the textured gripping surface 902 is not limited to the one shown in FIGS. 9A-9C and may be varied. For example, the gripping surface 902 may include a plurality of ridges provided in a crisscross fashion, or as a plurality of undulating ridges, or a plurality of separated projections, e.g., rounded projections or V-shaped projections, or any other suitable texture to reduce slipping of the retractor. In other embodiments, the textured gripping surface 902 may be provided as an in-molded pattern or as a sandpaper finish. For example, in-molded patterns shown in U.S. Published Application No. 2018/0021100 (particularly, FIG. 11), owned by the applicant herein and incorporated herein by reference, may be used as the textured gripping surface 902.

Although FIGS. 9A-9C show the textured gripping surface 902 formed on the tip 102*c* of the blade, in some versions, the textured gripping surface 902 may be provided on other areas of the blade as mentioned herein above. For example, the textured gripping surface 902 may be provided on the tip 102 of the blade as well as on the entire remaining second surface 102*b*, or a portion of the remaining second surface 102*b* of the blade. In one version, different types of patterns are provided along the length of the blade. For example, one type of a textured gripping surface may be provided on the second surface 102*b* of the blade tip 102*c*, while another type of textured gripping surface may be provided on the remaining second surface 102*b* of the blade or on a portion of the remaining second surface 102*b* of the blade. In one example, raised ridges, as shown in FIGS. 9A-9C or forming other patterns, may be provided on the second surface 102*b* of the blade tip 102*c*, and an in-molded pattern or a sandpaper finish may be provided on the entire remaining second surface 102*b* of the blade or on a portion of the remaining second surface 102*b* of the blade. In another version, one in-molded pattern may be provided on the second surface 102*b* of the blade tip 102*c* and another in-molded pattern or a sandpaper finish may be provided on the entire remaining second surface 102*b* of the blade or on a portion of the remaining second surface 102*b* of the blade. In yet other examples, the textured gripping surface on the tip 102*c* of the blade may be formed in different areas of the tip, e.g., only near the distal edge of the tip, or alongside edges of the tip, or as a narrower strip along the tip, etc. Other variations and arrangements of the textured gripping surface are contemplated by the present invention.

The present embodiment focuses particularly on characteristics of the non-slip pattern that provide the optimal gripping. There are many factors that affect "gripping" in retractor application. Most prior art devices deal solely with the function of gripping, meaning, gripping in all directions. This type of prior art focuses on spikes or other gripping features that are non-preferential, i.e., these patterns grip equally in both forward, backward, and lateral movements. As described herein, a "forward movement" is defined as an insertion movement of a retractor into a body cavity. Gripping in this direction means the retractor will push tissue into the body. As also described herein, a "backward movement" is defined as an extraction movement of a retractor from a body cavity. This means the retractor pulls tissue from the body cavity. Finally, a "lateral movement" means moving the retractor side to side. This means pushing gripped tissue to one side or the other.

Unlike the prior art non-slip pattern retractors, the present invention recognizes that it is seldom desirable to have a retractor move tissue with equal grip in all directions. For example, breast augmentation and other deep pocket surgeries require a physician to create an ever enlarging pocket by separating tissue as the pocket grows deeper and wider. This tissue separation requires moving the retractor laterally within the pocket to continue the tissue separation process. During this process, the physician wants to hold up the upper wall of the pocket with the tip of the retractor blade and thus, does not want the tissue to slip over the retractor tip. This desire requires a tip grip in the extraction direction (i.e., the backward movement). The physician does not want any lateral grip because such a grip will impede the ability to slide the retractor from one side of the surgical pocket to the other. Any lateral grip action would not only impede the physician's progress, but can also possibly damage the gripped tissue due to the required frequency of the lateral movement. In such case, the physician also does not want any forward grip because such a grip would impede the retractor's ability to move deeper into the pocket as the surgery requires. Therefore, deep surgical pocket retractors require a preferential grip in the retraction movement (i.e., in the extraction direction), but not in the insertion or lateral movements.

Figure 10:
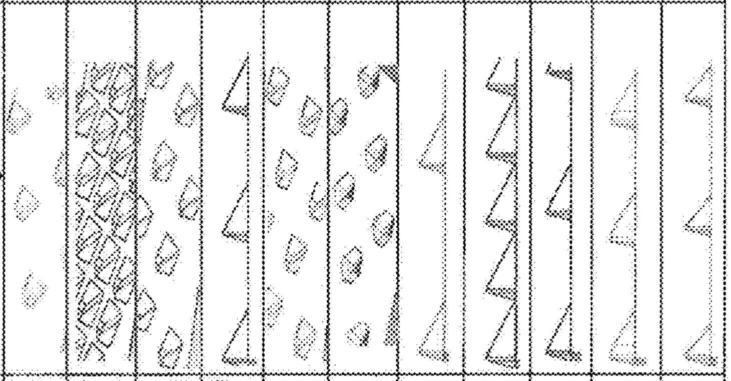
FIG. 10 shows a table summarizing experimental data regarding gripping characteristics of various non-slip patterns of the present invention.

FIG. 10 shows a Table 1000 that includes a summary of experimental data in regards to gripping characteristics of various non-slip patterns/designs/textures of the present invention. In an effort to discover the optimal non-slip pattern, one of the factors measured is the insertion gripping force. As discussed herein, it is desired to minimize the insertion gripping force, while maximizing the extraction gripping force. It is, however, contemplated that any design for providing a strong extraction gripping force will also inevitably exert some form of an insertion gripping force. As such, a gripping pattern that strikes the optimal balance between minimizing the insertion grip while maximizing the extraction grip is highly desired.

As part of the experiment, each retractor gripping feature was dragged across simulated tissue to measure the force required in each direction. The columns labeled "Insertion Force (lb)" and "Removal Force (lb)" summarize, respectively, the insertion gripping force and the extraction gripping force for each tested texture. The column labeled "Insertion" shows a pictorial of an insertion force, with bars that extend further to the left illustrating lower insertion forces. The column labeled "Grip" shows a pictorial of extraction force, with bars that extend further to the right illustrating higher extraction forces. The column labeled "Range" is the difference between the measured insertion force and extraction force. A preferential grip is demonstrated by the range. That is, the higher the range, the more preferential the grip is. In the experiment, the gripping features were pressed against simulated tissue with 1000 g of force, and the gripping features were then pulled or pushed perpendicular to this 1000 g force to measure insertion and extraction forces.

The Table 1000 clearly shows that the spacing and shape of the sawtooth gripping features have a significant impact on the preferential grip (almost a 2 to 1 difference). This is a dramatic, unexpected, and unknown result which is not recognized in the prior art and is not present in conventional "gripping" surfaces. For instance, while Texture 1 displays the highest range, it also exhibits a lateral grip, which is undesired for deep pocket applications, but is useful in other applications. Also, Texture 4 has the highest preferential range of all tip grip patterns that have no lateral gripping features. In Table 1000, Textures 4 and 7-11 are formed as ribs across the width of the blade and/or blade tip, with the ribs having different shapes and different spacing therebetween. Textures 1-3 and 5-6 in Table 1000 are formed as bumps or projections on the surface of the blade and/or blade tip, with multiple projections extending across the width of the blade and/or blade tip in a first direction and along at least a portion of the blade and/or blade tip in a second direction different from the first direction. In the illustrative embodiments shown, the heights of the ribs and bumps or projections of the different textures are approximately 1 mm. However, a deviation of ±10% is acceptable, and in some embodiments a deviation of ±20-25% is acceptable.

In an actual application, the force of the retractor to the tissue is controlled by the surgeon, i.e., the surgeon will apply enough force to achieve adequate retraction grip. A higher grip "range" means that, while achieving adequate retraction grip force, the corresponding insertion and lateral movement forces are minimized. Minimizing insertion and lateral grip forces facilitates the surgeon's task of creating a deep pocket during deep pocket applications and minimizes undesired tissue damage during retractor movements.

Figure 11A:
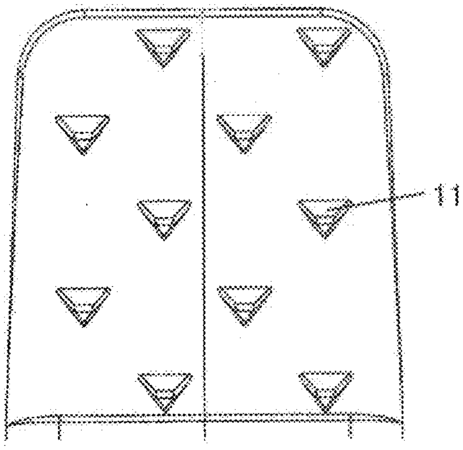
FIGS. 11A-11E show cross-up views of select non-slip patterns included in FIG. 10.
Figure 11B:
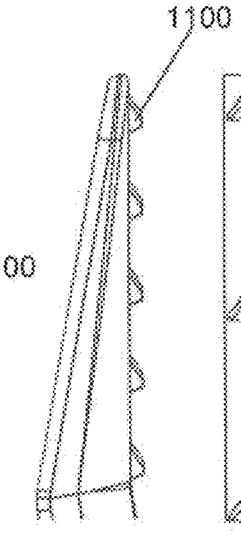
Figure 11C:
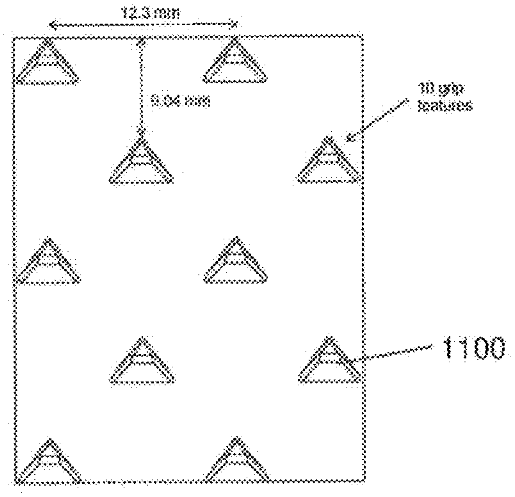
Figure 11D:
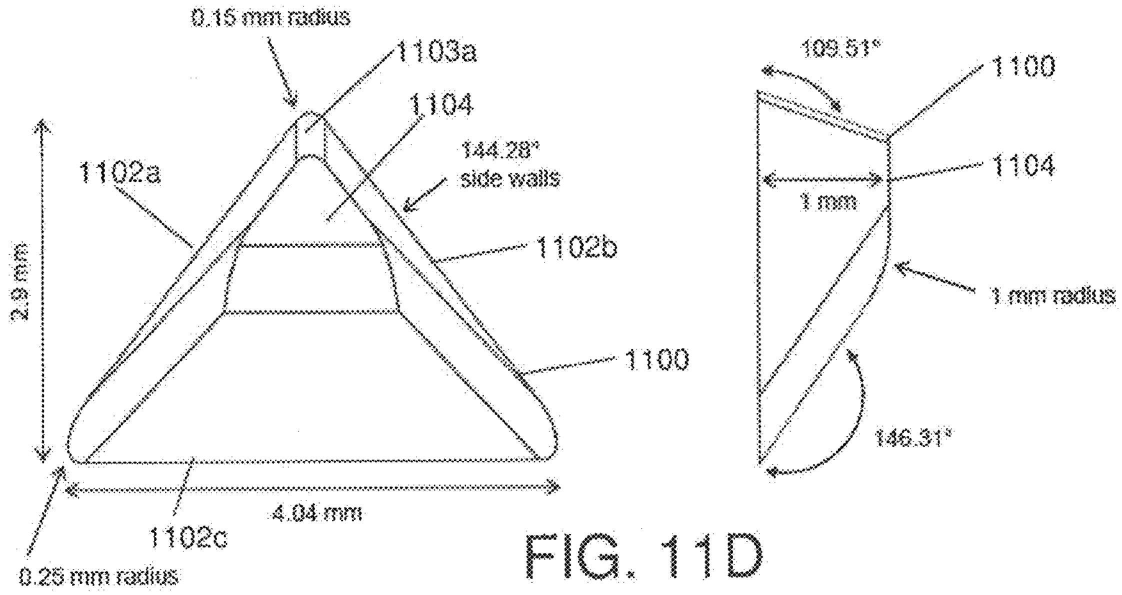
Figure 11E:
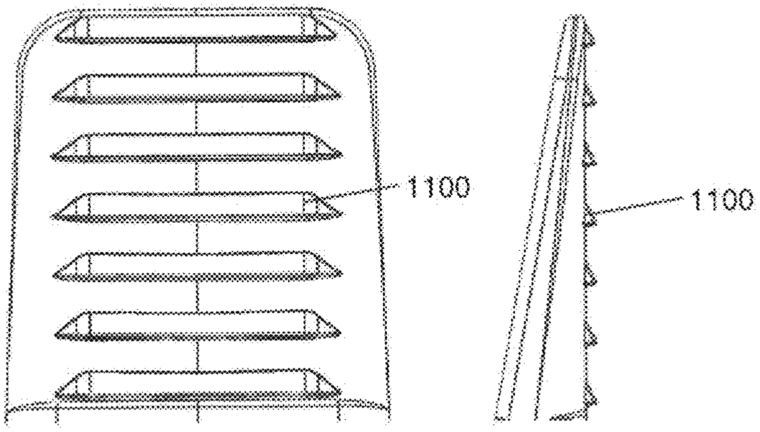
Figure 12A:
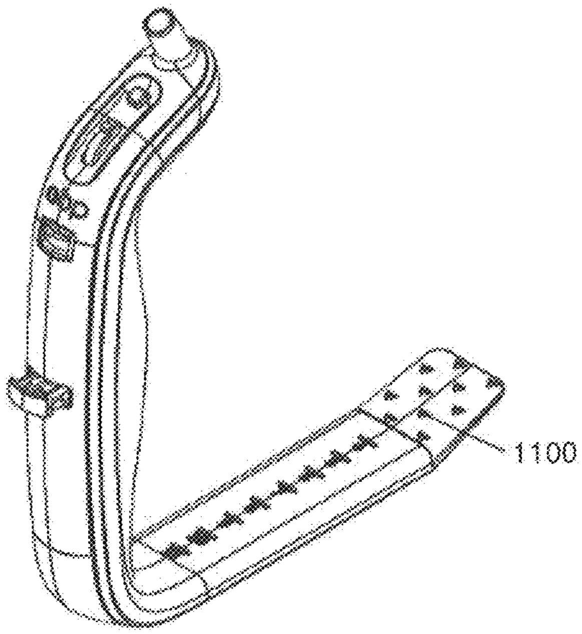
FIGS. 12A-12B show exemplary retractors embodying the non-slip patterns of FIGS. 11A-E.
Figure 12B:
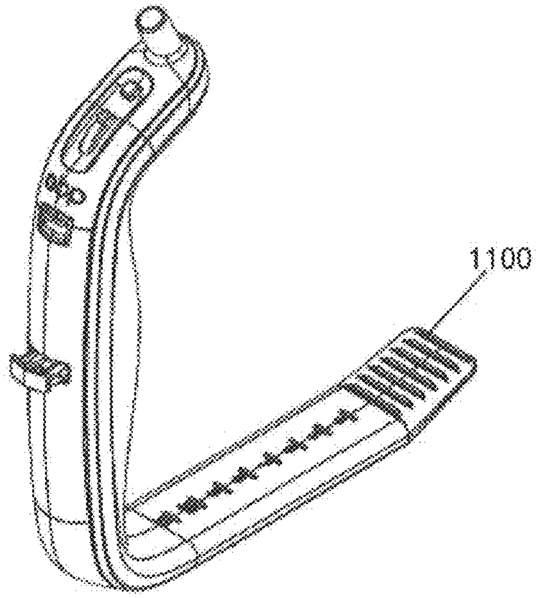

FIGS. 11A-11E provide various close-up views of select non-slip patterns from Table 1000. FIGS. 11A-11D show details of a non-slip pattern corresponding to Texture 1 and FIG. 11E shows details of a non-slip pattern corresponding to Texture 4. FIGS. 12A-B show exemplary retractors embodying the respective textures 1 and 4 from Table 1000. In accordance with the present embodiment, a retractor may be configured so that the non-slip patterns may be exchangeable based on need. That is, a retractor may be configured that a non-slip pattern may be in-molded or alternatively, be configured to receive a non-slip pattern thereon by attachment of a blade or blade tip with the non-slip pattern or by attachment to the blade of a non-slip surface having the non-slip pattern. For example, various non-slip patterns may be manufactured as an add-on component to a retractor to be attached and detached from the surface of the blade.

While the dimensions of a specific gripping features or projections of each non-slip pattern as illustrated in FIGS. 11C and 11D represent values for an optimal preferential gripping pattern, these specific values are not intended to limit the scope of the present invention. A preferred version of this embodiment may allow some deviation from the optimal dimensions depending on the size or the intended use of the medical device. As shown in FIG. 11C, the blade tip includes 10 gripping features 1100 or projections which have a pyramid-like shape and which are inclined away from the distal end of the blade tip. The number of gripping features or projections may vary depending on the size of the retractor blade and its tip. As shown in FIG. 11D, each illustrative gripping feature 1100 or projection has a substantially triangular periphery, with the three sidewalls 1102*a-c* forming a pyramid-like structure and a flattened tip 1104 at the top. The gripping feature or projection is inclined towards a first vertex 1103*a* formed between first and second sidewalls 1102*a* and 1102*b* in a direction away from the distal end of the blade tip, such that the angle between the blade's surface and the first vertex 1103*a* is about 109.5 degrees while the angle between the blade's surface and the third sidewall 1102*c* that opposes the first vertex 1103*a* is about 146.3 degrees. This inclination of each gripping feature provides preferential grip in the removal direction with a lower insertion force and a higher removal force. In the illustrative embodiment of FIGS. 11A-D, the height of each gripping feature is about 1 mm, the length of the third sidewall 1102*c*, i.e., width of the feature, is about 4.04 mm, and the shortest distance between the third sidewall 1102*c* and the first vertex 1103*a*, i.e., length of the feature, is about 2.9 mm. These dimensions of the gripping feature may varied depending on the specific application and size of the retractor. It is preferred, however, that the relative dimensions of the gripping features and the spacing therebetween is similar or substantially the same as those of the gripping features shown in FIGS. 11A-D.

In the illustrative embodiment of FIGS. 11A-D, alignment of the gripping features 1100 in adjacent rows is shifted by about ½ of the distance between adjacent gripping features 1100. In FIG. 11C, the distance between respective first tips of adjacent gripping features 1100 or projections in the first direction across the width of the blade tip is around 12.3 mm, while the distance between the first tips of adjacent gripping features 1100 or projections in the second direction along the length of the blade tip is around 9.04 mm. This arrangement creates optimal spacing so as to achieve the specific insertion and removal forces with desired characteristics. The dimensions of the gripping features may be varied to provide desired gripping characteristics and based on the size of the retractor. A deviation of ±10% for each of these exemplary dimensions is acceptable, and in some embodiments a deviation of ±20-25% is acceptable. It is preferable, however, that the relative dimensions of the gripping features and spacing between the gripping features remains similar or substantially the same.

FIG. 12A illustrates an example of a retractor which has the gripping features 1100 of FIGS. 11A-D provided on one surface of the tip of the blade. In other embodiments, the gripping features may be provided on one entire surface of the blade or a portion thereof, or on both surfaces of the blade or portions thereof, or may be provided on both surfaces of the blade's tip.

In the illustrative embodiment of FIG. 11E, rib-shaped gripping features 1100 are provided on one of the surfaces of the blade's tip. It is understood that the rib-shaped gripping features, or other gripping features may be provided on both surfaces of the blade's tip or may be provided on one or both surfaces of the entire blade or a portion thereof. In this illustrative embodiment, each rib has a substantially triangular cross-section and is inclined away from the blade tip's distal end. Each rib may also have gradually inclined lateral ends in order to minimize lateral gripping forces. In the illustrative embodiment of FIG. 11E, each rib has a length of about 1 mm, a width of about 25 mm, and a height of about 1 mm, and the ribs are spaced with a distance of about 0.9 mm between adjacent ribs. The angle between the blade's surface and the inclined rib wall is about 84 degrees facing the proximal end of the blade, and 17 degrees facing the distal end of the blade. The dimensions of the ribs may be varied to provide desired gripping characteristics and based on the size of the retractor. A deviation of ±10% for each of these exemplary dimensions is acceptable, and in some embodiments a deviation of ±20-25% is acceptable. It is preferable, however, that the relative dimensions of the ribs and spacing between the ribs remains similar or substantially the same. FIG. 12B shows an example of a retractor with the rib-shaped gripping features 1100 of FIG. 11E on one surface of the blade's tip.

Referring back to FIGS. 9A-9C, the retractor 900 of the second embodiment may further include a plurality of measurement markers 904 formed on the second surface 102*b* of the blade 102. The measurement markers 904 indicate a distance from the distal edge of the blade and can be used for informing the physician how deep the retractor blade is in the patient cavity. In different variations, the plurality of measurement markers may be formed only on the second surface 102*b*, or on either or both of the first and second surface of the blade 102.

For example, as shown in FIG. 9C, the measurement markers 904 are provided in centimeters with a marker for each centimeter along the length of the blade. In some versions, the measurement markers 904 may be provided in other units, or may appear less frequently, e.g., a marker for every other cm or inch, or more frequently, e.g., with additional bars at half cm or half inch. The positioning of the measurement markers 904 is not limited to the central area along the length of the second surface 102*b* of the blade. In certain versions, the measurement markers 904 may be provided along one edge or both edges of the blade 102, and may be provided on the first surface 102*a* and/or on the second surface 102*b* of the blade. The measurement markers 904 may be formed on the blade by printing them on the surface of the blade, by embossing, engraving or in-molding the markers on the surface of the blade or by any other suitable techniques. The measurement markers 904 may be flat with respect the surface of the blade, or may project from the surface of the blade or may be recessed into the surface of the blade. In the embodiments in which the measurement markers 904 project from the surface of the blade or are recessed into the surface of the blade, the markers 904 may provide additional gripping to the blade. Other variations and arrangements of the measurement markers are contemplated by the present invention.

Ergonomic Retractor Handle

Figure 13:
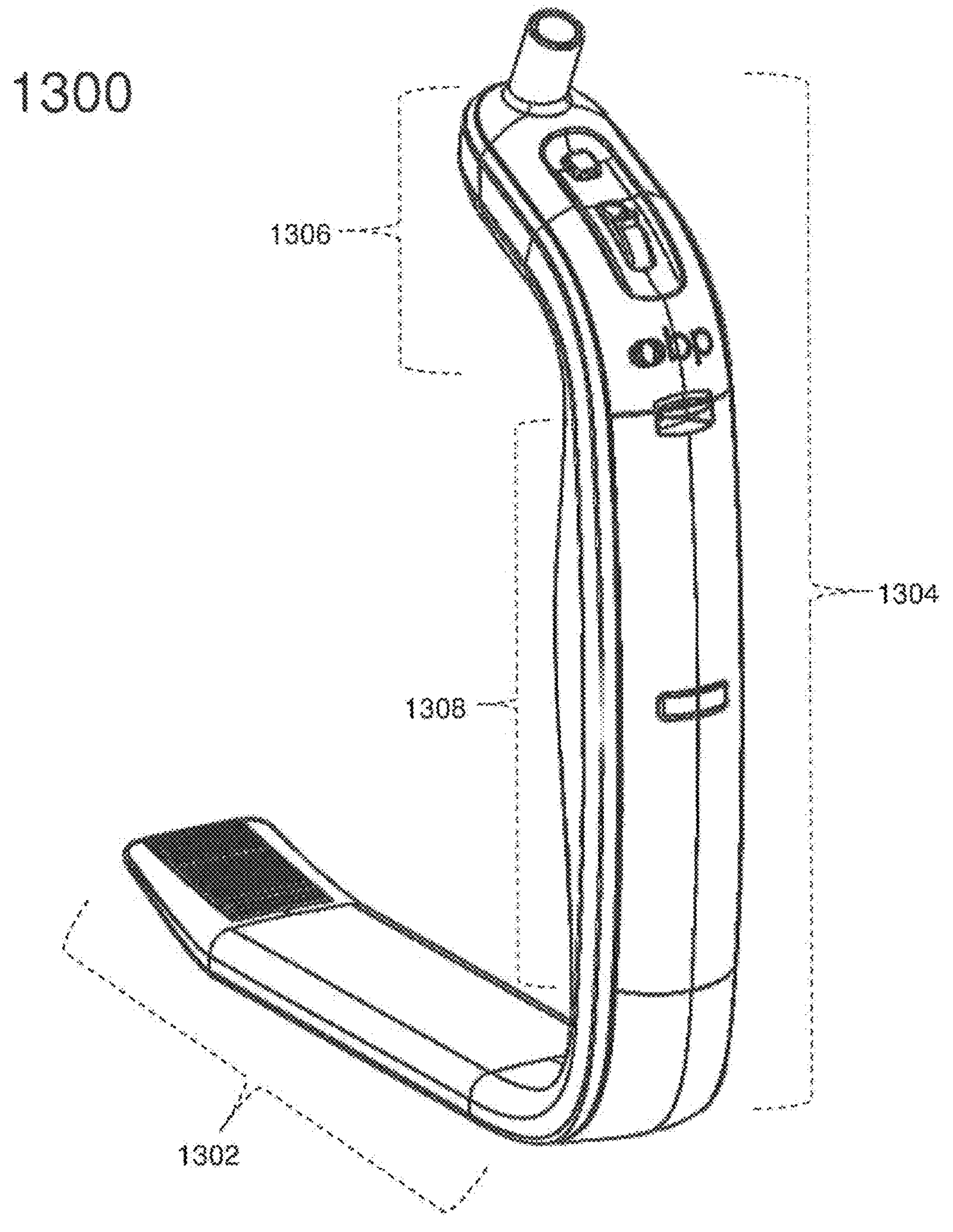
FIG. 13 shows a retractor in accordance with a third embodiment of the present invention.

FIG. 13 shows a retractor 1300 in accordance with a third embodiment of the present invention. As shown in FIG. 13, the retractor 1300 includes a blade portion 1302 and a handle portion 1304. Unlike the retractor of the first embodiment, the retractor 13 in FIG. 13 does not include side flanges extending outwardly from a curved section connecting the blade portion 1302 and the handle portion 1304. This feature allows for better viewing of the surgical site and results from the construction of the blade 1302 and a blade cover, as described in more detail below. Moreover, unlike the retractors described above with reference to previous embodiments, the retractor 1300 of this embodiment does not include an end cap assembly which is insertable into an opening at the distal end of the handle portion. Instead, a distal end portion of the handle portion 1304 of the retractor 1300, where an end cap assembly would have been configured, extends into a curved end portion 1306 which is offset from the plane along the length of the handle portion 1304.

The curved end portion 1306, similar to an end cap assembly as described above herein, includes a smoke evacuation port along with an operating assembly to control operation of one or more LEDs of the retractor and/or other retractor functionalities. In accordance with certain versions of the present embodiment, the curved end portion 1306 may be referred to as being part of the handle portion 1304, while in some other versions, the curved end portion 1306 may be referred to as a separate component that is adjacent to, or otherwise attached to, the handle portion 1304 of the retractor 1300. Specifics of the purpose, functionalities, and/or components of the curved end portion 1306 will be further described herein. In other variations, the distal end portion 1306 is not curved and may be co-extensive with the remainder of the handle or may have any other suitable configuration. Finally, the handle portion 1304 of the retractor 1300 is configured with a power source storage portion

1308 that stores a power source, such as one or more batteries, and includes a push-tab assembly to be further described below herein.

In the embodiment of FIG. 13, the plane in which curved end portion 1306 extends is offset from the plane along the length of the handle portion 1304. That is, the curved end portion 1306 is not co-extensive with the handle portion 1304 and is angled relative to the handle portion 1304. In the illustrative embodiment of FIG. 13, the curved end is angled in the same direction as the direction of the blade portion 1302. The offset curved end portion 1306 and the handle portion are ergonomically designed so as to allow for comfortable holding of the retractor during operation in different orientations and to allow one hand operation and control of the retractor and of the illumination assembly of the retractor. By providing the operating assembly on a rear surface of the curved end portion 1306, which faces away from the direction of the handle and by offsetting the curved end portion 1306 from the plane of the handle portion, a user can hold the retractor in either hand and in any orientation and can operate the operating assembly on the curved end portion with a thumb or a pinky finger without requiring overextending of the user's hand. In addition, as shown, the handle portion may also have a protruding or slightly bulbous shape to provide additional comfort while holding the retractor.

Retractor With an Integrated Smoke Evacuation System and LED Flex Circuit

Figure 14A:
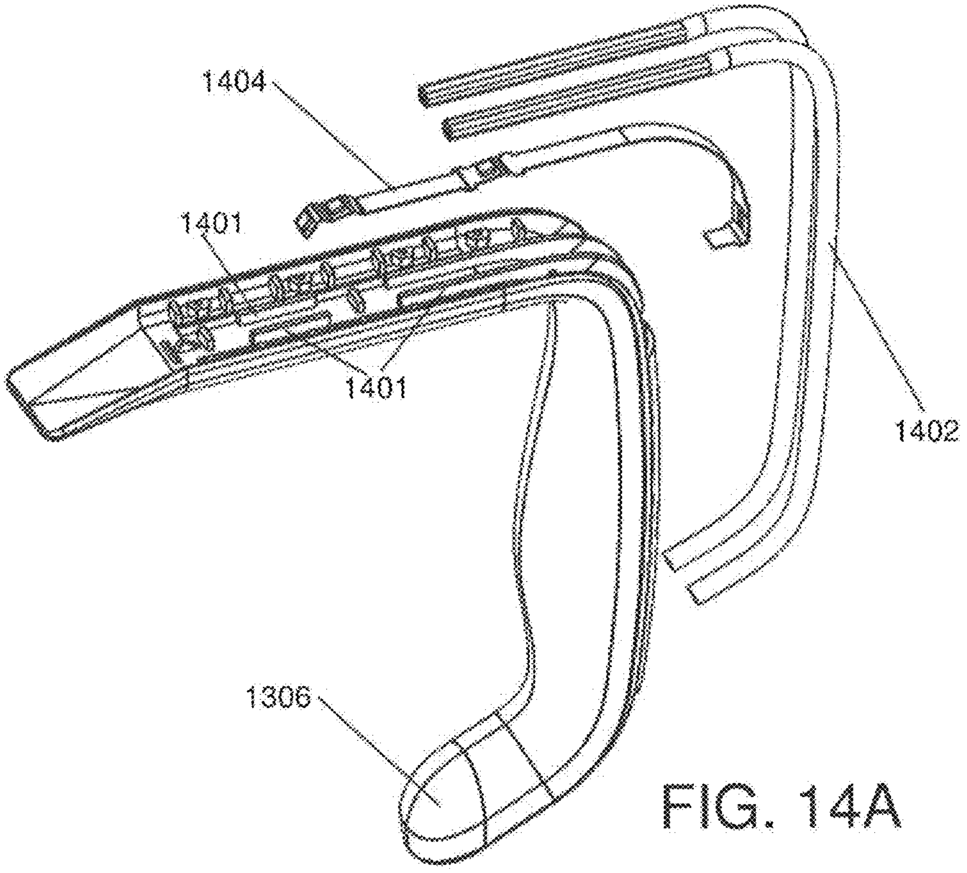
FIGS. 14A-14D show various views of the retractor of FIG. 13 including a smoke evacuation system and an LED flex circuit.

FIGS. 14A-14D show various views (e.g., a perspective exploded view, enlarged views and a cross-sectional view) of the retractor 1400 which is substantially the same as or similar to the retractor 1300 described with reference to FIG. 13. The exploded view of the retractor 1400 in FIG. 14A shows that the retractor 1400 includes a pair of tubes (or conduits) 1402 and an LED flex circuit 1404. In accordance with this embodiment, the pair of tubes 1402 function as and/or replace the smoke evacuation channel described herein above with reference to the previous embodiments. Similar to the smoke evacuation channel in retractors of the previous embodiments, the pair of tubes 1402 run along the blade portion and the handle portion of the retractor 1400 and are in fluid communication with the smoke evacuation port positioned on the curved end portion of the retractor 1400. More specifically, the pair of tubes 1402 serve as fluid conduits to direct smoke, fumes, liquids and/or small debris from the distal end of the blade portion, through the length of the retractor 1400, and out the smoke evacuation port located at the curved end portion of the retractor 1400. While in the illustrative version of FIGS. 14A-14D, two tubes 1402 are provided for smoke and/or debris evacuation, in other versions, only one tube may be provided or more than two tubes may be used.

In accordance with various embodiments disclosed herein, the medical devices of the present invention include an illumination assembly, which comprises one or more light sources (e.g., LEDs), and the illumination assembly is integrated into the blade portion of the retractor along with a blade cover. The blade cover provides the air-conduit space and functions as a smoke evacuation channel. In the previous embodiments, the positions of the LEDs of the illumination assembly corresponded with the positions of a plurality of openings formed in the blade cover to allow light to escape via the plurality of openings.

In accordance with the present embodiment, the retractor 1400 has an illumination assembly comprising the LED flex circuit 1404 that functions as and/or replaces the one or more LEDs and wiring of the illumination assembly described herein above. The LED flex circuit 1404 includes a flexible substrate, in this version formed as a flexible strip, with one or more LEDs mounted thereon. The LED flex circuit 1404 incorporates wiring and electrical connections in the flexible substrate for electrically connecting the LED(s) to the power source and to an operating assembly and/or a control assembly for controlling the LED(s). The flexible substrate may also incorporate therein one or more circuits for controlling the operation of the LEDs. The LED flex circuit 1404 also includes a connecting portion to provide an easy electrical connection to other components of the illumination assembly, e.g., the power source and/or the operating assembly.

Moreover, the retractor 1400 includes the pair of tubes 1402, each of which run separately and adjacent to the LED flex circuit 1404 on either side thereof. As discussed above, the pair of tubes 1402 extend from the blade portion into the handle portion and extend into the distal end portion 1306 of the handle. In some versions, the tubes 1402 end in the distal end portion 1306 near the smoke evacuation port, while in other versions, the tubes 1402 may be coupled to the smoke evacuation port in the distal end portion 1306. In yet other variations, the tubes 1402 may terminate at another point within the handle portion of the retractor.

Figure 14B:
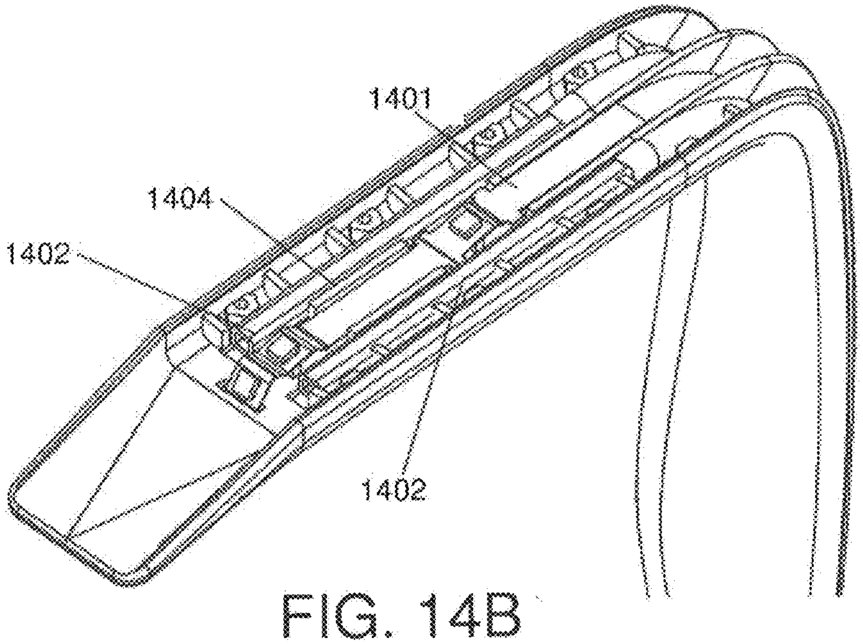
Figure 14C:
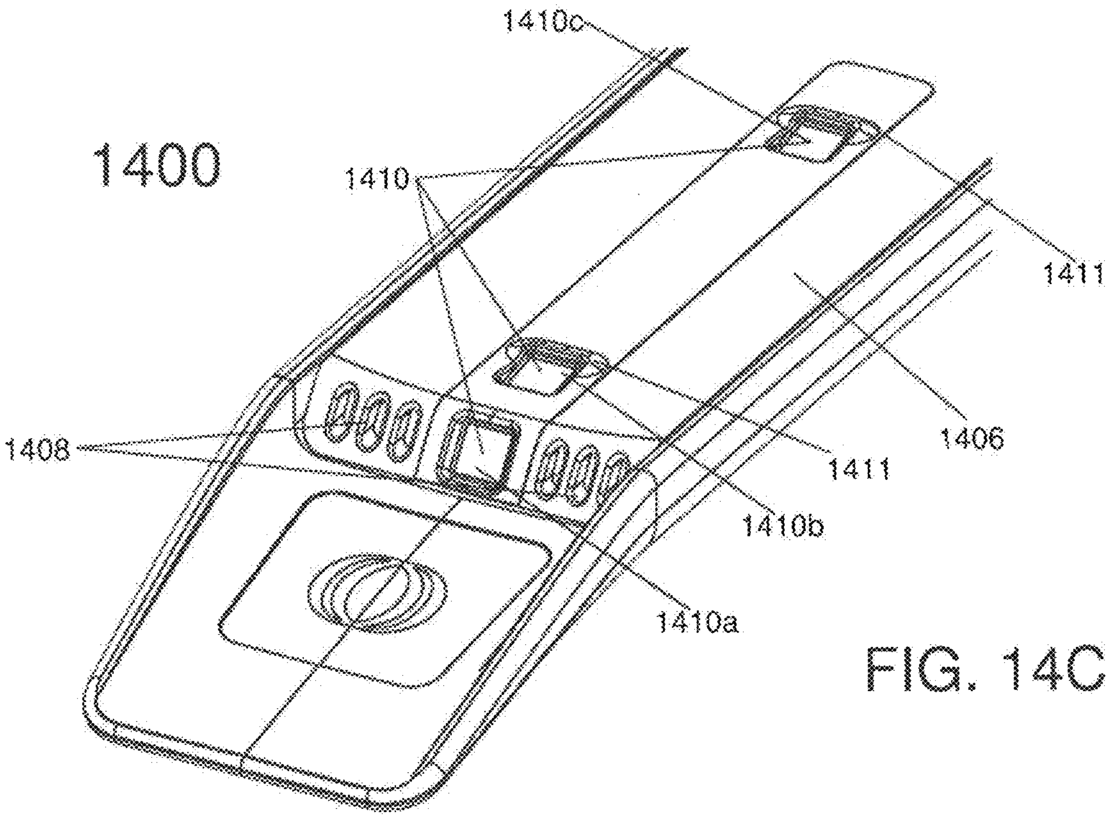

Additionally, the retractor 1400 includes a blade cover 1406, a portion of which is shown in FIG. 14C, that encloses both the LED flex circuit 1404 and the pair of tubes 1402. In some versions, the blade cover 1406 covers the entire width of the blade portion of the retractor 1400, while in other versions, the blade cover 1406 covers only a portion of the width, e.g., the width of the LED flex circuit 1404 and the pair of tubes 1402. The length of the blade cover 1106 may be similar to the smoke evacuation channel of the previous embodiments. In FIG. 14C, a distal end of the blade cover 1406 covers distal ends of the pair of tubes 1402 and the LED flex circuit 1404, and is positioned at or near an angled tip of the blade portion. A proximal end of the blade cover 1406 may end at the proximal end of the blade or may extend to cover a curved portion connecting the blade to the handle and even to cover a proximal end portion of the handle portion.

FIG. 14B illustrates the retractor 1400 in which the pair of tubes 1402 and the LED flex circuit 1404 are assembled in their respective positions on the blade portion of the retractor 1400, without the blade cover 1406. The LED flex circuit 1404 enables the positions and/or the angles of the LEDs to be individually defined by the support features of the blade, e.g., support ribs or projections on the blade, and the blade cover 1406. Moreover, as shown in FIG. 14B, the LED flex circuit 1404 may be retained between a plurality of retaining walls 1401, which provide additional support for the LED flex circuit 1404 and additional strength to the blade. In the illustrative version of FIG. 14B, the retaining walls 1401 are provided at selected positions to retain selected portions of the LED flex circuit 1404 and so as not to abut the LEDs mounted on the LED flex circuit 1404. This configuration allows for easy adjustment of the angles of the LEDs. However, in other versions, the retaining walls may be provided in other positions, including those abutting the LEDs of the LED flex circuit 1404. In this embodiment, the retaining walls 1401 also separate the LED flex circuit 1404 from the tubes 1402 and help retain the tubes 1402 in their respective positions, so as to prevent shifting of the tubes 1402 and of the LED flex circuit 1404 and overlapping between portions of the tubes 1402 and the LED flex circuit 1404. In other embodiments, the retaining walls may be omitted or limited and the LED flex circuit may be modified, as shown in FIGS. 15B-C and 16A-D, to include wings which overlap with the tubes of the smoke evacuation system. In some embodiments using the LED flex circuit shown in FIGS. 15B-C and 16A-D, the retaining walls may be used only for retaining the tubes 1402 in place and the LED flex circuit may be positioned adjacent to the blade cover 1606 as shown in FIG. 16B and when assembled with the blade, the LED flex circuit wings cover and overlap with the tubes of the smoke evacuation system.

FIG. 14C shows a distal end portion of the blade cover 1406 that covers or encloses the upper surface, or a portion of the upper surface, of the retractor blade portion to enclose the pair of tubes 1402 and the LED flex circuit 1404. In the version shown in FIG. 14C, the cover has a top surface, which is substantially parallel to the upper surface of the blade portion, and a distal end extending at an angle from the top surface toward the upper surface of the blade portion. FIG. 14C shows that the blade cover 1406 includes a pair of gratings or grills 1408 each of which corresponds to, and aligns with, a respective tube 1402. The gratings 1408 are provided in the distal end of the cover 1106 and serve as a filter to block out larger debris that might clog the tubes 1402 during fluid and/or smoke evacuation processes. The particular sizes, shapes and designs of the gratings 1408 may be varied without departing from the scope of the present invention. For example, the size of the grate openings may depend on the type of surgery for which the retractor is used.

As further shown in FIG. 14C, the blade cover 1406 of the retractor 1400 also includes a plurality of openings 1410, with each of the openings corresponding to a respective LED mounted on the LED flex circuit 1404. In the version of FIG. 14C, the plurality of openings include a first opening 1410*a* provided in the distal end of the cover 1406 between the gratings 1408, with a corresponding LED exposed through the first opening. The angle of the LED exposed through the first opening 1410*a* may be aligned with the angle of the distal end of the cover 1406 or may be provided at an angle relative to the distal end of the cover 1406. In addition, the angle of the LED exposed through the first opening may be adjustable.

In the version of FIG. 14C, a second opening 1410*b* is provided near the distal end of the cover 1406 in the top surface of the cover 1406 and a corresponding LED is exposed through the second opening 1410*b*. The LED exposed through the second opening 1410*b* may be angled relative to the top surface of the cover 1406 and its angle may be adjustable. In addition, the LED may be positioned such that a portion thereof protrudes from the second opening 1410*b* and/or may be positioned such that a portion thereof is below the top surface of the cover 1406. The cover may include one or more projections 1411 or ridges protruding from the surface of the cover 1406 and adjacent each opening on the top surface of the cover 1406, e.g., adjacent the openings 1410*b*, 1410*c*, in order to block light emitted from the LEDs from being directed toward the proximal end of the blade portion and/or toward the user of the retractor. In the embodiment of FIG. 14C, the projections 1411 extend adjacent a proximal end of each opening 1410*b*, 1410*c* on the top surface of the cover 1406. In some embodiments, the projections may extend slightly above the LED exposed through the opening 1410*b*, 1410*c* in order to block additional light emitted from the LED. In certain embodiments, the projection 1411 may have a reflective inner surface that faces the LED in order to direct light emitted from the LED toward the distal end of the blade portion. The plurality of openings 1410 may also include a third opening 1410*c* and/or other openings with corresponding LEDs exposed therethrough. In the version of FIG. 14C, the third opening 1410*c* has substantially the same or similar configuration to the second opening 1410*b* and the angle of the LED exposed through the third opening 1410*c* may be the same or different from the angle of the LED exposed through the second opening 1410*c*.

Various other characteristics of the LEDs on the blade portion of the retractor with respect to the illumination assembly and the blade cover have been described herein above with respect to other embodiments, and one or more features of the previous embodiments with respect to the LEDs and the openings in the blade cover may be incorporated in this embodiment. For example, the number of LEDs may vary, the positioning of the LEDs may vary, and/or the angles of the LEDs with respect to the blade portion may vary and be adjustable without departing from the scope of the present invention.

Figure 14D:
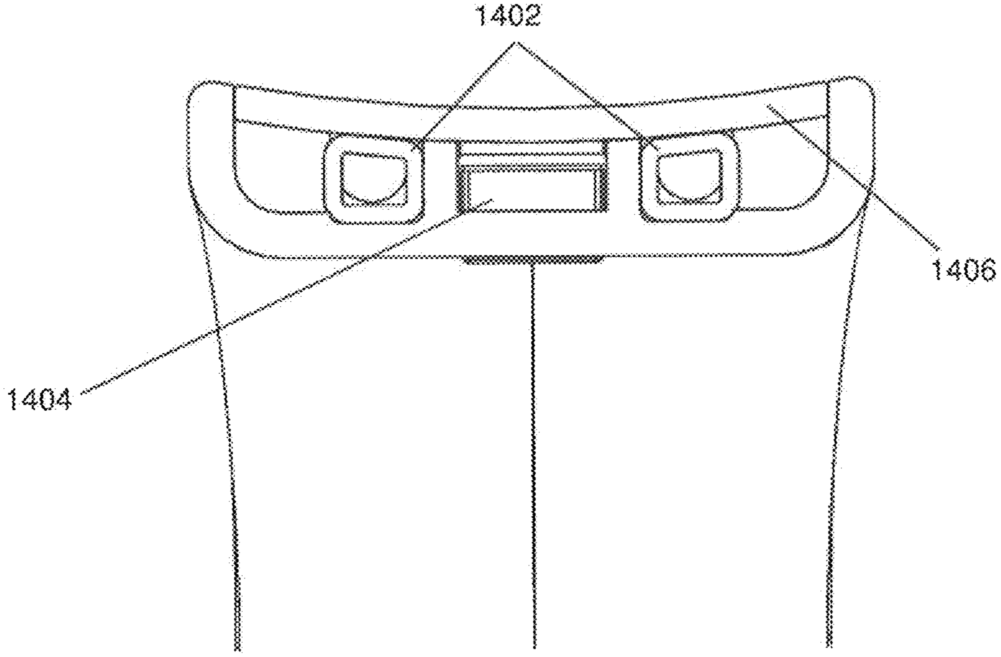

FIG. 14D is a detailed cross-sectional view of the blade portion of the retractor 1400 showing the pair of tubes 1402 running along each side of the LED flex circuit 1404 under the blade cover 1406 of the blade portion of the retractor 1400.

It is to be noted that the particular use of the LED flex circuit 1404 and the blade cover 1406 as shown in these figures is not intended to be limiting. In particular, the quantity, placement and positioning of LEDs on the LED flex circuit is subject to custom design, and thus, a corresponding blade cover may be appropriately designed to accommodate a particular design of LED flex circuit(s).

Modified LED Flex Circuit for Improved Thermal Dissipation

As previously discussed herein, lighting of body cavities with an illuminated medical device comes with the well-documented problem of heat being created as a by-product and causing tissue damage. Even highly efficient LEDs only convert 30-40% of their energy into light and the rest is converted into heat.

One existing solution includes keeping the light source external to the medical instrument and thus, out of the surgical pocket, and feeding the light to the surgical pocket via light pipes (e.g., fiber optics). This solution requires a thermal path to dissipate heat and this thermal path is most often configured as an additional metal bar placed in contact with the light transfer devices in the surgical pocket. The requirement for intense external light sources, complex light transfer mechanisms, and thermal management makes this solution very expensive and not feasible.

Another existing solution is to mount LEDs onto the handle portion of the surgical instrument since the handle is not intended to enter the surgical pocket. While this solution keeps all thermal generation external to the surgical pocket, there are many aspects in which this solution still impedes a doctor's visualization. For instance, a portion of the light will enter the surgical pocket, but another portion will illuminate the skin around the surgical incision and create bright areas outside the pocket that distract from pocket visualization. Also, the light entering the surgical pocket is directional, meaning, it will only illuminate the side of the surgical pocket opposite the incision, and thus full pocket visualization is inhibited.

In accordance with the present invention, the illuminated medical devices of the present embodiment overcome the shortcomings of the existing solutions. More specifically, the present invention recognizes that typical LEDs have thermal rises of 100-150 degrees C./Watt and that tissues exposed to 60° C. of heat even for a few seconds can be severely damaged. There is a thermal limit that bars the amount of power that can be fed to an LED. As a result, the present invention contemplates that power levels into an LED must be limited to approximately 150 mW or less to limit the thermal rise above the temperature of the surgical pocket to below 60° C.

As in previous embodiments, the present embodiment focuses on the use of an LED flex circuit to accommodate various LED mounting angles, as well as for transmission of electrical signals across a surgical retractor. In further accordance with the present embodiment, various modifications to traditional flex circuits are contemplated in order to overcome the shortcomings of the existing art. First, in accordance with the present embodiment, the normal PCB copper thickness is doubled from 35 μm to at least 70 μm (i.e., at least 2 oz of copper thickness). This change in the copper thickness of the PCB halves the thermal resistance of the copper path. Second, the resistance path is changed by covering all available areas of the PCB substrate with copper. This is done by making electrical contact paths wide enough to cover the complete PCB substrate on both the top and the bottom surfaces, except for a minimum spacing required between electrical contact paths. This change maximizes the board's ability to conduct heat in all directions away from the LED. Third, the PCB substrate area is increased through the use of tabs or wings. Tabs added to the substrate are more than two times the normal width required for an LED printed circuit board. These tabs can be configured to fit in an unused area of the surgical instrument and thus not impede functionality. The combination of increased copper thickness, increased copper coverage on the top and bottom surfaces of the board, and increased board area collectively reduces the thermal resistance to 75° C. or less, and allows for twice as much power into the LEDs without sacrificing patient safety. Doubling the power into the LEDs will also double the amount of light, i.e., brightness, provided, thus significantly improving surgical pocket visualization while maintaining low cost.

Exemplary illustrations of the above described modifications to the LED flex circuit are shown in FIGS. 15B-15C. FIG. 15A shows an LED flex circuit 1500*a* similar to the LED flex circuit shown in FIGS. 14A-B. FIG. 15B shows a top view of a modified LED flex circuit 1500*b* with improved copper coverage and improved board area through the use of wings 1510 outside of the LED area. FIG. 15C shows a bottom view (i.e., the underside) of the LED flex circuit 1500*b* showing additional copper coverage. As shown in these figures, the addition of wings in the LED flex circuit 1500*b* of FIGS. 15B-C, and other modifications to the LED flex circuit in accordance with the present embodiment maximize the amount of copper usage for a given application.

In the LED flex circuits 1500*a-b* of FIGS. 15A-15C, a copper layer is provided on both sides of the LED flex circuit and the thickness of the copper layer is at least 2 oz or at least 70 μm, as described above. In addition to the copper layers provided on both sides of the LED flex circuit substrate, the LED flex circuits may also include a coverlay top layer, i.e., top soldermask, provided on one or both sides of the board as an additional electrically insulating layer. The electrically insulating coverlay passivates the LED flex circuit or portions thereof so that the passivated areas of the LED flex circuit can work with the smoke evacuation system described above to provide airflow over the LED flex circuit and thus, further decrease the thermal resistance from the LED to ambient. With such airflow over the LED flex circuit, additional thermal reductions of more than two times the previous reductions can be expected and thus, would allow even more power to be provided to the LEDs, resulting in higher luminous intensity.

FIG. 15D shows a Table 1500*d* that provides an exemplary set of values for various layers of the LED flex circuit board. As shown in Table 1500*d*, the thickness of the copper coverage has nearly doubled, both on the top layer and the bottom layer, to 2 oz of copper thickness, or 71 μm. As also shown in Table 1500*d*, the LED flex circuit of the present embodiment can include one or more layers of soldermasks, or coverlays, which are electrically insulating and are used to passivate the board. These top soldermasks have a thickness of about 25 μm. The specific values (or range of values) or the specific materials described are exemplary and are not intended to limit the scope of the present invention.

Figure 16A:
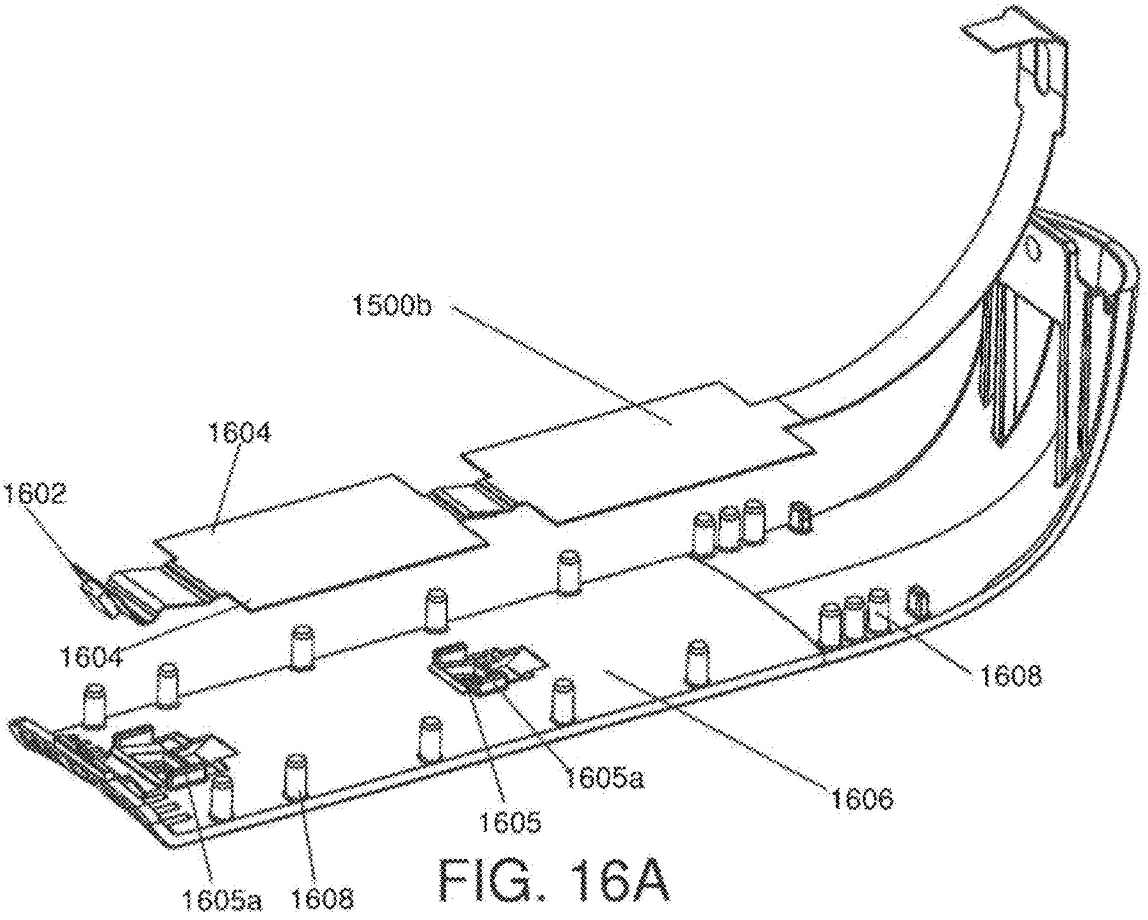
FIGS. 16A-16D show a retractor in accordance with a fourth embodiment of the present invention.
Figure 16B:
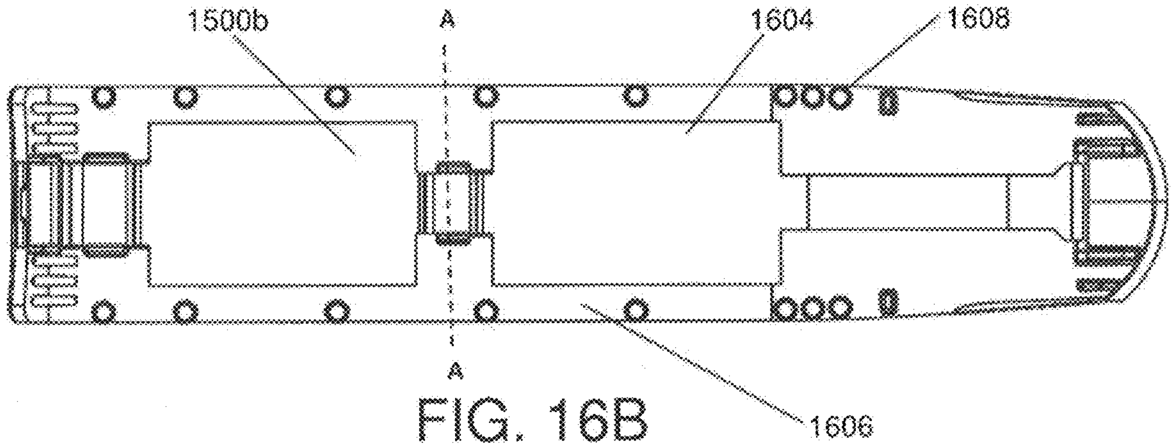

FIGS. 16A-D and FIG. 17B show a fourth embodiment of a surgical retractor 1600, 1700 that uses the LED flex circuit 1500*b* of FIGS. 15B-C. FIGS. 16A-D show the LED circuit 1500*b* assembly with a retractor blade cover 1606. FIG. 16A is an exploded view of the LED flex circuit 1500*b* and the retractor blade cover 1606, while FIG. 16B shows the positioning of the LED flex circuit 1500*b* relative to the blade cover 1606. As shown in these figures, the particular shape, size, and contour of the LED flex circuit 1500*b* is designed to correspond to a specific position on the retractor blade cover 1606 and to the openings formed in the retractor blade cover 1606. Specifically, the size and positioning of the LEDs and the wings 1604 or tabs and the thickness of the LED flex circuit are designed to smoothly fit with the retractor blade and the retractor blade cover 1606 so as not to impede with other functionalities of the retractor.

As shown in FIG. 16A, the LEDs 1602 are mounted on portions of the LED circuit 1500*b* substrate without wings 1604 and when the LED circuit 1500*b* is assembled with the blade cover 1606, the LEDs are positioned to align with the openings 1605 formed in the cover 1606 and the portions of the LED circuit on which the LEDs are mounted may be held by ribs or supporting projections 1605*a* formed on the inner surface of the blade cover 1606 at or near the edges of the openings 1605. As shown in FIGS. 16A-B, certain portions of the length of the LED flex circuit 1500*b* substrate which do not have LEDs mounted thereon include wings 1604 or tabs extending along the sides thereof. As described herein above, these wings 1604 increase the surface area of the LED flex circuit 1500*b* to which the copper layers are applied so as to increase thermal resistance.

Figure 16C:
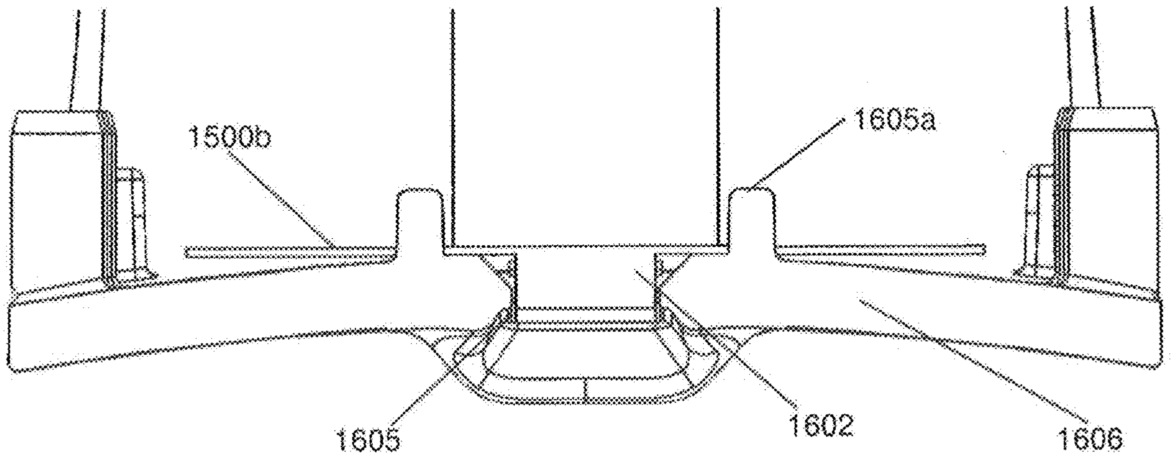

A cross-sectional view of the blade cover 1606 with the LED circuit board 1500*b* along the line A-A in FIG. 16B is shown in FIG. 16C. In FIG. 16C, the LED 1602 of the LED circuit board 1500*b* is held within the opening 1605 in the blade cover 1606 and the ribs 1605*a* near the opening 1605 hold the LED circuit board portion on which the LED is mounted in place to prevent shifting of the LED. As also shown in FIG. 16C, the wings 1604 extend around the ribs 1605*a* so as to further improve retaining of the LEDs in place. With this construction, the LEDs are retained within and/or aligned with the openings 1605 formed in the blade cover 1606.

Figure 16D:
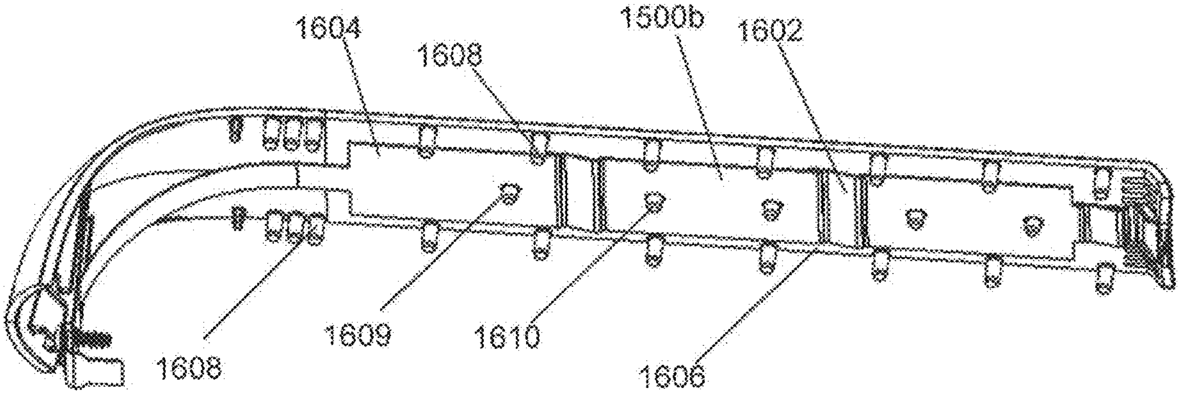

FIG. 16D shows another version of the blade cover 1606 assembled with the LED flex circuit 1500*b* which is modified to include a new method of securing the LED flex circuit 1500*b* to the blade cover 1606. In this version, the substrate of the LED flex circuit 1500*b* includes a plurality of slots 1609 and the blade cover 1606 includes a plurality of posts 1610 corresponding in positions to the plurality of slots 1609. In the illustrative embodiment of FIG. 16D, the slots 1609 are oval in shape and the posts 1610 have a cylindrical shape with a round or oval cross-section, and the widths of the slots 1609 are slightly smaller than the widths of the posts 1610 on the blade cover 1606. The slots 1609 are placed over the corresponding posts 1010 on the blade cover 1606, and when the posts 1610 are inserted into the corresponding slots 1609, the periphery of the slots 1609 grabs the posts 1610 due to the sizing of the slots 1609 and secures the LED flex circuit 1500*b* to the blade cover 1606. It is understood that the shape of the slots 1609 is not limited to oval shapes, and that the slots 1609 and the corresponding posts 1610 may have different shapes as long as the slots 1609 securely engage with the posts 1610. With this configuration, the need for narrow ridge retainers for holding the LEDs in place is eliminated, and the LED flex circuit can have an even larger surface area for the copper layers and the coverlays so as to dissipate more thermal energy and to lower the temperature of the LEDs. As can be seen in FIG. 16D, the area of the LED flex circuit 1500*b* substrate adjacent some of the LEDs 1602 has the same or similar width as that of the wings 1604, which provides the larger surface area.

When the LED flex circuit 1500*b* and the blade cover 1606 shown in FIGS. 16A-D are assembled with the blade portion of the retractor and the tubes of the smoke evacuation assembly, the wings 1604 of the LED circuit overlap with the tubes so as to hold the tubes 1612 in place relative to the blade portion. FIG. 17B shows an exploded view of the retractor that includes the LED flex circuit 1716 of this embodiment and the blade cover 1718 as well as the tubes of the smoke evacuation assembly. As shown in FIG. 17B, the tubes 1714 are inserted between a concave surface of the blade portion and the LED flex circuit 1716 assembled with the blade cover 1718, so that the tubes 1814 overlap with the wings of the LED flex circuit 1716 on each side thereof, and the blade cover 1718 is press-fit with the blade portion. Thus, the tubes are held in place between the wings of the LED flex circuit and the concave surface of the blade portion.

Referring back to FIGS. 16A-B and 16D, the blade cover 1606 includes a plurality of cylindrical posts or pins 1608. When the blade cover 1608 is press-fit with the blade portion, the pins 1608 on the blade cover are inserted into corresponding openings formed in the blade portion. In certain embodiments, the openings in the blade portion have a different shape, such as a hexagonal shape, and are sized so that when the pins 1608 of the blade cover are inserted into the openings, the pins 1608 have to deform and conform to the shape of the openings in the blade portion. Since the pins 1608 have a different shape from the openings in the blade portion, the pins may be made from a softer material so that the pins can conform to the shape of the openings. In some embodiments, the blade cover has pins with a first shape or cross-section, while the openings in the retractor blade have a second shape, different from the first shape. When the blade cover is press-fitted with the blade portion, the coupling strength between the blade and the cover is increased as well as the strength of the retractor blade is increased. With the blade cover strengthening the retractor blade, the retractors embodying such feature are able to withstand higher amounts of force and higher loads during use. Moreover, this construction of the blade and the blade cover 1608 allows for elimination of side flanges in the curved section connecting the blade portion to the handle portion, without sacrificing strength of the retractor.

Retractor Handle and Push Tab Assembly

Figure 17A:
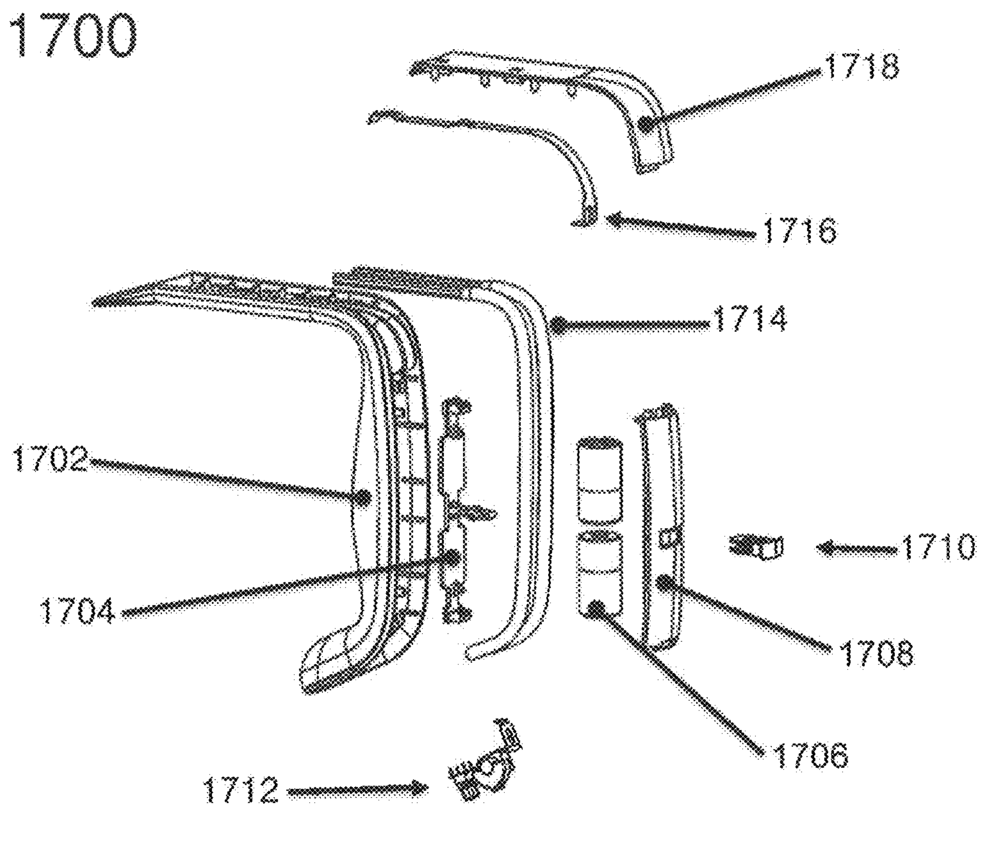
FIGS. 17A and 17B show exploded views of a retractor of the third and fourth embodiments, respectively.
Figure 17B:
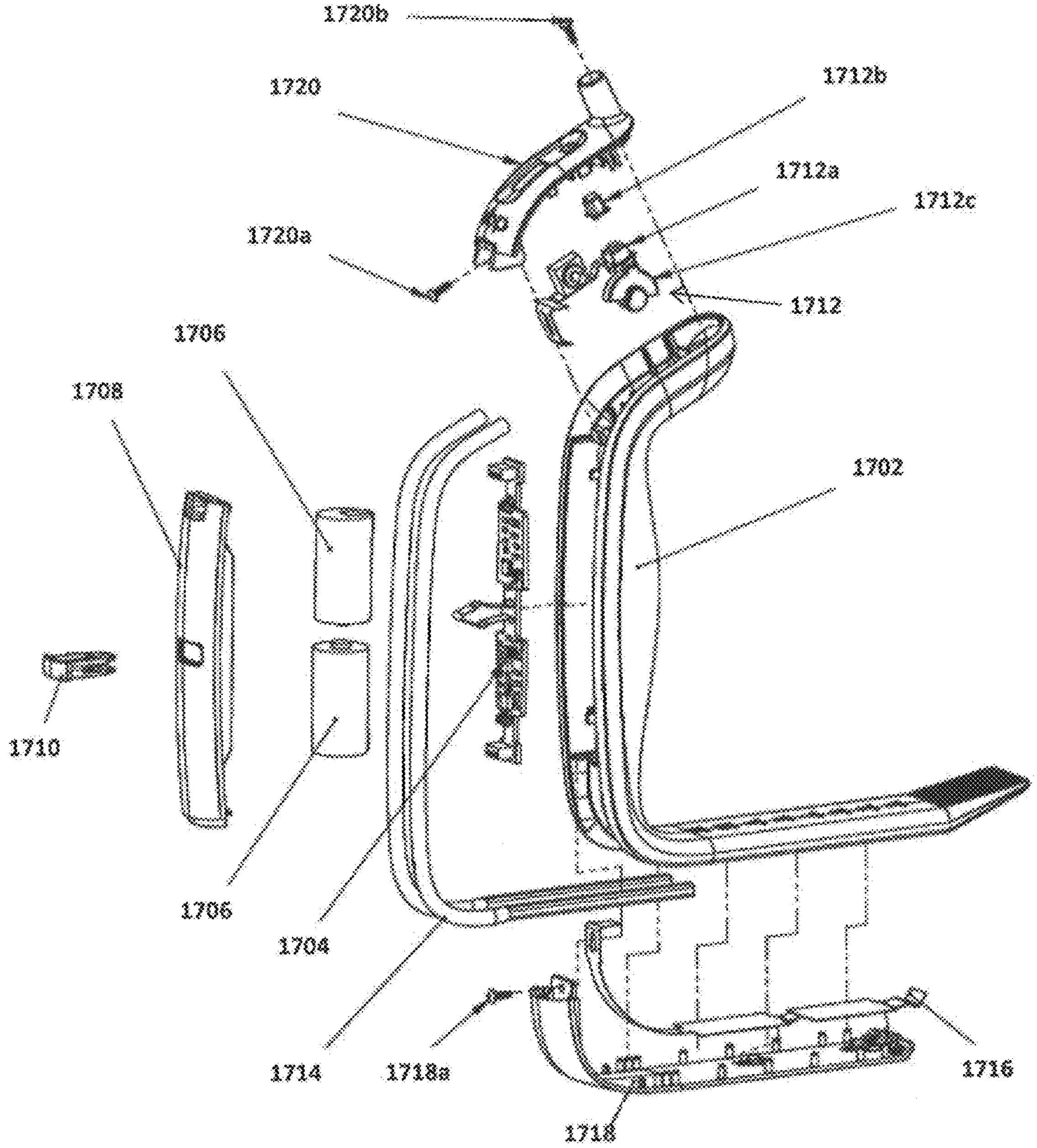
Figure 17C:
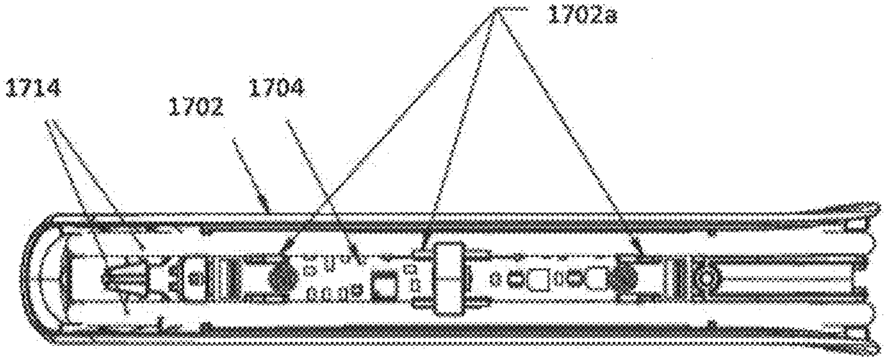
FIGS. 17C-17D show an internal view of the handle portion of the retractor of FIGS. 17A-B in an assembled state.
Figure 17D:
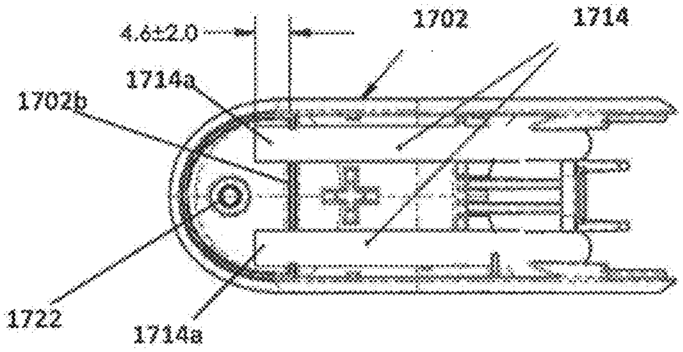

FIGS. 17A and 17B show an exploded view of a retractor 1700 of the third and fourth embodiments of the present invention, and FIGS. 17C-17D show an internal view of the handle portion of the retractor in an assembled state. As shown in FIGS. 17A-B, the retractor 1700 includes the blade portion and the handle portion 1702, with the handle enclosing a push tab assembly. The push tab assembly includes a PCB assembly 1704, a power source, such as one or more batteries 1706, a battery door 1708, and a push tab 1710. The push tab assembly may also include, or may be electrically coupled to, an operating assembly 1712 for controlling the light sources (LEDs). In certain embodiments, the operating assembly includes a circuit, such as a flex circuit 1712*a*, for the controls, a button 1712*b* or another type of switch, and a wheel 1712*c* or a slide-type switch. These operating members are described herein above with respect to the embodiment shown in FIGS. 1-8 and their operation is similar or substantially the same as in the embodiment shown in FIGS. 1-8. Therefore, detailed description thereof will be omitted.

As shown in FIG. 17B, the retractor 1700 also includes a curved end cover 1720 which includes a suction or vacuum port and openings for accommodating the operating members 1712*b*, 1712*c*. The curved end cover 1720 may be attached to the curved portion of the handle using screws 1720*a*, 1720*b*, as shown in FIG. 17B, or using any other suitable fasteners or fastening assembly. For example, the curved end cover 1720 may be attached to the curved end of the handle portion by press-fitting posts or pins provided on one of the curved end cover and the curved end with corresponding openings provided on the other of the curved end cover and the curved end of the handle, which may have corresponding shapes or different shapes, similar to the press-fitting of the blade cover to the blade portion described herein above.

As shown in FIGS. 17A-B, the retractor 1700 further includes the pair of tubes 1714 which correspond to the tubes 1402 in FIGS. 14A-B, an LED flex circuit 1716 and the blade cover 1718. The LED flex circuit 1716 in FIG. 17A corresponds to the LED flex circuit 1404 in FIGS. 14A-B and in FIG. 17B, corresponds to the modified LED flex circuit 1500*b* of FIGS. 15B-C and 16A-D. The blade cover 1718 of in FIGS. 17A-B corresponds to the blade cover 1406 in FIGS. 14C-D and to the blade cover 1606 in FIGS. 16A-D. As shown in FIG. 17B, the blade cover 1718 may be coupled to an end of the LED flex circuit 1716 and to the blade or the handle using a screw 1718*a* or using any other suitable fastener.

FIGS. 17C and 17D show the internal configuration of the handle portion of FIGS. 17A-B in an assembled state. As shown in FIGS. 17C and 17D, the PCB assembly 1704 is first positioned within the handle portion 1702 and thereafter the tubes 1714 are placed on top of the PCB assembly so that the tubes 1714 overlap with the sides of the PCB assembly 1704. The internal surface of the handle portion has ribs or projections 1702*a* projecting therefrom. The ribs 1702*a* are used for positioning the PCB assembly within the handle portion 1702 and for securing the tubes 1714 over the PCB assembly 1704. As shown in FIG. 17C, the tubes 1714 are pressed between the ribs, which hold the tubes in place and secure the PCB assembly 1704 in place within the handle portion.

FIG. 17D shows the internal configuration of the handle's curved end in an assembled state. As shown in FIG. 17D, the ends 1714*a* of the tubes 1714 are inserted and pinched by internal ribs 1702*b* formed within the handle. As described in more detail below with respect to FIGS. 24A-D, the curved end cover has similar internal ribs formed thereon which correspond to the internal ribs 1702*b* and which interact or engage with the internal ribs 1702*b* and also pinch the ends 1714*a* of the tubes 1714 so as to form a sealed chamber 1722 within the handle's curved end. In this way, smoke, fluids and/or debris conveyed from the operating site via the tubes empty out into the sealed chamber 1722 and are sucked out from the retractor via a suction or vacuum port (not shown).

Figure 18:
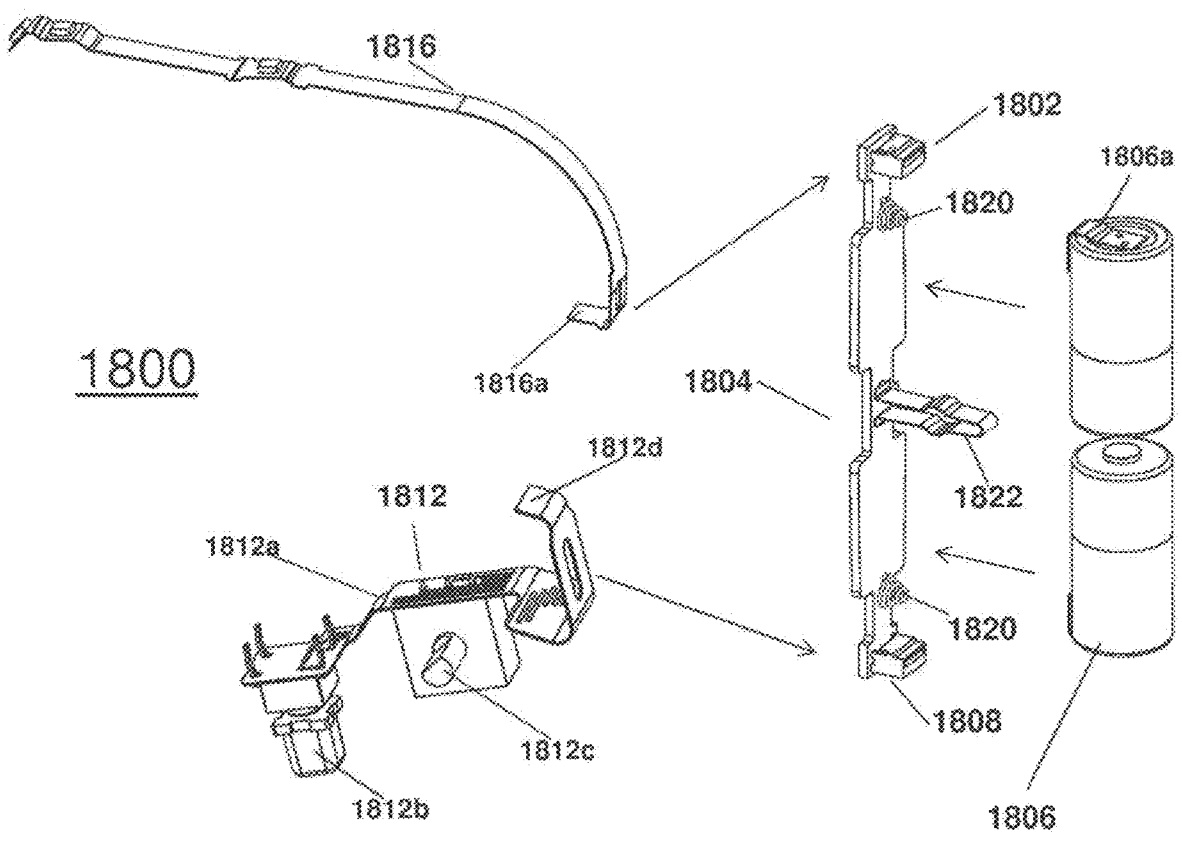
FIG. 18 shows power connections among different components of the retractor of FIGS. 17A-B.

The details of the LED flex circuit 1716, as well as the power connections among the LED flex circuit 1716, the PCB assembly 1704, the batteries 1706, and the operating assembly 1712 will now be described with reference to FIG. 18. Although FIG. 18 shows the LED flex circuit 1404 of FIGS. 14A-B, it is understood that the modified LED flex circuit 1500*b* of FIGS. 15B-C and 16A-D may be used instead. The LED flex circuit 1500*b* of FIGS. 15B-C and 16A-D has similar electrical connections, e.g., exposed conductive traces, to be connected with the PCB assembly.

The LED flex circuit, as used in the retractor assemblies described herein, is a custom-fabricated circuit that is used to connect LEDs mounted thereon to a control PCB, i.e., PCB assembly. As described above, the function of the LED flex circuit is to allow for the use of surface-mounted LED packages on a circuit board substrate and to eliminate all single-conductor wires, thus improving ease of assembly. Although FIG. 18 shows the LED flex circuit similar to the one shown in FIGS. 14A-B, it is understood that the LED flex circuit 1500*b* of FIGS. 15B-C and 16A-D may instead be used herein.

As shown in FIG. 18, a rear end (proximal end) of the LED flex circuit 1816 has bare exposed conductive traces 1816*a* that are inserted into a first flex circuit connector 1802 mounted on the PCB assembly 1804. As described above, the distal end of the LED flex circuit 1816 includes one or more LEDs mounted thereon for illumination. To power the LEDs on the LED flex circuit 1816, one or more batteries 1806 are connected to the PCB assembly 1804 via springs 1820 or similar electrical contacts and a central contact 1822. The springs 1820 hold the batteries 1806 in place against a cover 1708 shown in FIG. 17, and electrically connect to the batteries 1806 via electrical connection plates 1806*a*, each of which is coupled to a battery terminal, or via similar electrical connections. The central contact 1822 provides electrical conductivity between the batteries. The springs 1820 and the central contact 1822 are also mounted on the PCB assembly 1804. It is to be noted that the particular size and shape of the central contact 1822 as shown in these figures are not intended to be limiting. Various other designs of the central contact may be incorporated without departing from the scope of the present invention.

The PCB assembly 1804 modulates power to the LEDs based on a number of different modes and brightness/color settings. These settings are controlled via the operating assembly 1812, which is also connected to the PCB assembly 1804 via a second flex circuit connector 1808. The second circuit connector 1808 is also mounted on the PCB assembly 1804. As shown in FIG. 18, the operating assembly 1812 includes a flex circuit 1812*a* with operating members mounted thereon, and the operating members can be operated by a user to change the mode and brightness/color settings. The flex circuit 1812*a* has a connecting portion 1812*d* which is adapted to connect with the second flex circuit connector 1808. In FIG. 18, the operating members include a button 1812*b* and a potentiometer 1812*c*, and when assembled in the handle portion, an outer portion of the button 1812*b* and an outer portion (not shown in FIG. 18) of the potentiometer 1812*c*, e.g., a slide or a rotary switch, are exposed through the handle portion to allow operation by a user. The assembled view of the handle portion with the button and the potentiometer can be seen, for example, in FIG. 13. As discussed with respect to the other embodiments, the button 1812*b* may be operated to control the ON/OFF states of the LEDs, for example, in a predetermined sequence, and/or may be used for selecting a particular mode. The potentiometer 1812*c* may be operated to adjust the brightness of the LEDs in the ON state and/or to adjust the color/hue of the light emitted by the LEDs and/or to adjust the angles of the LED(s). Other controls may be performed by the button 1812*b* and the potentiometer 1812*c*. Moreover, as discussed above, other types of operating members, such as a combination of a switch, a button and/or potentiometer, may be used in the retractor.

When each of the above components are assembled, the LED flex circuit 1816 is positioned mostly along the blade portion of the retractor, the PCB assembly is positioned mostly within the handle portion of the retractor, and the operating assembly 1812 is positioned mostly within the curved end portion of the retractor. However, these configurations are also not intended to limit the scope of the present invention and they may vary among various versions and variations without departing from the scope and spirit of the present invention. For example, in some versions, the operating assembly 1812 may be provided in other portions of the handle, e.g., near the proximal end of the handle.

Figure 19:
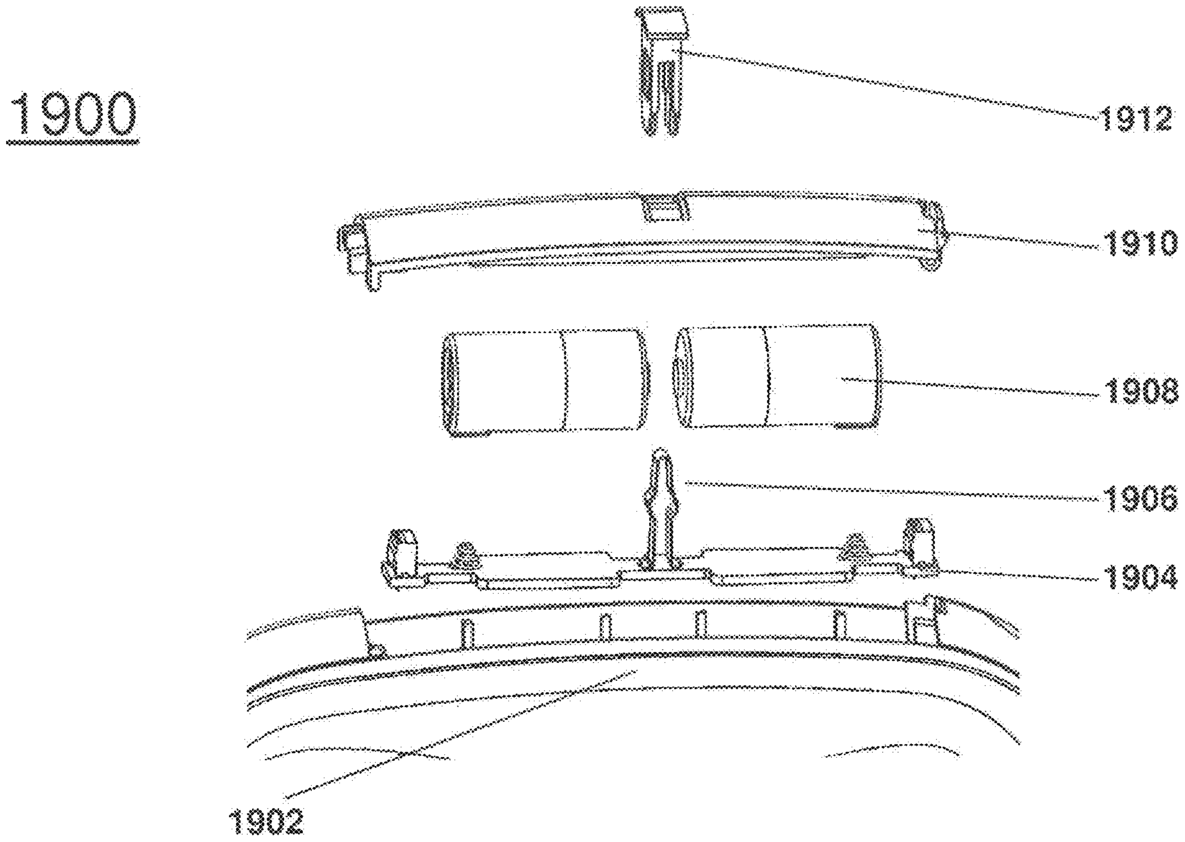
FIG. 19 shows an exploded view of a push tab assembly of the present invention.

The details of the push tab assembly will now be described with reference to FIGS. 19-21. During storage of retractors, it is often best to have the power source, i.e., batteries, disconnected from other circuitries in the retractor in order to maintain charge and also to abide by shipping regulations. In other medical devices, such as vaginal speculums disclosed in US Pub. No. 2015/0289757, a "pull tab" (e.g., a plastic strip) is used to separate the battery terminal from electrical contacts during storage. In these devices, the pull tab is pulled out just before use to establish electrical continuity. However, this method may not suitable for the retractor design because the slot remaining after the pull tab has been removed constitutes a point of ingress for fluids, which could negatively affect the retractors during use. There is also a risk during surgery that a pull tab may not be disposed properly, and could inadvertently end up inside a patient.

In accordance with the present embodiment, a "push tab" is provided in place of the "pull tab," which is inserted (or pushed in), instead of pulled out, in order to establish an electrical connection of the power source with the associated circuitry. When the push-tab is inserted or pushed in, the resulting exterior surface will not be open to ingress of fluids or debris because the push-tab covers and seals the opening created for the push-tab. Although the present embodiment describes the push tab as being pushed into the handle of the retractor to establish an electrical connection, in some versions, the push tab may be pushed or slid sideways from a storage or disconnected position to an in-use or connected position. In other configurations, the push tab may be replaced by a pull tab mechanism which is pulled in order to establish electrical connection while also blocking any openings that would otherwise provide a way for fluids or debris to get into the retractor.

Returning now to FIG. 19, an exploded view of each of the components of a push tab assembly 1900 of the present embodiment is provided. The push tab assembly 1900 includes the PCB assembly 1904, the central contact 1906 mounted on the PCB assembly 1904, the power source, such as one or more batteries 1908, a battery cover 1910 and a push tab 1912. The batteries 1908 rest on the PCB assembly 1904 and are locked in place within the retractor handle portion by the battery cover 1910. The central contact 1906 is positioned on the PCB assembly 1904 at a particular location which enables the central contact 1906 to serve as a conductor of electricity between the batteries. In other versions, the central contact 1906 may be positioned at another location of the PCB assembly 1904 so as to separate at least one battery terminal from the remainder of the circuit. The push tab 1912 is positioned over the central contact 1906 such that when the push tab 1912 is inserted into the push tab assembly, the push tab 1912 either partially overlays or fully overlays the central contact 1906 and either permits or blocks the flow of electricity within the push tab assembly 1900 depending on the amount of insertion into the push tab assembly. Finally, the battery cover 1910 comprises an opening to allow insertion of the push tab 1912 into the push tab assembly.

It is to be noted that each of these components of the push tab assembly are designed in a way such that when these components are fully assembled together within the handle portion of a retractor, the battery cover 1910 and the push tab 1912 (in the "use" position, to be further described herein) can create a fluid-tight seal on the handle portion 1902 to prevent any fluid from entering into the retractor during use.

Figure 20A:
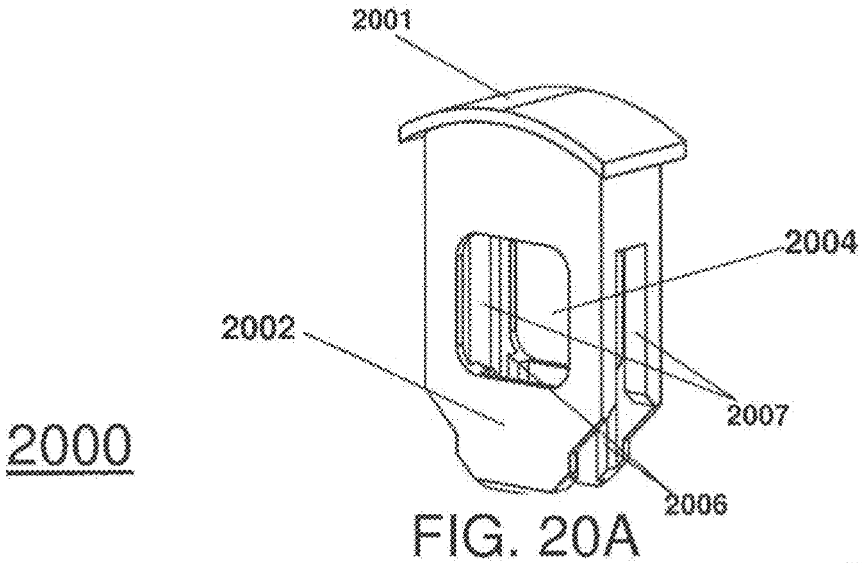
FIGS. 20A-20D show various views of a push tab included in the push tab assembly of FIG. 19.
Figure 20B:
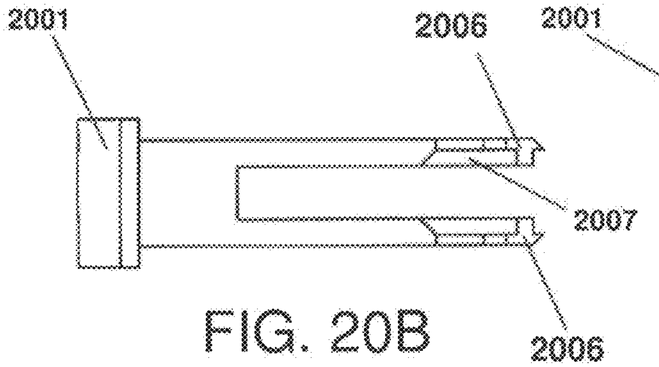
Figure 20C:
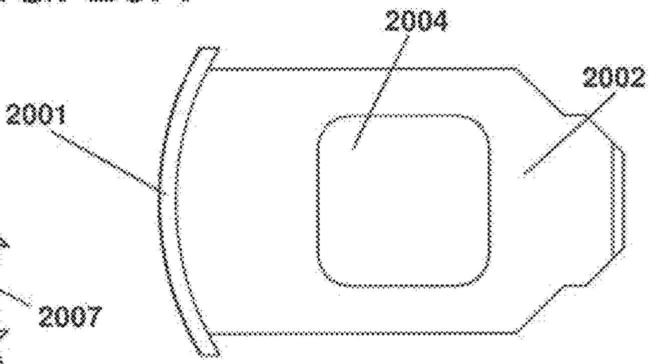

FIGS. 20A-20D illustrate various views of a push tab 2000, which corresponds to the push tab 1912 described with reference to FIG. 19 above. FIG. 20A is a perspective view of the push tab 2000 showing the push tab 2000 having a top surface 2001 which is adapted to be operated by a user to push in the push tab, and pair of side surfaces 2002, forming a pair of side legs, each having a respective open area 2004 (a front view of one of these side surfaces 2002 is shown in FIG. 20C). The top surface 2001 of the push tab 2000 is configured so that when the push tab is fully inserted into the push tab assembly, the top surface seals the opening in the battery cover to prevent fluids from entering the handle portion through the opening in the battery cover. The side surfaces 2002 are at least partially made of dielectric or other non-conductive materials. For example, these side surfaces (or at least the lower portions of these side surfaces) are plastic or polymer surfaces designed to prevent electric current from flowing between the batteries. In some embodiments, the side surfaces may be coated with electrically insulating materials. The open area 2004 is sized to receive either a respective terminal of the batteries or a respective portion of a central contact mounted on a PCB assembly.

Figure 20D:
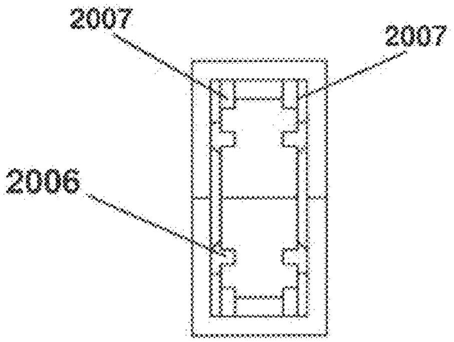

As discussed herein, the push tab 2000 is adapted to be assembled directly over a central contact 1906 of a PCB assembly and to engage with the central contact. In other words, when assembled, the push tab 2000 directly overlays or surrounds the central contact. As shown in FIG. 20B, which shows a cross-sectional view of the push tab 2000 and in FIG. 20D, which shows a bottom view of the push tab 2000, the push tab 2000 further comprises a set of internal ribs 2006, with a pair of internal ribs 2006 protruding from each side surface 2002 at a location offset from each side edge of the side surface 2002. As can be seen in FIGS. 20A and 20D, another pair of protruding ribs 2007 may be formed on each side surface along each side edge of the side surface 2002. The internal ribs 2006 guide the push tab 2000 relative to the central contact. Specifically, the internal ribs 2006 guide the push tab 2000 to be pushed into, or pulled out of, the retractor handle portion with respect to the central contact and prevent lateral shifting of the push tab 2000. For example, the push tab 2000 can slide between one of at least two configurations: (1) a "storage" configuration; and (2) a "use" configuration. In the first "storage" configuration, the push tab 2000 is partially inserted into the retractor handle portion such that the push tab 2000 partially overlays the central contact and a top surface 2001 of the push tab 2000 projects from the surface of the handle. More specifically, in the storage configuration, the non-conductive portion of the push tab 2000, i.e., the side surfaces 2002, is in contact with, and separates, the battery terminals from the central contact, so that the batteries are disconnected electrically from the circuitry of the retractor. This configuration is more clearly illustrated in FIG. 21A. Although not shown in FIGS. 20A-20D, the side surfaces 2002 of the push tab 2000 may also include one or more projections or bumps on their outer-facing surfaces for assisting in retaining the push tab 2000 in the storage configuration before being pushed in and in the use configuration after being pushed in. For example, a first set of bumps may be provided on the outer surface of the side surfaces 2002 on one or both sides of the opening 2004, e.g., about mid-way along the height of the push tab. The first set of bumps would retain the push tab 2000 in the storage configuration and prevent the push tab 2000 from being accidentally pressed in while the retractor is stored or being transported. A second set of bumps may be provided near on the outer surface of the side surfaces 2002 closer to the top surface 2001 for retaining the push tab in the use configuration after being pushed in. The second set of bumps also prevents the push tab from being removed from then handle after being pushed into the use configuration.

Figure 21A:
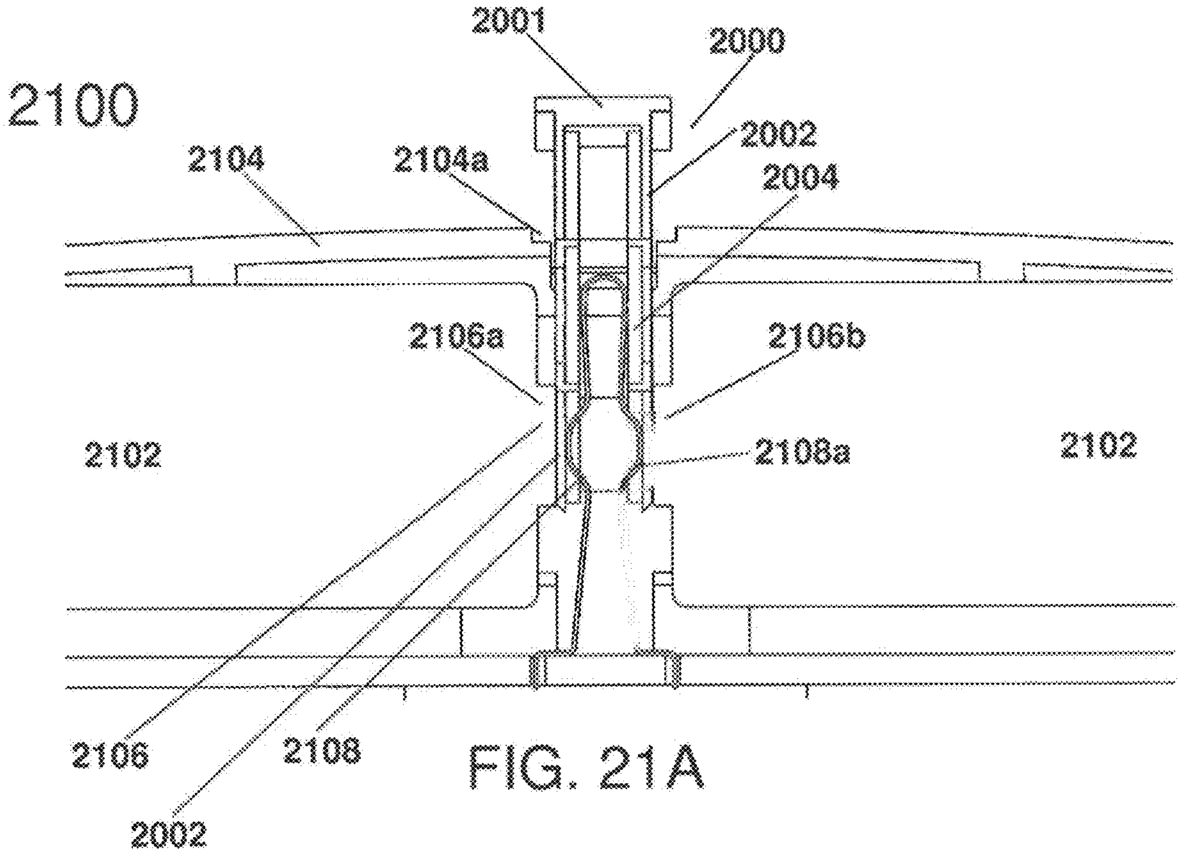
FIGS. 21A-21B show the push tab assembly of FIG. 19 in an assembled state in a "storage" configuration and in a "use" configuration, respectively.

As shown in FIG. 21A, the batteries 2102 are in place within the retractor handle portion and are secured by a battery door 2104. In FIG. 21A the respective battery terminals 2106*a*, 2106*b* of the batteries 2102 are prevented from being in electrical contact with the central contact 2108 by the side surfaces 2002 of the push tab 2000, which is partially inserted into an opening 2104*a* in the battery door 2104. In this configuration, protruding portions 2108*a* of the central contact 2108 are compressed toward each other and bias against the non-conductive side surfaces 2002 of the push tab 2000, while the open areas 2004 in the side surfaces are located above the protruding portions 2108*a* and are covered by internal sidewalls of the cover 2104. Thus, the circuit is open and electricity cannot flow from the batteries to other components of the illumination assembly. The biasing force of the protruding portions 2108*a* of the central contact against the side surfaces 2002 of the push tab 2000 prevents the push tab 2000 from being accidentally pushed in or pulled out during transport of the retractor.

Figure 21B:
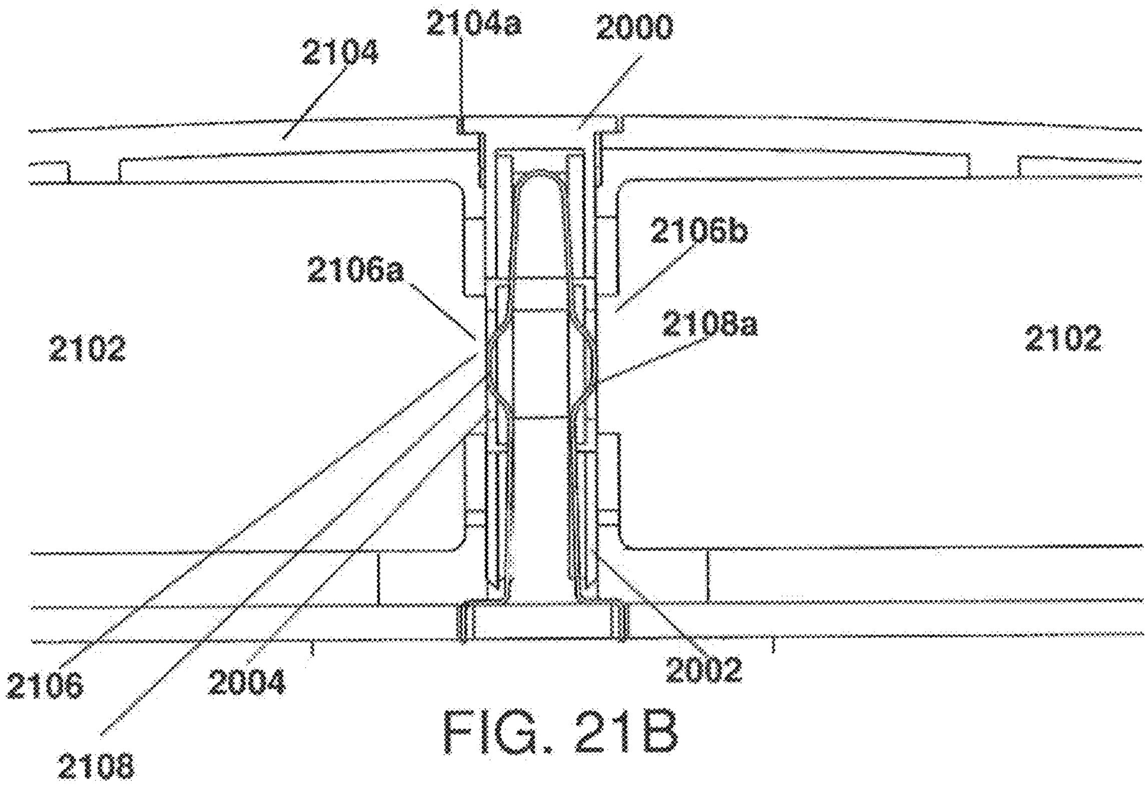

In the second "use" configuration, the push tab 2000 is fully inserted into the retractor handle portion such that the push tab 2000 completely overlays or engulfs the central contact 2108. More specifically, in the "use" configuration, a portion of the central contact 2108 protrudes through the respective open areas 2004 in the side surfaces 2002 of the push tab 2000 and is in direct contact with the battery terminals 2106*a*, 2106*b*. This configuration is more clearly illustrated in FIG. 21B. As shown in FIG. 21B, the battery terminals 2106*a*, 2106*b* are in direct contact with the central contact 2108, as the protruding portions 2108*a* of the central contact 2108 protrude through the respective open areas 2004 in the side surfaces 2002 of the push tab 2000. In the "use" configuration, the circuit is closed and power can be delivered from the batteries to the other components of the illumination assembly of the retractor. The protruding portions 2108*a* of the central contact 2108 bias in an outward direction against the batteries and/or against the battery terminals 2106*a*, 2106*b* so as to ensure electrical contact with the battery terminals and to prevent easy removal of the push tab 2000 from the opening in the cover. The specific configuration of the central contact 2108 engaging with the side surfaces of the push tab 2000 also makes it difficult if not impossible to remove the push tab 2000 after it is fully inserted, thus preventing multiple uses of the retractor and resulting in a fully disposable retractor configuration. However, in other versions, the central contact 2108 and/or the push tab 2000 may be configured to allow removal of the push tab 2000 or movement of the push tab back to the storage configuration in order to allow multiple uses of the retractor.

Moreover, as mentioned herein, in the "use" configuration, the push tab 2000 is fully inserted through an opening 2104*a* formed in the battery door 2104 so as to create an air tight and/or a fluid tight seal that prevents any debris or fluid from entering the interior of the retractor. As can be seen in FIGS. 21A and 21B, the opening 2104*a* is shaped to correspond to the shape of the push tab 2000, so that the top surface 2001 of the push tab 2000 fits into an outer portion of the opening 2104*a* to cover and seal off the remaining portion of the opening 2104*a* and to prevent any debris or fluids from entering the retractor handle.

In some versions, the push tab 2000 and the internal ribs 2006 of the push tab 2000 are configured with a spring force to alternate between use and storage configurations. For example, the push tab assembly may first be assembled and locked in a storage configuration. The user would then use force to push the push tab 2000 into the retractor so as to release the storage configuration, to move the push tab to the use configuration and to lock the push tab 2000 in the use configuration. Thereafter, if needed, the user may push the push tab 2000 again, or pull the push tab out, to set the push tab 2000 into the storage configuration. In another version, the push tab contains retaining latches to prevent accidental removal from the handle, thus preventing small loose components from the operating room.

Figure 22A:
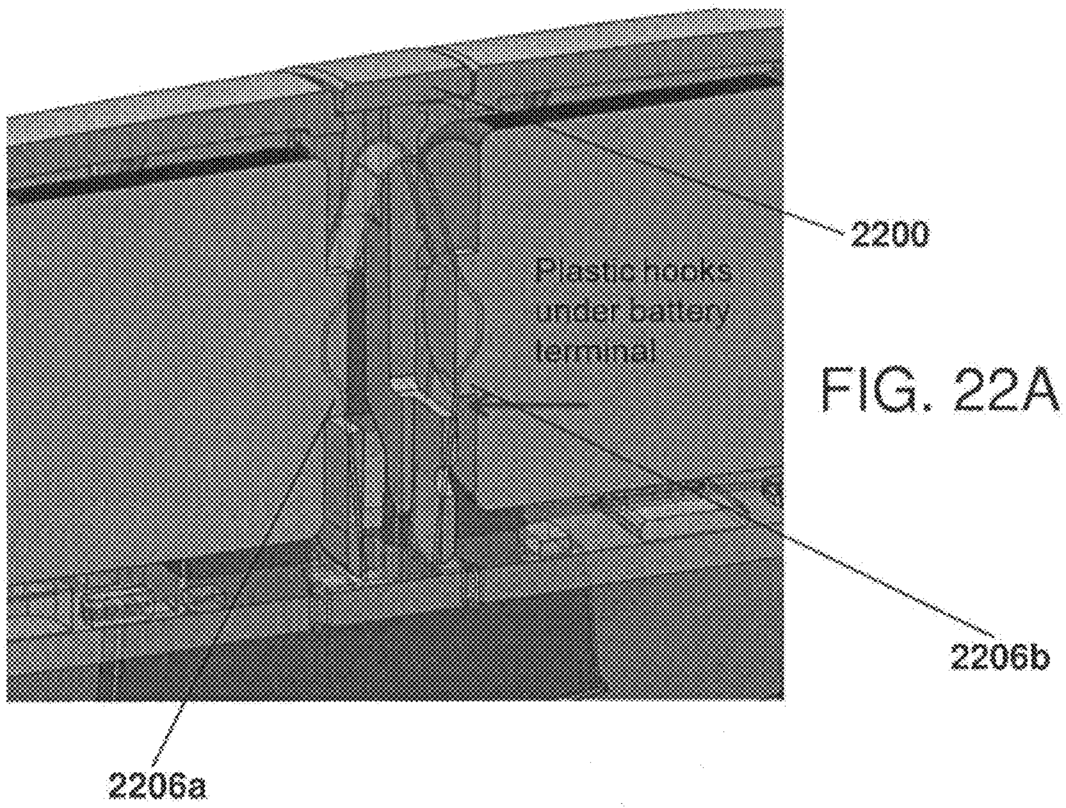
FIGS. 22A-22C show views of an exemplary push tab assembly configured to assist in removal of batteries from the handle.
Figure 22B:
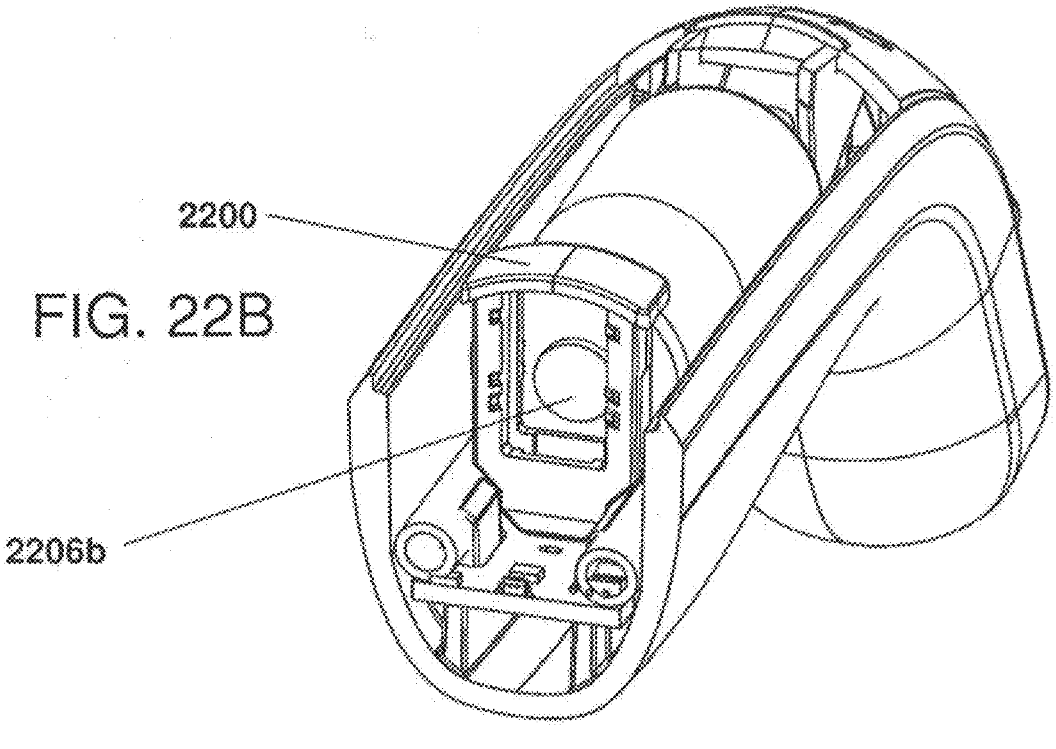
Figure 22C:
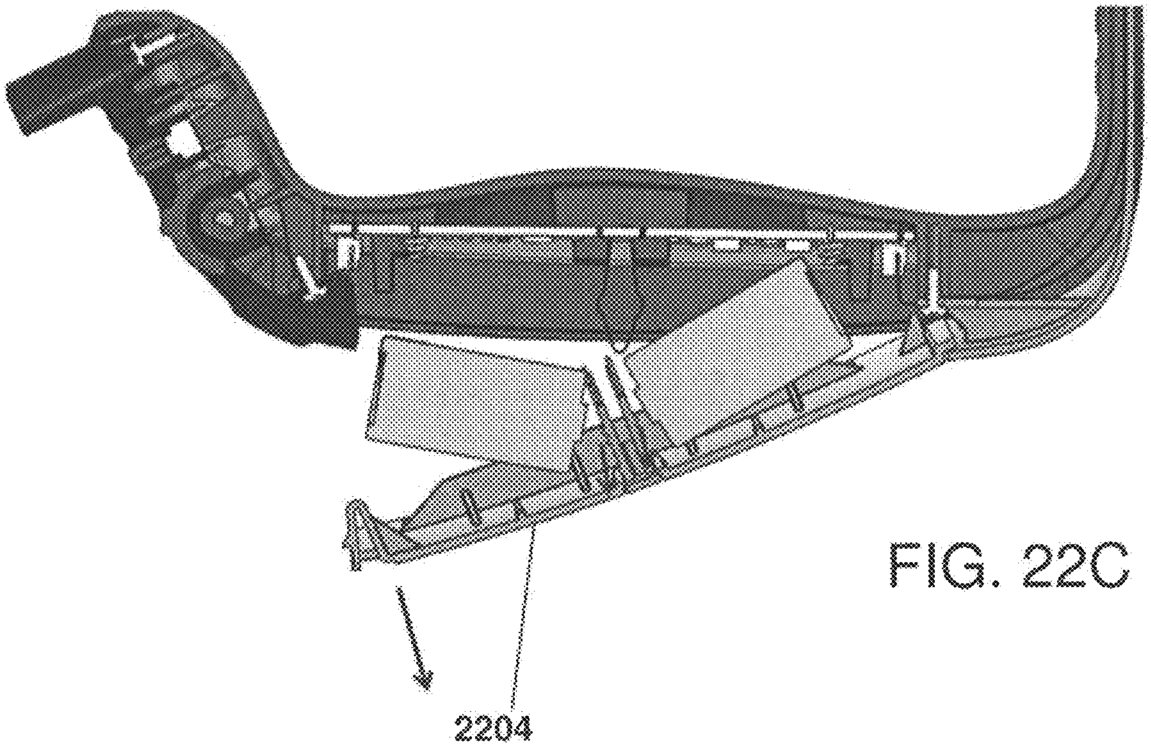

In some versions of the present embodiment, the push tab is configured to cause removal of batteries from the handle of a retractor (e.g., a battery chamber) when the cover or the battery door is opened. As described herein, due to the shape and configuration of the push tab, the primary function of the push tab is to provide an electrical separation between the batteries and the PCB circuit board during storage or transport (i.e., storage configuration) and to electrically connect the batteries with the PCB circuit board during operation in a fully seated or pushed-in position (i.e., use configuration). In addition, as illustrated in FIGS. 22A-22C, the push tab also assists in removal of the batteries from the battery compartment when the battery cover or battery door is opened so that the user of the retractor would not come into physical contact with the batteries in order to remove them. This way, the batteries are free from contamination by biological materials which may be present on the user's hands or gloves and which may be present on the surface of the retractor after use. This allows the batteries to be removed easily, even if the user is wearing gloves, so they can be reused or recycled separately from the retractor. For example, as shown in FIG. 22A, when the push tab 2200 is fully seated (or fully pushed into the retractor), the legs of the push tab hook around and/or under a battery terminal of the respective battery. In other words, as previously shown in FIG. 20C, the open area 2004 of the push tab 2000 receives the battery terminals and once received, the side legs of the push tab overlap with the battery terminals in the terminal thickness direction. FIGS. 22A and 22B show that the open area 2004 formed in the legs of the push tab 2000 is sized so that when the push-tab is in the fully seated position, the battery terminals 2206*a* and 2206*b* are received (or overlapped) inside the open area 2004 of the push tab 2200. Thus, when the battery door 2204 is opened (shown in FIG. 22C), the push tab 2200 is pulled away from the handle together with the battery door 2204 and the legs of the push tab 2200 hook onto or engage with the terminals of the batteries so as to force the batteries to fall out of the retractor through the opening previously covered by the battery door 2204. In one version, the battery door 2204 opens by hinging on one side while, in another version, the battery door 2204 fully detaches from the retractor and causes the batteries to detach from the retractor as well. It is noted that when the push tab is in the "storage" configuration, i.e., the push tab is only partially inserted, the battery terminals are pressed against the side surfaces of the push tab and, hence, the battery terminals are not hooked inside the open area of the push tab. When the battery door is opened in the "storage" configuration, the push tab may not cause the batteries to drop out from the battery compartment of the retractor.

Figure 23A:
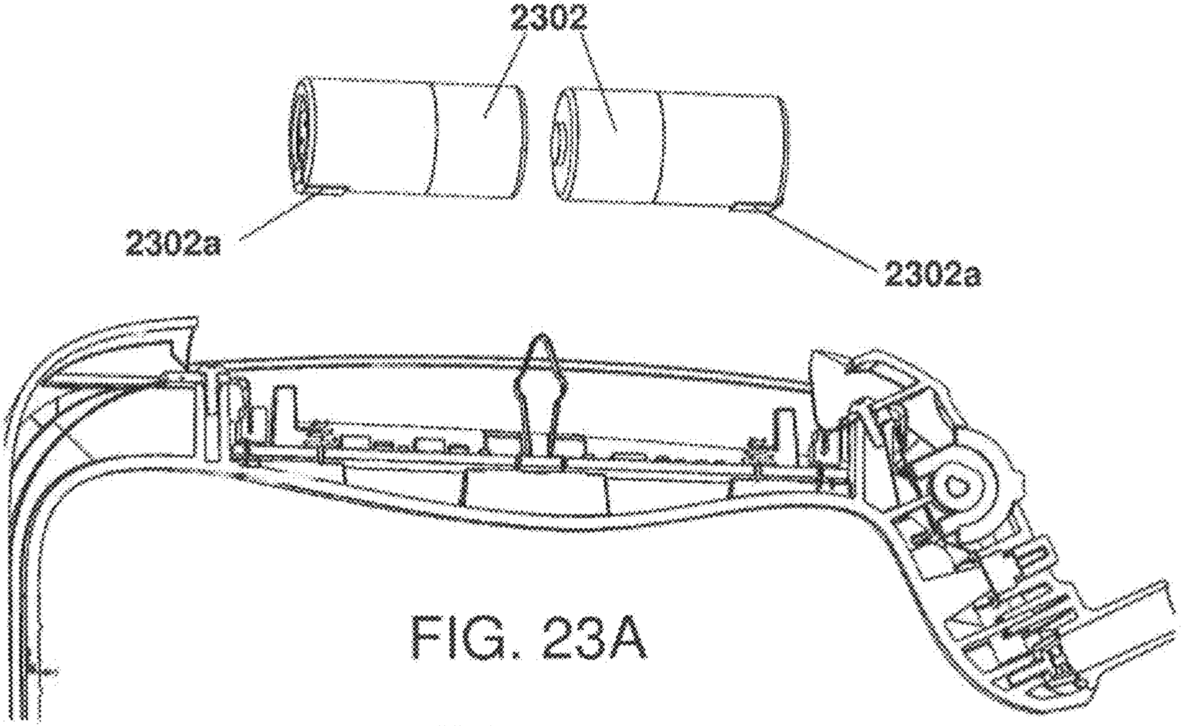
FIGS. 23A-23B show views of the retractor of FIGS. 17A-B and of the push tab assembly of FIGS. 19-22 with unique batteries.
Figure 23B:
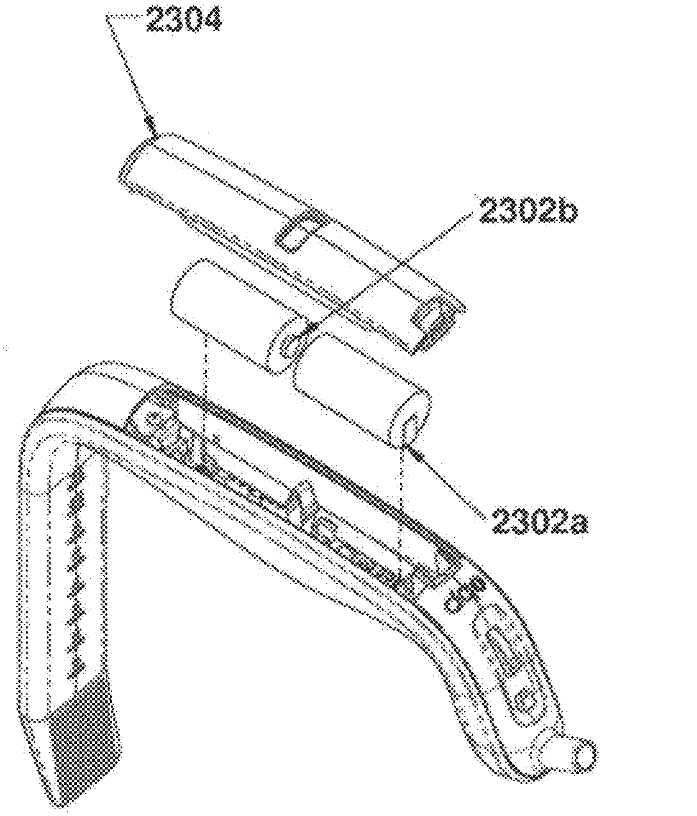

To facilitate the battery removal feature of the present embodiment, the batteries may be configured in a unique way. For instance, as shown in FIGS. 23A-23B, the two batteries are positioned so that their respective positive terminals face each other. This way, the positive terminals of the batteries are received into the open areas of the push tab, as described above, during the "use" configuration. In an alternative version, only one battery may have its positive terminal received inside an open area of a push tab, and once the one battery is removed upon opening of the battery door (i.e., by the push tab hooking under the positive battery terminal), the central contact no longer applies a biasing force to the remaining battery and this lack of biasing force would cause the remaining battery to drop out from the retractor.

In certain versions, the batteries are configured with a one-time use tab which limits their use to only one time, thus preventing reusing of the batteries in retractors and making them truly disposable. FIGS. 23A and 23B shows that the batteries 2302 are configured with a respective one-time use tab 2302*a*. These one-time use tabs 2302*a* are providing at the negative terminals of the batteries and extend from the terminal ends to the sidewall of the battery so as to provide a terminal connection on the side of the battery. Since the push-tab assembly requires the unique batteries of FIGS. 23A-B, which have the one-time use tabs 2302*a* in order to form an electrical connection with the PCB circuit board, conventional batteries cannot be used in the retractor and thus, the batteries in the retractor cannot be easily replaced. Moreover, the custom batteries are non-rechargeable which also limits the retractor to single use. In some embodiments, the custom batteries may have a custom size or be non-standard or uncommon size batteries in order to prevent re-using of the retractor.

Handle End Assembly for Improved Smoke, Fluid and Debris Removal

With respect to the smoke evacuation system, the third and fourth embodiments of the retractor employ tubing extending from the blade portion to the distal end of the handle portion for conveying smoke, fluids and debris to a suction or vacuum port formed at the end of the handle portion. Although not shown in FIGS. 1-8, similar tubing may be used in the retractors of the first and second embodiments. The tubes of the smoke evacuation system may be made from flexible materials, such as PVC or other suitable plastic and polymer materials. In some embodiments, the tubes may be directly coupled to the vacuum or suction port formed at the end of the handle portion, e.g., formed in the curved end cover of the handle portion.

However, direct connection of the tubes to the port may result in a more complex assembly of the smoke evacuation system. Therefore, in some embodiments, the tubes of the smoke evacuation system terminate before reaching the vacuum or suction port.

In some embodiments, the tubes of the smoke evacuation assembly can be held by internal ribs or projection formed within the handle portion and/or within the curved end of the handle portion in order to keep them in place. In addition, some embodiments of the invention provide additional ribs or projections in or near the curved end of the handle to create a sealed chamber in the curved end of the handle into which the tube ends open and which includes the vacuum or suction port. Specifically, the tubes can be pinched or squeezed from all directions by the ribs or projections formed within the handle portion or within the curved end of the handle portion so as to create an air tight seal and to form the sealed chamber.

Figure 24A:
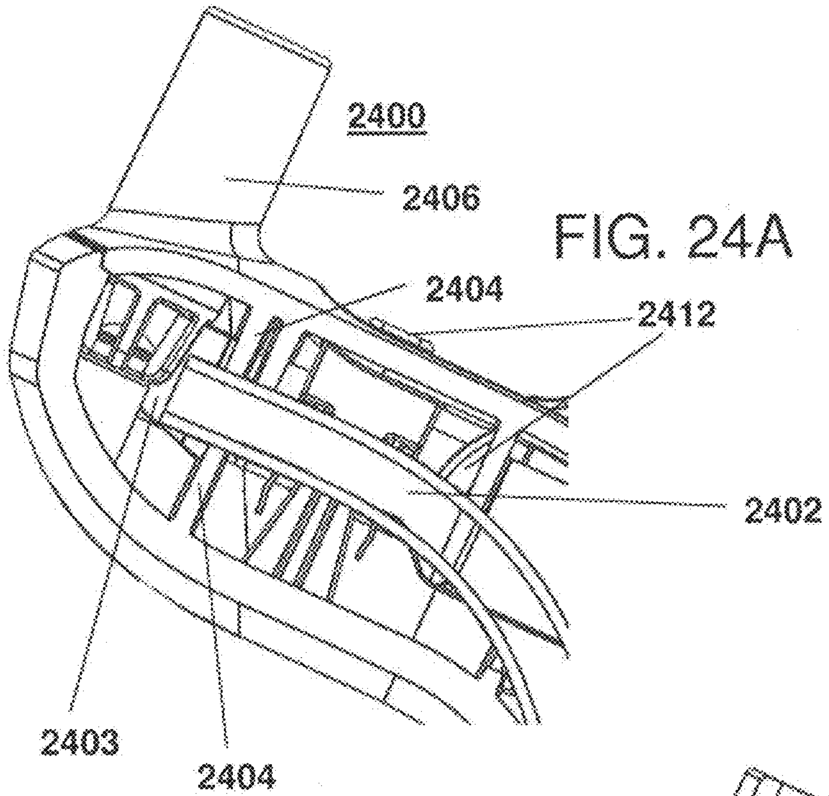
FIGS. 24A-24B show cross-sectional views of a distal curved end of the handle of the retractor o FIGS. 13-23.
Figure 24B:
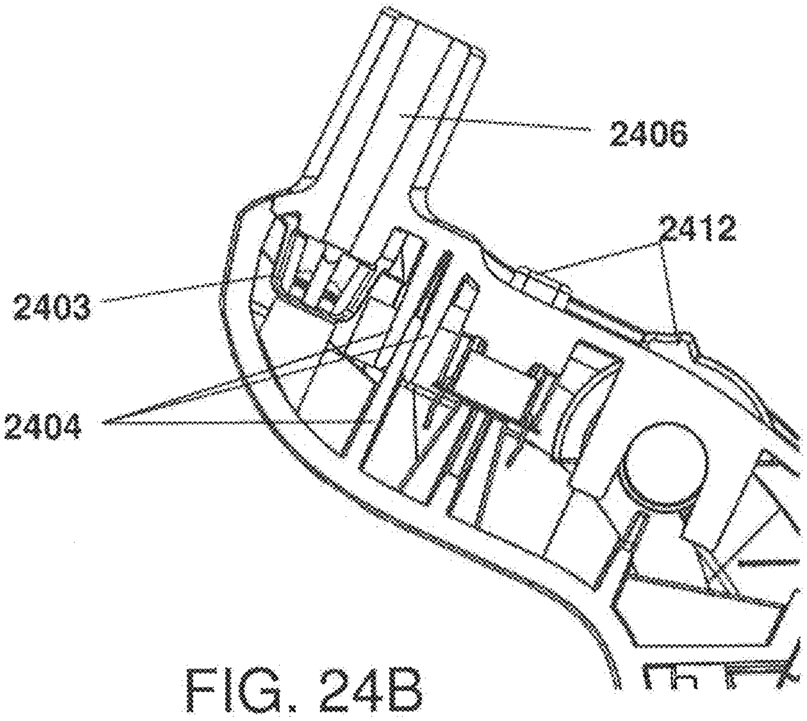

FIGS. 24A-24B show cross-sectional views of the distal curved end of the handle portion of the retractor shown in FIGS. 13-23. As shown in FIGS. 24A-24B, the smoke evacuation tube 2402 of the retractor 2400 extends into the far distal end of the handle portion (e.g., the curved end portion) and the smoke evacuation tube 2402 is squeezed or pinched by the internal ribs 2404 formed internally in the handle portion and the curved end portion cover so as to provide an airtight seal around the smoke evacuation tube 2402. As a result, the distal end of the handle portion forms the sealed chamber 2403 at its end which is sealed off from the rest of the handle portion and the ends of the smoke evacuation tubes 2402 extend into the sealed chamber. As shown in FIGS. 24A-B, the sealed chamber 2403 formed by the internal ribs 2404 and the tubes pinched thereby is preferably positioned closer to the distal end of the handle portion than the operating assembly 2412 for controlling the light sources.

The smoke evacuation tubes 2402 terminate near the smoke evacuation port 2406 without having to be coupled directly to the smoke evacuation port 2406, and any smoke, fluids or debris are suctioned from the smoke evacuation tube(s) 2402 to the smoke evacuation port 2406 without escaping into other areas within the handle portion. The sealed chamber, thus, prevents other components within the handle, such as the PCB assembly, the batteries and the operating members for controlling the light sources, from being exposed to the smoke, fluid and debris conveyed by the smoke evacuation system. This configuration prevents short circuiting of the electrical components of the retractor and damage to these components by the smoke, fluids and debris. In addition, this construction with the sealed chamber 2403 eliminates the need for a direct connection between the port 2406 and the tubes 2404, which simplifies assembly of the smoke evacuation system into the retractor.

Figure 24C:
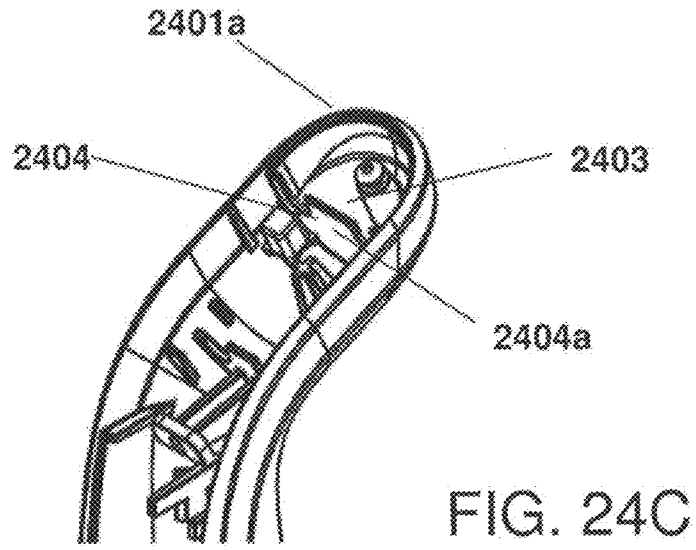
FIGS. 24C-24D show perspective views of the curved end of the handle and of the curved end cover, respectively.
Figure 24D:
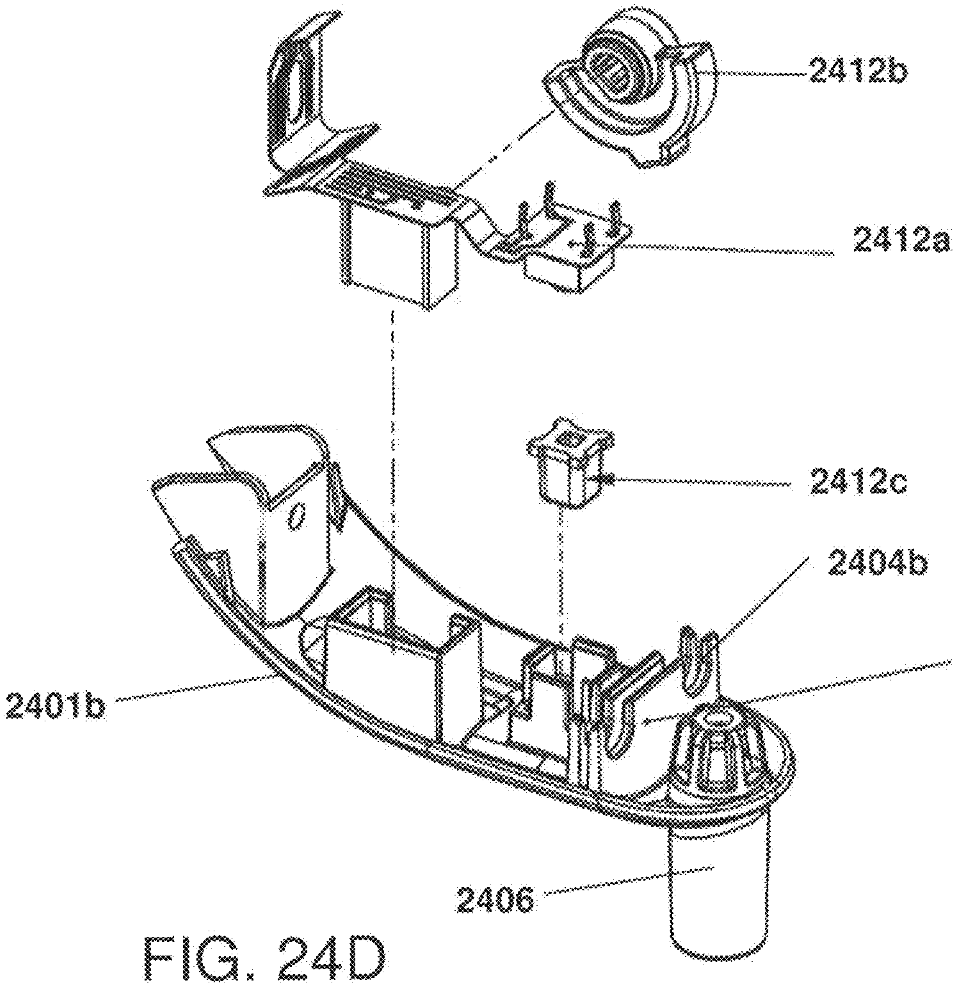

FIG. 24C shows a perspective view of the curved end portion 2401*a* of the handle portion to show its internal configuration, while FIG. 24D shows a perspective view of the curved end portion cover 2401*b* showing its internal configuration. The curved end portion cover 2401*b* couples to the curved end portion 2401*a* so as to form the distal end of the handle portion. As shown in FIG. 24C, the curved end portion 2401*a* of the handle portion includes internal ribs 2404*a* which form a part of the internal ribs 2404 when the curved end portion 2401*a* is assembled together with the cover 2401*b*. As can be seen in FIG. 24D, the cover 2401*b* includes internal ribs 2404*b* formed on its internal surface which form the other part of the internal ribs 2404 when the cover 2401*b* is assembled with the curved end portion 2401*a*. In the illustrative embodiment of FIGS. 24A-D, the cover 2401*b* has a pair of internal ribs 2404*b* and the curved end portion 2401*a* includes one set of internal ribs 2404*a* which is partially inserted between the pair of internal ribs 2404*b* on the cover 2401*b* in an assembled state. This creates an overlap between the internal ribs 2404*a* and 2404*b* that improves the sealing of the sealed chamber 2403 formed in the handle's distal end. As also shown in FIG. 24D, the operating assembly, including the operating circuit 2412*a*, the wheel controller 2412*b* of the potentiometer and the button 2412*c* is assembled into the curved end cover 2401*b* outside the sealed chamber 2403 formed by the internal ribs 2404. As further shown in FIG. 24D, the port 2406 may have a filter placed on the inside of the end cover 2401*b* covering the opening of the port 2406.

OTHER EMBODIMENTS

In accordance with the various embodiments that have been described herein, a retractor can include multiple light sources or LEDs for illuminating different areas around the retractor and the multiple LEDs can be individually controlled so as to provide flexibility to the user for illuminating specific areas of a patient's body during surgical procedures. As described herein, the light sources or LEDs on the retractor can be controlled so as to turn on and off only the desired light sources so as to illuminate some areas while not illuminating others. In addition, the brightness and color of the light sources or LEDs can be controlled individually so as to provide further flexibility. Moreover, the angles and/or positions of the light sources relative to the retractor blade may also be controlled either manually or via a controller. All of these features allow the user to direct appropriate illumination of the surgical areas without requiring additional equipment. Additionally, as described herein, the light sources or LEDs are integrated together with a smoke evacuation or suction assembly (e.g., through the use of tubes, the smoke evacuation port, and a vacuum source), and with the blade cover so as to minimize the profile or thickness of the blade and to hide any wiring required for the light sources or LEDs under the blade cover. The constructions described do not require additional elements or devices so as to avoid interference of the light sources or LEDs with patient's tissues and/or with the surgical field. As also described above, the number of light sources LEDs and their arrangement may be varied for different retractors and may depend on the areas where illumination is desired.

With respect to the blade cover that covers the LEDs and the smoke evacuation assembly, some variations of the embodiments disclosed herein may include a plurality round pins on the blade cover that are inserted into a plurality of hexagonal holes or openings in the retractor blade, as described above. Since the pins have a different shape from the holes, the pins may be made from a softer material so that the pins adapt to the shape of the holes. In some other variations, the blade cover has pins with a first shape or cross-section, while the openings in the retractor blade have a second shape, different from the first shape. This method of coupling increases the coupling strength between the blade and the cover and also increases the strength of the retractor blade. With the blade cover strengthening the retractor blade, the retractors embodying such feature are able to withstand higher amounts of force during use.

In further accordance with the various embodiments that have been described herein, a retractor can also include a non-slip pattern near the distal end of the blade. The present invention is particularly advantageous in this manner in that the non-slip pattern provides a preferential grip that assists in the particular application of the retractor.

Still further in accordance with the various embodiments of the present invention described herein, a retractor can include an improved flexible circuit board that provides advanced thermal dissipation. As discussed above, the flexible circuit board of the present invention has been modified in terms of size, shape and thickness to maximize copper coverage and optimize thermal dissipation of heat generated from the LEDs.

Moreover, in the accordance with various embodiments described herein, a retractor can include a push-tab assembly that prevents electric coupling of the batteries with one another and/or with the electrical circuit for powering the illumination assembly in one state (e.g., storage configuration) and allows electric coupling of the batteries with one another and with the electrical circuit in another state (e.g., use configuration). The push-tab assembly is configured to prevent debris and fluids from entering the internal components of the retractor, e.g., the handle of the retractor, particularly when in the use configuration. The push tab assembly is also configured to cause removal of the batteries contained in the battery compartment when the battery door including the push tab is removed from the retractor.

Other embodiments described herein include an ergonomic handle design that permits easy operation of multiple controllers provided at the distal end of the retractor handle using a user's thumb or pinky. Due to its unique shape, the control center of the retractor can be used like a joystick during operation. Specifically, the control center is offset from the central line or central plane of the handle and this configuration follows the contours of the user's finger, allowing for an easy access to the control center. The handle may also be configured so as to include a sealed chamber at its distal end which is used for connecting the tubes of the smoke evacuation system with the suction or vacuum port. This allows the smoke, fluids and debris to be isolated from the electrical components disposed within the retractor's blade and handle portions.

While various features and variations thereof have been described with respect to retractors, it is noted that one or more of the features described herein may be embodied within other medical devices which include a power source for use in an illumination assembly or for use in any other electrical assembly, including but not limited to speculums, anoscopes, laryngoscopes, suction devices, cannula and others. The specific configurations of the LED arrangement, flexible circuit board, or the push-tab assembly may be modified, as needed, for the specific device in which is it used.

In all cases, it is understood that the above-described arrangements are merely illustrative of the many possible specific embodiments which represent applications of the present invention. Numerous and varied other arrangements, including use of different materials and various configurations of components of the retractor, can be readily devised without departing from the spirit and scope of the invention.

We claim:

1. A surgical retractor comprising:

a blade having a first surface and a second surface opposite from the first surface, wherein the blade includes a main blade body forming the first surface and a blade cover covering at least a portion of the main blade body and forming the second surface; and a handle extending from a proximal end of the blade, wherein the first surface of the blade includes a non-slip texture having a preferential grip in a first direction corresponding to direction of extraction of the surgical retractor from an incision and having a minimal or no grip in a second direction opposite to the first direction and in a third direction transverse to the first and second directions, and wherein the blade is configured to accommodate at least one of a portion of an illumination assembly and a portion of a smoke evacuation assembly in a space formed between the main blade body and the blade cover.

2. The surgical retractor of claim 1, wherein:

the non-slip texture comprises a plurality of elongated rib projections extending in a width direction of the blade, and each of the elongated rib projections is inclined in a direction away from a distal end of the blade and includes side ends gradually tapering in height toward the first surface of the blade.

3. The surgical retractor of claim 2, wherein each side end of each elongated rib projection further tapers in width to a tip.

4. The surgical retractor of claim 1, wherein:

the non-slip texture comprises a plurality of projections, each of the plurality of projections having a first surface inclined in a direction away from a distal end of the blade.

5. The surgical retractor of claim 4, wherein each of the projections has a pyramid shape with a flattened tip.

6. The surgical retractor of claim 4, wherein:

the plurality of projections are arranged in a plurality of rows, each row extending in a width direction of the blade and each row including two or more projections; and each row is offset in the width direction relative to an adjacent row.

7. The surgical retractor of claim 1, wherein the blade includes a distal tip at a distal end of the blade, wherein the non-slip texture is formed on the distal tip of the blade.

8. The surgical retractor of claim 1, wherein the non-slip grip texture includes a plurality of projections having a height of about 1 mm with a deviation of ±20-25%.

9. The surgical retractor of claim 1, further comprising the illumination assembly, the illumination assembly including one or more light sources on the second surface of the blade.

10. The surgical retractor of claim 9, wherein:

the one or more light sources are mounted on a flexible circuit board, the flexible circuit board includes first and second metallic layers provided on opposing surfaces of the flexible circuit board, and each of the first and second metallic layers being configured to dissipate heat generated by the one or more light sources.

11. The surgical retractor of claim 9, further comprising at least one smoke evacuation channel extending along at least a portion of the blade and configured to fluidly communicate with a suction source, wherein the one or more light sources are mounted on a flexible circuit board, and wherein the at least one smoke evacuation channel overlaps with a portion of the flexible circuit board.

12. The surgical retractor of claim 9, further comprising at least one smoke evacuation channel extending along at least a portion of the blade and configured to fluidly communicate with a suction source, wherein the at least one smoke evacuation channel is offset along a width of the blade from one or more light sources.

13. The surgical retractor of claim 1, wherein a distal end of the handle extends into a curved section offset from a central plane of the handle, and wherein the curved section accommodates a controller for controlling operation of the illumination assembly or the smoke evacuation assembly such that the controller is offset from the central plane of the handle.

14. The surgical retractor of claim 1, wherein one of the main blade body and the blade cover includes a plurality slots and the other of the main blade body and the blade cover includes a plurality of posts corresponding in positions to the plurality of slots and configured to engage with the plurality of slots so as to attach the main blade body with the blade cover.

15. The surgical retractor of claim 14, wherein each of the plurality of posts have a different cross-section from a cross-section of each of the plurality of slots.

16. A surgical retractor comprising:

a blade having a first surface and a second surface opposite from the first surface, wherein the blade includes a main blade body forming the first surface and a blade cover covering at least a portion of the main blade body and forming the second surface; and a handle extending from a proximal end of the blade, wherein the first surface of the blade includes a non-slip texture having a preferential grip in a first direction corresponding to direction of extraction of the surgical retractor from an incision and having a minimal or no grip in a second direction opposite to the first direction and in a third direction transverse to the first and second directions, and wherein one of the main blade body and the blade cover includes a plurality of slots and the other of the main blade body and the blade cover includes a plurality of posts corresponding in positions to the plurality of slots and configured to engage with the plurality of slots so as to attach the main blade body with the blade cover.

17. The surgical retractor of claim 16, further comprising an illumination assembly including one or more light sources on the second surface of the blade.

18. The surgical retractor of claim 16, wherein:

the non-slip texture comprises a plurality of elongated rib projections extending in a width direction of the blade, and each of the elongated rib projections is inclined in a direction away from a distal end of the blade and includes side ends gradually tapering in height toward the first surface of the blade.

19. The surgical retractor of claim 16, wherein the blade includes a distal tip at a distal end of the blade, wherein the non-slip texture is formed on the distal tip of the blade.

20. A surgical retractor comprising:

a blade having a first surface and a second surface opposite from the first surface; and a handle extending from a proximal end of the blade, wherein the first surface of the blade includes a non-slip texture having a preferential grip in a first direction corresponding to direction of extraction of the surgical retractor from an incision and having a minimal or no grip in a second direction opposite to the first direction and in a third direction transverse to the first and second directions, and wherein a distal end of the handle extends into a curved section offset from a central plane of the handle, and wherein the curved section accommodates a controller for controlling operation of an illumination assembly or a smoke evacuation assembly such that the controller is offset from the central plane of the handle.

* * * * *